US012372515B2

(12) United States Patent
Murphy et al.

(10) Patent No.: US 12,372,515 B2
(45) Date of Patent: Jul. 29, 2025

(54) ENGINEERED TISSUES FOR IN VITRO RESEARCH USES, ARRAYS THEREOF, AND METHODS OF MAKING THE SAME

(71) Applicant: Organovo, Inc., San Diego, CA (US)

(72) Inventors: Keith Murphy, Palos Verdes Estates, CA (US); Chirag Khatiwala, San Diego, CA (US); Scott Dorfman, San Diego, CA (US); Benjamin Shepherd, San Diego, CA (US); Sharon Presnell, San Diego, CA (US); Justin Robbins, La Jolla, CA (US)

(73) Assignee: Organovo, Inc., San Diego, CA (US)

( * ) Notice: Subject to any disclaimer, the term of this patent is extended or adjusted under 35 U.S.C. 154(b) by 772 days.

(21) Appl. No.: 17/013,165

(22) Filed: Sep. 4, 2020

(65) Prior Publication Data
US 2021/0123906 A1 Apr. 29, 2021

Related U.S. Application Data

(63) Continuation of application No. 16/029,919, filed on Jul. 9, 2018, now abandoned, which is a continuation of application No. 13/612,768, filed on Sep. 12, 2012, now abandoned.

(60) Provisional application No. 61/533,757, filed on Sep. 12, 2011, provisional application No. 61/533,761, filed on Sep. 12, 2011, provisional application No. 61/533,753, filed on Sep. 12, 2011.

(51) Int. Cl.
C12N 5/071 (2010.01)
A61L 27/34 (2006.01)
A61L 27/38 (2006.01)
A61L 27/50 (2006.01)
G01N 33/50 (2006.01)

(52) U.S. Cl.
CPC .......... G01N 33/5088 (2013.01); A61L 27/34 (2013.01); A61L 27/38 (2013.01); A61L 27/3891 (2013.01); A61L 27/50 (2013.01); C12N 5/0691 (2013.01); C12N 5/0697 (2013.01); G01N 33/5082 (2013.01); C12N 2502/27 (2013.01); C12N 2502/28 (2013.01); C12N 2513/00 (2013.01)

(58) Field of Classification Search
None
See application file for complete search history.

(56) References Cited

U.S. PATENT DOCUMENTS

| 4,759,764 A | 7/1988 | Fawcett et al. |
| 4,808,435 A | 2/1989 | Cropp et al. |
| 5,099,090 A | 3/1992 | Allan et al. |
| 6,315,469 B1 | 11/2001 | Alvarez et al. |
| 6,401,795 B1 | 6/2002 | Cesarano, III et al. |
| 6,454,972 B1 | 9/2002 | Morisette et al. |
| 6,520,997 B1 | 2/2003 | Pekkarinen et al. |
| 6,537,567 B1 | 3/2003 | Niklason et al. |
| 6,561,607 B1 | 5/2003 | Lubinsky et al. |
| 6,568,787 B1 | 5/2003 | Girones et al. |
| 6,642,243 B1 | 11/2003 | Imanzahrai |
| 6,713,772 B2 | 3/2004 | Goodman et al. |
| 6,939,489 B2 | 9/2005 | Moszner et al. |
| 6,942,830 B2 | 9/2005 | Mulhaupt et al. |
| 6,979,670 B1 | 12/2005 | Lyngstadaas et al. |
| 6,986,739 B2 | 1/2006 | Warren et al. |
| 7,051,654 B2 | 5/2006 | Boland et al. |
| 7,196,842 B2 | 3/2007 | Weigl et al. |
| 7,484,837 B2 | 2/2009 | Koga et al. |
| 7,625,198 B2 | 12/2009 | Lipson et al. |
| 7,651,665 B2 | 1/2010 | Gonzalez et al. |
| 7,680,555 B2 | 3/2010 | Dunn. et al. |
| 7,980,645 B2 | 7/2011 | Ohtsuka et al. |
| 8,143,055 B2 | 3/2012 | Forgacs et al. |
| 8,241,905 B2 | 8/2012 | Forgacs et al. |
| 8,343,740 B2 | 1/2013 | Gonda et al. |
| 8,580,546 B2 | 11/2013 | Gonda et al. |
| 8,931,880 B2 | 1/2015 | Murphy et al. |
| 9,315,043 B2 | 4/2016 | Murphy et al. |
| 9,481,868 B2 | 11/2016 | Nguyen et al. |
| 2001/0042942 A1 | 11/2001 | Hizumi et al. |
| 2002/0171178 A1 | 11/2002 | Dean et al. |
| 2002/0182633 A1 | 12/2002 | Chen et al. |
| 2002/0188349 A1 | 12/2002 | McAllister et al. |
| 2003/0049839 A1 | 3/2003 | Romero-Ortega et al. |
| 2003/0149505 A1 | 8/2003 | Mogensen |
| 2003/0153078 A1 | 8/2003 | Libera et al. |
| 2003/0175410 A1 | 9/2003 | Campbell et al. |
| 2003/0236588 A1 | 12/2003 | Jang et al. |
| 2004/0006405 A1 | 1/2004 | Chen et al. |

(Continued)

FOREIGN PATENT DOCUMENTS

| CA | 2306346 C | 1/1999 |
| EP | 2090584 A1 | 8/2009 |

(Continued)

OTHER PUBLICATIONS

Alajati et al., Nature Methods, vol. 5, No. 5, May 2008, pp. 439-445 (Year: 2008).*
Cui, X., et al., "Direct Human Cartilage Repair Using Three-Dimensional Bioprinting Technology," Tissue Engineering Part A 18(11-12): 1304-1312, Mary Ann Liebert, Inc., United States (2012).
Fujita, H., et al., "Fabrication of scaffold-free contractile skeletal muscle tissue using magnetite-incorporated myogenic C2C12 cells," Journal of Tissue Engineering and Regenerative Medicine 4(6):437-443, Wiley, United States (2010).
Hierlihy, A.M., et al., "The post-natal heart contains a myocardial stem cell population," FEBS Letters 530:239-243, Wiley, United States (2002).
Pearson Education. Human Heart Illustration (2004).

(Continued)

Primary Examiner — Evelyn Y Pyla
(74) Attorney, Agent, or Firm — Sterne, Kessler, Goldstein & Fox P.L.L.C.

(57) ABSTRACT

Disclosed are living, three-dimensional tissue constructs for in vitro scientific and medical research, arrays thereof, and methods of making said tissues and arrays.

18 Claims, 23 Drawing Sheets

(56) References Cited

U.S. PATENT DOCUMENTS

| | | |
|---|---|---|
| 2004/0132184 A1 | 7/2004 | Dennis et al. |
| 2004/0197367 A1 | 10/2004 | Rezania et al. |
| 2004/0219133 A1 | 11/2004 | Lyles |
| 2004/0237822 A1 | 12/2004 | Boland et al. |
| 2004/0253365 A1 | 12/2004 | Warren et al. |
| 2005/0009178 A1 | 1/2005 | Yost et al. |
| 2005/0091576 A1 | 4/2005 | Relyea et al. |
| 2005/0169962 A1 | 8/2005 | Bhatia et al. |
| 2005/0226856 A1 | 10/2005 | Ahlfors |
| 2005/0276791 A1 | 12/2005 | Hansford et al. |
| 2006/0099287 A1 | 5/2006 | Kim et al. |
| 2006/0198918 A1 | 9/2006 | Koyagi et al. |
| 2006/0237880 A1 | 10/2006 | Wicker et al. |
| 2006/0270032 A1 | 11/2006 | Bhatia et al. |
| 2007/0116678 A1 | 5/2007 | Sung et al. |
| 2007/0142916 A1 | 6/2007 | Olson et al. |
| 2007/0200276 A1 | 8/2007 | Mackey et al. |
| 2007/0231787 A1 | 10/2007 | Voelker |
| 2007/0299508 A1 | 12/2007 | Morrison et al. |
| 2008/0070304 A1 | 3/2008 | Forgacs et al. |
| 2008/0097575 A1 | 4/2008 | Cottone |
| 2008/0131476 A1 | 6/2008 | Kanzaki et al. |
| 2008/0192074 A1 | 8/2008 | Dubois et al. |
| 2008/0193910 A1 | 8/2008 | Larkin et al. |
| 2009/0076531 A1 | 3/2009 | Richardson et al. |
| 2009/0117087 A1 | 5/2009 | Carroll et al. |
| 2009/0142307 A1 | 6/2009 | Athanasiou et al. |
| 2009/0206522 A1 | 8/2009 | Hein et al. |
| 2009/0208466 A1 | 8/2009 | Yoo et al. |
| 2009/0208577 A1 | 8/2009 | Xu et al. |
| 2009/0239302 A1 | 9/2009 | Decher et al. |
| 2009/0248145 A1 | 10/2009 | Chan et al. |
| 2009/0267269 A1 | 10/2009 | Lim et al. |
| 2010/0041134 A1 | 2/2010 | Forgacs et al. |
| 2010/0056390 A1 | 3/2010 | Fischbach |
| 2010/0160183 A1 | 6/2010 | Xu et al. |
| 2010/0190246 A1 | 7/2010 | Hase |
| 2010/0191360 A1 | 7/2010 | Napadensky et al. |
| 2010/0254900 A1 | 10/2010 | Campbell et al. |
| 2011/0064784 A1 | 3/2011 | Mullens et al. |
| 2011/0172611 A1 | 7/2011 | Yoo et al. |
| 2011/0180914 A1 | 7/2011 | Do et al. |
| 2011/0212501 A1 | 9/2011 | Yoo |
| 2011/0250688 A1 | 10/2011 | Hasan |
| 2012/0045770 A1 | 2/2012 | Pongracz et al. |
| 2012/0089238 A1 | 4/2012 | Kang et al. |
| 2012/0116568 A1 | 5/2012 | Murphy et al. |
| 2012/0196343 A1 | 8/2012 | Forgacs et al. |
| 2012/0288938 A1 | 11/2012 | Forgacs et al. |
| 2013/0108726 A1 | 5/2013 | Uckelmann et al. |
| 2013/0164339 A1 | 6/2013 | Murphy et al. |
| 2013/0190210 A1* | 7/2013 | Murphy ............. G01N 33/5082 435/402 |
| 2013/0193619 A1 | 8/2013 | Church et al. |
| 2013/0236431 A1 | 9/2013 | Gourdie et al. |
| 2013/0345794 A1 | 12/2013 | Khatiwala et al. |
| 2014/0012225 A1 | 1/2014 | Yoo et al. |
| 2014/0012407 A1 | 1/2014 | Murphy et al. |
| 2014/0044822 A1 | 2/2014 | Mulliken |
| 2014/0093932 A1 | 4/2014 | Murphy et al. |
| 2014/0099709 A1 | 4/2014 | Presnell et al. |
| 2014/0131313 A1 | 5/2014 | Wakamatsu et al. |
| 2014/0265049 A1 | 9/2014 | Burris et al. |
| 2014/0274802 A1 | 9/2014 | Shepherd et al. |
| 2014/0287960 A1 | 9/2014 | Shepherd et al. |
| 2014/0358273 A1 | 12/2014 | Labossiere et al. |
| 2015/0037445 A1 | 2/2015 | Murphy et al. |
| 2015/0057786 A1 | 2/2015 | Murphy et al. |
| 2015/0344828 A1 | 12/2015 | Forgacs et al. |
| 2016/0122723 A1 | 5/2016 | Retting et al. |
| 2017/0130192 A1 | 5/2017 | Retting et al. |

FOREIGN PATENT DOCUMENTS

| | | |
|---|---|---|
| JP | 2001038981 A | 2/2001 |
| JP | 2005031144 A | 2/2005 |
| JP | 2006159117 A | 6/2006 |
| JP | 2010057439 A | 3/2010 |
| RU | 2371758 C2 | 10/2009 |
| WO | WO-1999001538 A1 | 1/1999 |
| WO | WO-2001068811 A2 | 9/2001 |
| WO | WO-2004108418 A1 | 12/2004 |
| WO | WO-2005025493 A2 | 3/2005 |
| WO | WO-2005081970 A3 | 9/2005 |
| WO | WO-2007076272 A2 | 7/2007 |
| WO | WO-2007115336 A2 | 10/2007 |
| WO | WO-2007115337 A2 | 10/2007 |
| WO | WO-2007124023 A3 | 11/2007 |
| WO | WO-2007125893 A1 | 11/2007 |
| WO | WO-2007126411 A2 | 11/2007 |
| WO | WO-2007136936 A2 | 11/2007 |
| WO | WO-2009102484 A2 | 8/2009 |
| WO | WO-2010008905 A2 | 1/2010 |
| WO | WO-2011038373 A2 | 3/2011 |
| WO | WO-2011088213 A1 | 7/2011 |
| WO | WO-2011097330 A2 | 8/2011 |
| WO | WO-2011107599 A1 | 9/2011 |
| WO | WO-2011119059 A1 | 9/2011 |
| WO | WO-2012003465 A2 | 1/2012 |
| WO | WO-2012054195 A2 | 4/2012 |
| WO | WO-2012131000 A1 | 10/2012 |

OTHER PUBLICATIONS

Tanaka, K., et al., "A Valved Hepatic Portoduodenal Instestinal Conduit for Biliary Atresia," *Annals of Surgery* 213(3):230-235, Lippincot Williams & Wilkins, United States (1991).

Office Action mailed Nov. 17, 2015, in United States U.S. Appl. No. 13/612,778, Murphy, K., et al., filed Sep. 12, 2012, 25 pages.

Office Action mailed Oct. 23, 2015, in United States U.S. Appl. No. 14/244,679, Forgacs, G., et al., filed Apr. 3, 2014, 16 pages.

ATCC Product Catalog MCF7 (ATCC® HTB-22TM) https://www.atcc.org/products/all/HTB-22.aspx?slp=1 #general information, retrieved Sep. 18, 2015.

ATCC Product catalog Primary Subcutaneous Pre-adipocytes; Normal, Human (ATCC® PCS-210-01OTM) https://www.atcc.org/Products/AII/PCS-210-01O.aspx?slp=1, retrieved Sep. 18, 2015.

Dirat, B., et al., "Cancer-associated adipocytes exhibit an activated phenotype and contribute to breast cancer invasion," *Cancer Research* 71(7):2455-2465, American Association for Cancer Research, United States (2011).

Egebald, M., et al., "Tumors as organs: complex tissues that interface with the entire organism," *Developmental Cell* 18(6):884-901, Elsevier, Netherlands (2010).

Forgacs, G., et al., "Biological Relevance of Tissue Liquidity and Viscoelasticity," Eds. A. Deutsch, M. Falcke, J. Howard and W. Zimmermann. Birkhauser. pp. 269-277 (2004).

Grange, C., et al., "Isolation and characterization of human breast tumor-derived endothelial cells," *Oncology Reports* 15(2):381-386, Spandidos Publications, United Kingdom (2006).

Izaguirre, J.A., et al., "CompuCell, a multi-model framework for simulation of morphogenesis," *Bioinformatics* 20(7):1129-1137, Oxford University Press, United Kingdom (2004).

Jakab, K., et al., "Organ printing: fiction or science," *Biorheology* 43(3-4):371-375, IOS Press, Netherlands (2004).

Jakab, K., et al., "Three-dimensional tissue constructs built by bioprinting," *Biorheology* 43(3-4):509-513, IOS Press, Netherlands (2006).

Khatiwala, C., et al., "3D Cell Bioprinting for Regenerative Medicine Research and Therapies," *Gene Therapy and Regulation* 7(1):1-19, World Scientific, Singapore (2012).

Mironov et al. Organ printing: self-assembling cell aggregates as a "bioink". Science and Medicine 9:69-71 (2003).

Neagu, A., et al., "Role of physical mechanisms in biological self-organization," *Physical Review Letters* 95(17):178104, American Physical Society, United States (2005).

(56) References Cited

OTHER PUBLICATIONS

Newman, S.A., et al., "Before programs: the physical origination of multicellular forms," *International Journal of Developmental Biology* 50(2-3):289-299, University of the Basque Country Press, Spain (2006).
PCT/US2014/026679 International Preliminary Report on Patentability dated Sep. 24, 2015.
Riken. Self-healing hydrogels ease into production. Research Highlights: Materials. Downloaded from the Riken website: http://www.riken.jp/en/research/rikenresearch/highlights/7543/ (Nov. 1, 2013) [accessed Apr. 27, 2015].
Shafrir, Y., et al., "Mechanotransduction through the cytoskeleton," *American Journal of Physiology* 282:479-486, American Physiological Society, United States (2002).
Sheehan, T., et al., "Recent Patents and Trends in Bioprinting," *Recent Patents on Biomedical Engineering* 4:26-32 (2011).
Office Action mailed Sep. 8, 2015, in U.S. Appl. No. 13/634,863, Khatiwala, C., et al., filed May 15, 2013, 9 pages.
Office Action mailed Sep. 23, 2015, in U.S. Appl. No. 13/794,368, Murphy, K., et al., filed Mar. 11, 2013, 18 pages.
Office Action mailed Sep. 9, 2015, in U.S. Appl. No. 14/295,226, Shepherd, B.R., et al., filed Jun. 3, 2014, 9 pages.
Office Action mailed Jul. 15, 2015, in U.S. Appl. No. 14/447,412, Murphy, K., et al., filed Jul. 30, 2014, 13 pages.
Office Action dated Oct. 8, 2015, in U.S. Appl. No. 14/678,392, King, S..M., et al., filed Apr. 3, 2015, 25 pages.
Office Action dated Sep. 24, 2015, in U.S. Appl. No. 14/678,392, King, S.M., et al., filed Apr. 3, 2015, 26 pages.
Office Action dated Sep. 25, 2015, in U.S. Appl. No. 14/796,910, Murphy, K., et al., filed Jul. 10, 2015, 9 pages.
Zhang, Y., et al., "Characterization of printable cellular microfluidic channels for tissue engineering," *Biofabrication* 5:025004, IOP Publishing, United Kingdom (2013).
Kasko, A., "Degradable Poly(ethylene glycol) Hydrogels for 2D and 3D Cell Culture," Aldrich Materials Science, pp. 67-75 (no date available).
International Preliminary Report on Patentability for International Application No. PCT/US2005/05735, The International Bureau of WIPO, mailed on Mar. 3, 2009, 6 pages.
International Preliminary Report on Patentability for International Application No. PCT/US2013/046519, The International Bureau of WIPO, mailed on Dec. 23, 2014, 11 pages.
International Search Report and Written Opinion for International Application No. PCT/US2014/048962, Korean Intellectual Property Office, Republic of Korea dated Nov. 10, 2014.
Smith. A, direct-write three-dimensional Bioassembly tool for regenerative medicine. The University of Arizona, Nov. 1, 2005, pp. 1-291.
Office Action mailed Jan. 14, 2015, in U.S. Appl. No. 13/246,428, Murphy, K., et al., filed Sep. 27, 2011, 9 pages.
Office Action mailed Nov. 14, 2014, in U.S. Appl. No. 13/801,780, Presnell, S.C., et al., filed Mar. 13, 2013, 20 pages.
Office Action mailed Nov. 26, 2014, in U.S. Appl. No. 13/794,368, Murphy, K., et al., filed Mar. 11, 2013, 16 pages.
Office Action mailed Jan. 28, 2015, in U.S. Appl. No. 13/634,863, Khatiwala, C., et al., filed May 15, 2013, 7 pages.
Office Action mailed Mar. 3, 2015, in U.S. Appl. No. 14/447,412, Murphy, K., et al., filed Jul. 30, 2014, 36 pages.
Xu, F., et al., "A three-dimensional in vitro ovarian cancer coculture model using a high-throughput cell patterning platform," *Biotechnology Journal* 6(2):204-212, Wiley, United States (2011).
Tao et al. Bio-printing of living organized tissues using an inkjet technology. Database Accession No. PREV200700335042; FASEB Journal 23(5):A636 (2007).
Xu, T., et al., "In vivo generation of functional tissues using the inkjet printing technology," *Tissue Engineering* 13(7):1713-1714, SAGE Publishing, United States (2007).
Moon, S., et al., "Layer by Layer Three-dimensional Tissue Epitaxy by Cell-Laden Hydrogel Droplets," *Tissue Engineering Part C* 16(1):157-166, Mary Ann Liebert Inc., United States (2010).

Fuellhase, C., et al., "264 Generation of Organized Bladder Tissue Constructs Using a Novel Hybrid Printing System," *European Urology Supplements* 8(4):186, Elsevier, Netherlands (2009).
Halley, D., "Growing Organs in the Lab" Singularity Hub.com, accessed at https://singularityhub.com/2009/06/08/growing-organs-in-the-lab/, dated Jun. 8, 2009.
International Preliminary Report on Patentability for International Application No. PCT/US2013/036479, The International Bureau of WIPO, mailed on Oct. 21, 2014, 8 pages.
Office Action mailed Nov. 7, 2014, in U.S. Appl. No. 13/612,778, Murphy, K., et al., filed Sep. 12, 2012, 18 pages.
Office Action mailed Oct. 8, 2014, in U.S. Appl. No. 14/295,226, Shepherd, B.R., et al., filed Jun. 3, 2014, 10 pages.
Examination Report submitted in Australian Application No. AU2011318437 submitted on Dec. 10, 2013, filing date: Sep. 27, 2011.
Bioscaffolder 2008, www.syseng.de, Syseng Dipl.-Ing. Hendrik John.
Office Action for Canadian Patent Application No. CA2729559, dated Dec. 10, 2013.
Chaterji et al. "Scaffold-Free In Vitro Arterial Mimetics: The Importance of Smooth Muscle-Endothelium Contact," *Tissue Engineering Part A* 16:1901-1912, Mary Ann Liebert Inc., United States (2010).
Office Action for Chinese Patent Application No. CN201180020669.1 dated Jun. 4, 2014 (w/English Translation).
Extended European Search Report for European Patent Application No. EP11756695l.7 dated Jan. 28, 2014.
Fedorovich, N.E., et al., "Distinct Tissue Formation by Heterogeneous Printing of Osteo- and Endothelial Progenitor Cells," *Tissue Engineering: Part A* 17(15-16):2113-2123, Mary Ann Liebert Inc., United States (2011).
Fedorovich, N.E., et al., "Three-Dimensional Fiber Deposition of Cell-Laden, Viable Patterned Constructs for Bone Tissue Printing," *Tissue Engineering: Part A* 14(1):127-135, Mary Ann Liebert Inc., United States (2008).
Ghorbanian, S., et al., "Microfluidic direct writer with integrated declogging mechanism for fabricating cell-laden hydrogel constructs," *Biomed Microdevices* 16:387-395, Springer, Germany (2014).
Gruene, M., et al., "Laser Printing of Stem Cells for Biofabrication of Scaffold-Free Autologous Grafts," *Tissue Engineering: Part C* 17(1):79-89, Mary Ann Liebert Inc., United States (2011).
Guillemot, F., et al., "High-throughput laser printing of cells and biomaterials for tissue engineering," *Acta biomaterialia* 6:2494-2500, Elsevier, Netherlands (2010).
Ito, A., et al., "Novel Methodology for Fabrication of Tissue-Engineered Tubular Constructs Using Magnetite Nanoparticles and Magnetic Force," *Tissue Engineering* 11(9-10):1553-1561, SAGE Publishing, United States (2005).
Office Action for Japanese Patent Application No. JP 2011-516626 dated Feb. 4, 2014 (w/English Translation).
Office Action for Korean Patent Application No. KR 10-2012-7026891 dated Feb. 18, 2014 (w/English Translation).
Larkin, L., et al., "Structure and Functional Evaluation of Tendon-Skeletal Muscle Constructs Engineered in Vitro," *Tissue Engineering* 12(11):3149-3158, SAGE Publishing, United States (2006).
Mcguigan, A.P., et al., "Vascularized organoid engineered by modular assembly enables blood perfusion," *PNAS* 103(31):11461-11466, National Academy of Sciences, United States (2006).
Mehesz, A.N., et al., "Scalable robotic biofabrication of tissue spheroids," *Biofabrication* 3:1-8, IOP Publishing, United Kingdom (2011).
A. Chaux, "Pathology Outlines: Bladder, Normal Histology," Pathologyoutlines.com, accessed at https://www.pathologyoutlines.com/topic/bladderhistology.html , created on Jun. 1, 2011, 4 pages.
International Preliminary Report on Patentability for International Application No. PCT/US2009/48530, The International Bureau of WIPO, mailed on Jan. 13, 2011, 6 pages.
International Preliminary Report on Patentability for International Application No. PCT/US2011/023520, The International Bureau of WIPO, mailed on Aug. 16, 2012, 6 pages.

(56) References Cited

OTHER PUBLICATIONS

International Preliminary Report on Patentability for International Application No. PCT/US2012/054923, The International Bureau of WIPO, mailed on Mar. 20, 2014, 6 pages.
International Search Report and Written Opinion for International Application No. PCT/US2014/026679, Korean Intellectual Property Office, Republic of Korea, mailed on Jul. 22, 2014, 12 pages.
International Preliminary Report on Patentability for International Application No. PCT/US2012/054935, The International Bureau of WIPO, mailed on Mar. 12, 2014, 7 pages.
Office Action for Russian Patent Application No. RU2013122936, dated Jun. 26, 2014 (w/English Translation).
Shim, J., et al., "Bioprinting of a mechanically enhanced three-dimensional dual cell-laden construct for osteochondral tissue engineering using a multi-head tissue/organ building system," *Journal of Micromechanics and Microengineering* 22(Article No. 085014):1-11, IOP Publishing, United Kingdom (2012).
Skardal, A., et al., "Bioprinting vessel-like constructs using hyaluronan hydrogels crosslinked with tetrahedral polyethylene glycol tetracrylates," *Biomaterials* 31:6173-6181, Elsevier, Netherlands (2010).
Smith, C.M., et al., "Characterizing Environment Factors that Impact the Viability of Tissue- Engineered Constructs Fabricated by a Direct-Write Bioassembly Tool," *Tissue Engineering* 13(2):373-385, SAGE Publishing, United States (2007).
Office Action mailed Aug. 26, 2014, in U.S. Appl. No. 13/246,428, Murphy, K. et al., filed Sep. 27, 2011, 10 pages.
Office Action mailed Apr. 28, 2014, in U.S. Appl. No. 13/612,778, Murphy, K. et al., filed Sep. 12, 2012, 20 pages.
Office Action mailed Jun. 26, 2014, in U.S. Appl. No. 13/968,313, Murphy, K. et al., filed Aug. 15, 2013, 10 pages.
Wake Forest Baptist Medical Center (Wake Forest Physician Reports First Human Recipients of Laboratory-Grown Organs. 2006 pp. 1-2).
Examination Report for Australian Patent Application No. AU2009271223 dated Sep. 5, 2013.
Boland, T., et al., "Cell and Organ Printing 2: Fusion of Cell Aggregates in Three-Dimensional Gels," *The Anatomical Record, Part A* 272:497-502, Wiley, United States (2003).
Office Action for Canadian Patent Application No. CA2793205 dated Nov. 7, 2013.
Office Action for Chinese Patent Application No. CN201180017227.1 dated Nov. 15, 2013.
Dominici, M., et al., "Minimal criteria for defining multipotent mesenchymal stromal cells," International Society for Cellular Therapy position statement, *Cytotherapy* 8:315-317, Elsevier, Netherlands (2006).
International Search Report for International Application No. PCT/US2013/046519, Korean Intellectual Property Office, Republic of Korea, mailed on Sep. 5, 2013, 3 pages.
Marga, F., et al., Bioprint Engineered Fully Biological Nerve Graft, Poster Presentation, TERMIS, Dec. 5-8, 2010, Orlando, Florida, 1 page.
Tsonis, P.A., et al., "A unique aged human retinal pigmental epithelial cell line useful for studying lens differentiation in vitro," 45:753-758, University of the Basque Country Press, Spain (2001).
Office Action for Russian Patent Application No. RU 2012142992 dated Aug. 1, 2013.
Schuster, D., et al., "Why Drugs Fail—A Study on Side Effects in New Chemical Entities," Current Pharmaceutical Design 11:3545-3559, Bentham Science Publishers, United Arab Emirates (2005).
Office action mailed Sep. 24, 2013, in U.S. Appl. No. 13/529,172, Forgacs, G., et al., filed Jun. 21, 2012, 13 pages.
Examination Report for Australian Patent Application No. AU2011212998 dated Jul. 26, 2013.
European Search Report for European Patent Application No. EP11740319.6 dated Jul. 16, 2013.
Frisman, I., et al., "Nanostructuring of PEG-fibrinogen polymeric scaffolds," *Acta Biomaterialia*, 6(7):2518-2524, Elsevier, Netherlands (2010).
Hockaday, L., et al., "Rapid 3D printing of anatomically accurate and mechanically heterogeneous aortic valve hydrogel scaffolds," *Biofabrication* 4(3):035005, IOP Publishing, United Kingdom (2012).
Marga, F., et al., "Toward Engineering Functional Organ Modules by Additive Manufacturing," *Biofabrication* 4:022001, IOP Publishing, United Kingdom (2012).
Marga, Francoise S., et al. "Construction of a Bioprinted Fully Biological Nerve Graft," *Biophysical Journal.* 96:634a (Abstract).
International Search Report for International Application No. PCT/US2013/036479, Korean Intellectual Property Office, Republic of Korea, mailed on Jul. 25, 2013, 4 pages.
Office action mailed Jan. 6, 2011, in U.S. Appl. No. 10/590,446, Forgacs, G. et al., filed Oct. 10, 2017, 13 pages.
Office action mailed Sep. 1, 2011, in U.S. Appl. No. 10/590,446, Forgacs, G. et al., filed Oct. 10, 2017, 14 pages.
Office action mailed Oct. 28, 2004, in U.S. Appl. No. 10/666,836, Boland, T. et al., filed Sep. 17, 2003, 5 pages.
Office action mailed Dec. 10, 2008, in U.S. Appl. No. 11/227,489, Robbins, N.F. et al., filed Sep. 16, 2005, 16 pages.
Office action mailed Jul. 8, 2009, in U.S. Appl. No. 11/227,489, Robbins, N.F. et al., filed Sep. 16, 2005, 11 pages.
Office action mailed Dec. 31, 2012, in U.S. Appl. No. 13/020,000, Forgacs, G. et al., filed Feb. 2, 2011, 15 pages.
Office action mailed Jul. 3, 2013, in U.S. Appl. No. 13/020,000, Forgacs, G. et al., filed Feb. 2, 2011, 12 pages.
Office action mailed Mar. 19, 2013, in U.S. Appl. No. 13/402,215, Forgacs, G. et al., filed Feb. 22, 2012, 15 pages.
Wang, J., et al., "Bone marrow mesenchymal stem cells promote cell proliferation and neurotrophic function of Schwann cells in vitro and in vivo," *Brain Research* 1262:7-15, Elsevier, Netherlands (2009).
Office Action mailed Feb. 2, 2016, in U.S. Appl. No. 13/801,780, Presnell, S. et al., filed Mar. 3, 2013, 15 pages.
Office Action mailed Apr. 19, 2016, in U.S. Appl. No. 14/678,392, King, S.M. et al., filed Apr. 3, 2015, 24 pages.
LifeMap Sciences, Inc., "Skeletal Muscle—Development and Stem Cells," accessed at https://discovery.lifemapsc.com/in-vivo-development/skeletal-muscle, accessed on Jun. 24, 2017, 6 pages.
Matthay, M.A. and Clements, J.A., "Coagulation-dependent mechanisms and asthma," *The Journal of Clinical Investigation* 114(1):20-23, The American Society for Clinical Investigation, United States (2004).
Memon, I.A., et al., "Repair of impaired myocardium by means of implantation of engineered autologous myoblast sheets," *The Journal of Thoracic and Cardiovascular Surgery* 130(5):1333-1341, Elsevier Inc., United States (2005).
Miyagawa, S., et al., "Impaired Myocardium Regeneration With Skeletal Cell Sheets—A Preclinical Trial for Tissue-Engineered Regeneration Therapy," *Transplantation* 90(4):364-372, Lippincott Williams & Wilkins, United States (2010).
Schnapp, L., "Role of Lung Pericytes and Stromal Cells in the Pathogenesis of Pulmonary Fibrosis," 2013 Research Grant Program Winning Abstract, accessed at http://www.bdbiosciences.com/documents/Grant_Lynn_Schnapp.pdf, accessed on Jun. 24, 2017, 2 pages.
Sekine, H., et al., "Endothelial Cell Coculture Within Tissue-Engineered Cardiomyocyte Sheets Enhances Neovascularization and Improves Cardiac Function of Ischemic Hearts," *Circulation* 118(Suppl 1):S145-S152, American Heart Association, Inc., United States (2008).
Office Action mailed Sep. 13, 2016, in U.S. Appl. No. 13/612,778, Murphy, K. et al., filed Sep. 12, 2012, 11 pages.
Office Action mailed Jul. 5, 2017, in U.S. Appl. No. 13/612,778, Murphy, K. et al., filed Sep. 12, 2012, 23 pages.
Office Action mailed Feb. 2, 2016, in U.S. Appl. No. 13/801,780, Presnell, S.C. et al., filed Mar. 13, 2013, 15 pages.
Office Action mailed Sep. 7, 2016, in U.S. Appl. No. 13/801,780, Presnell, S.C. et al., filed Mar. 13, 2013, 12 pages.
Amendment and Reply Under 37 C.F.R. § 1.114 with Declaration Under 37 C.F.R. § 1.132 and Exhibit A filed Dec. 7, 2016, in U.S. Appl. No. 13/801,780, Presnell, S.C. et al., filed Mar. 13, 2013, 21 pages.

(56) References Cited

OTHER PUBLICATIONS

Office Action mailed Aug. 14, 2017, in U.S. Appl. No. 13/801,780, Presnell, S.C. et al., filed Mar. 13, 2013, 12 pages.
Partial English language translation of Japanese Publication No. JP 2010-057439 A.
First Examination Report for Australian Patent Application No. AU2011227282 dated Jan. 9, 2013.
Baltich, J., et al., "Development of a Scaffoldless Three-Dimensional Engineered Nerve Using a Nerve-Fibroblast Co-Culture," *In Vitro Cellular & Developmental Biology—Animal* 46:438-444, Springer, United States (2010).
Office action for Chinese Patent Application No. CN200980131924, dated Jan. 14, 2013.
Constans, A., "Body by Science," The Scientist, Oct. 6, 2003, vol. 17, No. 19, http:i/www.the-scientist. comiarticle/display/141541, 7 pages.
Dai, W., et al., "Fibroblast Aggregation by Suspension with Conjugates of Poly (ethylene glycol) and RGD" *Biotechnology and Bioengineering* 50(4):349-356, Wiley, United States (1996).
Edelman, E.R. "Vascular Tissue Engineering: Designer Arteries," *Circulation Research* 85(12):1115-1117, Lippincot Williams & Wilkins, United States (1999).
Eisenberg, C.A., et al. "Bone Marrow Cells Transdifferentiate to Cardiomyocytes When Introduced into the Embryonic Heart," *Stem Cells* 24:1236-1245, Oxford University Press, United Kingdom (2006).
Extended European Search Report for European Patent Application No. EP09798534.5 mailed Jan. 10, 2013.
Forgacs, G., et al., "Viscoelastic Properties of Living Embryonic Tissues: a Quantitative Study," *Biophysical Journal* 74 (5):2227-2234, Cell Press, United States (1998).
Foty, R.A., et al., "Surface tensions of embryonic tissues predict their mutual envelopment behavior," *Development* 122(5):1611-1620, The Company of Biologists, United Kingdom (1996).
Foty, R.A., et al., "The Differential Adhesion Hypothesis: A Direct Evaluation," *Developmental Biology* 278:255-263, Elsevier, Netherlands (2005).
Furukawa, K.S., et al. "Scaffold-free cartilage tissue by mechanical stress loading for tissue engineering," *In Tissue Engineering*, ed by Daniel Eberli. InTech 2010, p. 409-428.
Furukawa, K.S., et al., "Formation of Human Fibroblast Aggregates (Spheroids) by Rotational Culture," *Cell Transplantation* 10:441-445, SAGE Publishing, United States (2001).
Furukawa, K.S., et al., "Tissue-engineered Skin Using Aggregates of Normal Human Skin Fibroblasts and Biodegradable Material," *Journal of Artificial Organs* 4:353-356, Springer, United States (2001).
Examination Report for British Patent Application No. GB1008781.5 dated Sep. 22, 2010.
Examination Report for British Patent Application No. GB1203622.4 dated Jul. 16, 2012.
Glazier, J.A., et al., "Simulation of the Differential Adhesion Driven Rearrangement of Biological Cells," *Physical Review E* 47:2128-2154, American Physical Society, United States (1993).
Glicklis, R., et al., "Modeling Mass Transfer in Hepatocyte Spheroids via Cell Viability, Spheroid Size, and Hepatocellular Functions," *Biotechnology and Bioengineering* 86:672-680, Wiley, United States (2004).
Graner, F., et al., "Simulation of Biological Cell Sorting Using a Two-Dimensional Extended Potts Model," *Physical Review Letters* 69:2013-2016, American Physical Society, United States (1992).
Gruene, M., et al., "Laser printing of three-dimensional multicellular arrays for studies of cell-cell and cell-environment interactions." *Tissue Engineering Part C* 7(10):973-982, Mary Ann Liebert Inc., United States (2011).
Guenard, V., et al., "Syngeneic Schwann Cells Derived from Adult Nerves Seeded in Semipermeable Guidance Channels Enhance Peripheral Nerve Regeneration," *The Journal of Neuroscience* 12:3310-3320, Society for Neuroscience, United States (1992).

Hadlock, T., et al., "A Polymer Foam Conduit Seeded with Schwann Cells Promotes Guided Peripheral Nerve Regeneration," *Tissue Engineering* 6:119-127, SAGE Publishing, United States (2000).
Harvey, A.R., et al., "Schwann cells and fetal tectal tissue cografted to the midbrain of newborn rats: fate of Schwann cells and their influence on host retinal innervation of grafts," *Experimental Neurology* 134(2):179-91, Elsevier, Netherlands (1995).
Hubbard, et al., "Bioengineered, Autologous, Scaffold-free Nerve Conduit for Peripheral Nerve Repair," Abstract, AAHS/ASPNIASRM 2011, Annual Scientific Meetings Program Book, pp. 140 and 159, Jan. 12-18, 2011.
Iwasaki, K., et al., "Bioengineered Three-Layered Robust and Elastic Artery Using Hemodynamically-Equivalent Pulsatile Bioreactor," *Circulation* 118(14 Suppl):S53-S57, Lippincott Williams & Wilkins, United States (2008).
Jakab, K., et al., "Engineering Biological Structures of Prescribed Shape Using Self-assembling Multicellular Systems," *PNAS USA* 101:2864-2869, National Academy of Sciences, United States (2004).
Jakab, K., et al., "Tissue Engineering by Self-Assembly and Bioprinting of living cells," *Biofabrication* 2:022001, IOP Publishing, United Kingdom (2010).
Jakab, K., et al., "Relating Cell and Tissue Mechanics: Implications and Applications," *Developmental Dynamics* 237:2438-2449, Wiley, United States (2008).
Jakab, K., et al., "Tissue Engineering by Self-Assembly of Cells Printed into Topologically Defined Structures," *Tissue Engineering Part A* 14:413-421, Mary Ann Liebert Inc., United States (2008).
Kelm, J.M., et al., "Microscale Tissue Engineering Using Gravity-Enforced Cell Assembly," *Trends in Biotechnology* 22:195-202, Elsevier, Netherlands (2004).
Kelm, J.M., et al., "Design of Custom-Shaped Vascularized Tissues Using Microtissue Spheriods as Minimal Building Units," *Tissue Engineering* 12:2151-2160, IOP Publishing, United States (2006).
Koibuchi, N., et al., "Behavior of cells in artificially made cell aggregates and tissue fragments after grafting to developing hind limb buds in Xenopus laevis," *The International Journal of Developmental Biology* 43(2):141-148, University of the Basque Country Press, Spain (1999).
Korff, T., et al., "Blood Vessel Maturation in a 3-Dimensional Spheroidal Coculture Model: Direct Contact with Smooth Muscle Cells Regulates Endothelial Cell Quiescence and Abrogates VEGF Responsiveness," *The FASEB Journal* 15:447-457, FASEB, United States (2001).
L'Heureux, N., et al., "A completely biological tissue-engineered human blood vessel," *The FASEB Journal* 12(1):47-56, FASEB, United States (1998).
L'Heureux, N., et al., "Human tissue-engineered blood vessels for adult arterial revascularization," *Nature Medicine* 12(3):361-365, Springer, United Kingdom (2006).
L'Heureux, N., et al., "Sheet-Based Tissue Engineering From Bench Top to the First Clinical Use of a Completely Biological Tissue Engineered Vessel," *The FASEB Journal* 12(1):47-56, FASEB, United States (2006) (Abstract).
Lee, W., et al., "Multi-layered Culture of Human Skin Fibroblasts aud Keratinocytes Through Three-dimensional Freeform Fabrication," *Biomaterials* 30:1587-1595, Elsevier, Netherlands (2009).
Luo, Y., et al., "Three-dimensional microtissue assay for high-throughput cytotoxicity of Nanoparticles," *Analytical Chemistry* 84(15):6731-6738, ACS Publications, United States (2012).
Marga, F., et al., "Developmental Biology aud Tissue Engineering," *Birth Defects Research Part C* 81:320-328, Wiley, United States (2007).
Marga, F., et al., "Engineered Fully Biological Nerve Graft," Poster Presentation, Biophysical Society Meeting, Mar. 4, 2009, 1 page.
Martin, I., et al., "Computer-Based Technique for Cell Ainrregation Analysis and Cell Aggregation in In Vitro Chondrogenesis," *Cytometry* 28:141-146, Wiley, United States (1997).
Mironov, V., et al., "Bioprinting Living Structures," *Journal of Materials Chemistry* 17:2054-2060, RSC Publishing, United Kingdom (2007).
Mironov, V., et al., "Organ Printing: Computer-Aided Jet-Based 3D Tissue Engineering," *Trends in Biotechnology* 21:157-161, Elsevier, Netherlands (2003).

(56) References Cited

OTHER PUBLICATIONS

Mironov, V., et al., "Organ Printing: Tissue Spheroids as Building Blocks," *Biomaterials* 30:2164-2174, Elsevier, Netherlands (2009).
Mizumoto, H., et al., "Formation of Cylindrical Multicellular Aggregate (Cylindroid) and Express of Liver Specific Functions of Primary Rat Hepatocytes," *Cytotechnology*, 31:69-75, Springer, Germany (1999).
Mombach, J.C., et al., "Quantitative comparison between differential adhesion models and cell sorting in the presence and absence of fluctuations," *Physical Review Letters* 75(11):2244-2247, American Physical Society, United States (1995).
Mroue, R., et al., "Three-dimensional cultures of mouse mammary epithelial cells," *Methods in Molecular Biology* 945:221-250, Springer, United States (2013).
Paul, S.M., et al., "How to improve R&D productivity: the pharmaceutical industry's grand challenge," *Nature Reviews Drug Discovery* 9(3):203-214, Springer, United States (2010).
Nickerson, C.A., et al., "Three-Dimensional Tissue Assemblies: Novel Models for the Study of *Salmonella enterica* Serovar Typhimurium Pathogenesis," *Infection and Immunity* 69:7106-7120, American Society for Microbiology, United States (2001).
Niklason, L.E., and Langer, R.S., "Advances in Tissue Engineering of Blood Vessels and Other Tissues," *Transplant Immunology* 5(4):303-306, Elsevier, Netherlands (1997).
Norette, C., et al., "Scaffold-free vascular tissue engineering using bioprinting," *Biomaterials* 30:5910-5917, Elsevier, Netherlands (2009).
International Search Report for International Application No. PCT/US2011/028713, Korean Intellectual Property Office, Republic of Korea mailed on Nov. 30, 2011, 4 pages.
International Preliminary Report on Patentability and Written Opinion for International Application No. PCT/US2011/028713, The International Bureau of WIPO, mailed on Sep. 18, 2012, 9 pages.
International Preliminary Report on Patentability and Written Opinion for International Application No. PCT/US2011/053515, The International Bureau of WIPO, mailed on Apr. 23, 2013.
International Search Report for International Application No. PCT/US2011/023520, Korean Intellectual Property Office, Republic of Korea mailed on Oct. 31, 2011.
International Search Report and Written Opinion for International Application No. PCT/US2011/053515, Korean Intellectual Property Office, Republic of Korea mailed on May 1, 2012, 7 pages.
International Search Report for International Application No. PCT/US2005/05735, Korean Intellectual Property Office, Republic of Korea mailed on Dec. 7, 2007, 3 pages.
International Search Report for International Application No. PCT/US2009/48530, Korean Intellectual Property Office, Republic of Korea mailed on Mar. 15, 2010, 4 pages.
International Search Report for International Application No. PCT/US2012/054923, Korean Intellectual Property Office, Republic of Korea dated Feb. 26, 2013, 4 pages.
International Search Report for International Application No. PCT/US2012/054935, Korean Intellectual Property Office, Republic of Korea dated Feb. 28, 2013, 4 pages.
Perez-Pomares, J.M., and Foty, R.A., "Tissue Fusion and Cell Sorting in Embryonic Development and Disease: Biomedical Implications," *Bioessays* 28:809-821, Wiley, United States (2006).
Remuzzi, A., et al., "Vascular Smooth Muscle Cells on Hyaluronic Acid: Culture and Mechanical Characterization of an Engineered Vascular Construct," *Tissue Engineering* 10:699-710, SAGE Publishing, United States (2004).
Ryan, P.L., et al., "Tissue Spreading on Implantable Substrates is a Competitive Outcome of Cell-Cell vs. Cell-Substratum Adhesivity," *PNAS USA* 98:4323-4327, National Academy of Sciences, United States (2001).
"Sciperio, Inc. 2003 R&D 100 Award Winner", Sciperio, accessed at http://www.sciperio.com/news/20031016.asp, accessed on Feb. 1, 2005, 2 pages.
Siemionow, M., et al., "Chapter 8: Current Techniques and Concepts in Peripheral Nerve Repair," *International Review of Neurobiology* 87:141-172, American Press, United States (2009).
Smith, C., et al., "Three-Dimensional BioAssembly Tool for Generating Viable Tissue-Engineered Constructs," *Tissue Engineering* 10:1566-1576, SAGE Publishing, United States (2004).
Steinberg, M. S., "Does Differential Adhesion Govern Self-Assembly Processes in Histogenesis? Equilibrium Configurations and the Emergence of a Hierarchy Among Populations of Embryonic Cells," *The Journal of Experimental Zoology* 173:395-433, Wiley, United States (1970).
Steinberg, et al., "Liquid Behavior of Embryonic Tissues," in *Cell Behaviour*, pp. 583-697 (1982).
Stiles, E., "UA Wins R & D 100 Award for Machine that Prints Tissue Cell-by-Cell," UANews, Dec. 2, 2003, accessed at https://uanews.org/cgibinfflebObjects1UANews.woa/wa/goPrint?ArticleID=8305, accessed on Feb. 1, 2005, 2 pages.
Tang, M.D., et al., "Molding of Three-Dimensional Microstructures of Gels," *Journal of the American Chemical Society* 125:12988-12989, American Chemical Society, United States (2003).
Timmins, N.E., et al., "Hanging-drop Multicellular Spheroids as a Model of Tumour Angiogenesis," *Angiogenesis* 7(2):97-103, Springer, Netherlands (2004).
Tsang, V.L., and Bhatia, S.N., "Three-dimensional tissue fabrication," *Advanced drug delivery reviews* 56(11):1635-1647, Elsevier, Netherlands (2004).
Yamauchi, N., et al., "A Three-Dimensional Cell Culture Model for Bovine Endometrium: Regeneration of a Multicellular Spheroid Using Ascorbate," *Placenta* 24:258-269, Elsevier, Netherlands (2003).
Office Action mailed Feb. 7, 2018, in U.S. Appl. No. 13/612,768, Murphy, K. et al., filed Sep. 12, 2012, 16 pages.
Office Action mailed Jul. 24, 2017, in U.S. Appl. No. 13/612,768, Murphy, K. et al., filed Sep. 12, 2012, 25 pages.
Office Action mailed May 9, 2017, in U.S. Appl. No. 13/612,768, Murphy, K. et al., filed Sep. 12, 2012, 15 pages.
Office Action mailed Jul. 30, 2015, in U.S. Appl. No. 13/612,768, Murphy, K. et al., filed Sep. 12, 2012, 13 pages.
Office Action mailed Nov. 17, 2014, in U.S. Appl. No. 13/612,768, Murphy, K. et al., filed Sep. 12, 2012, 28 pages.
Office Action mailed May 30, 2014, in U.S. Appl. No. 13/612,768, Murphy, K. et al., filed Sep. 12, 2012, 16 pages.
Office Action mailed Oct. 1, 2013, in U.S. Appl. No. 13/612,768, Murphy, K. et al., filed Sep. 12, 2012, 13 pages.
Office Action mailed Jun. 5, 2020, in U.S. Appl. No. 16/029,919, Murphy, K. et al., filed Jul. 9, 2018, 10 pages.
Office Action mailed Nov. 19, 2019, in U.S. Appl. No. 16/029,919, Murphy, K. et al., filed Jul. 9, 2018, 12 pages.

\* cited by examiner

H&E  CD31  alpha-SMA

Fig. 18A (1) Glandular tissue / Cancer tissue

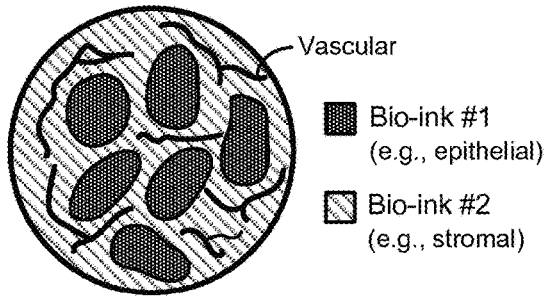

- Bio-ink #1 (e.g., epithelial)
- Bio-ink #2 (e.g., stromal)

(2) Composite tissue / Tissue interface

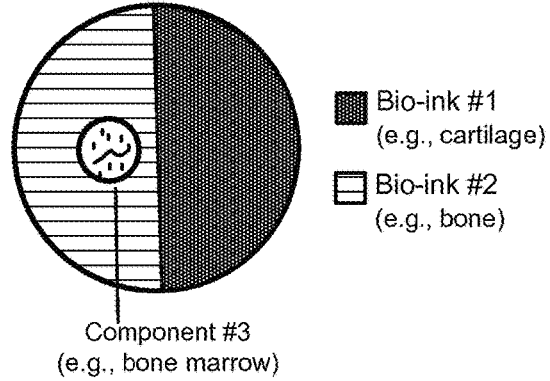

- Bio-ink #1 (e.g., cartilage)
- Bio-ink #2 (e.g., bone)
- Component #3 (e.g., bone marrow)

(3) Architecturally-correct tissue with vascular network

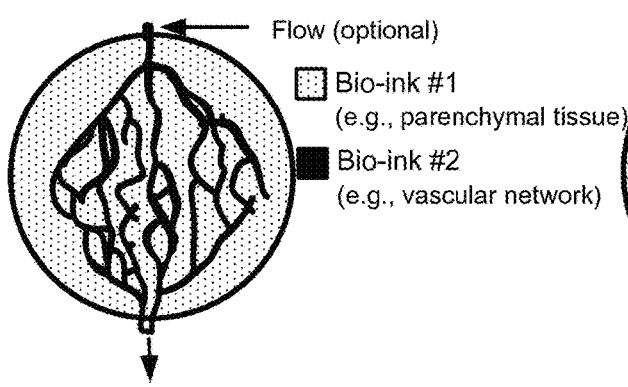

- Flow (optional)
- Bio-ink #1 (e.g., parenchymal tissue)
- Bio-ink #2 (e.g., vascular network)

(4) Zonal tissues (e.g., cortico-medullary junction)

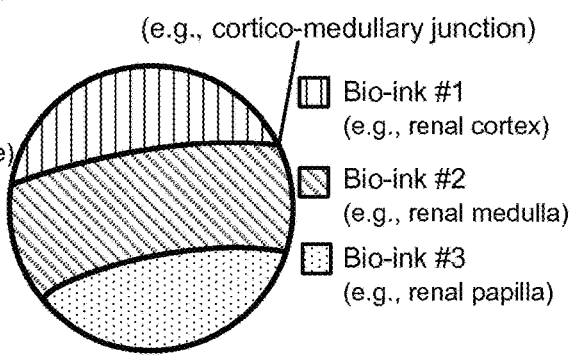

- Bio-ink #1 (e.g., renal cortex)
- Bio-ink #2 (e.g., renal medulla)
- Bio-ink #3 (e.g., renal papilla)

(5) Lobulated tissues

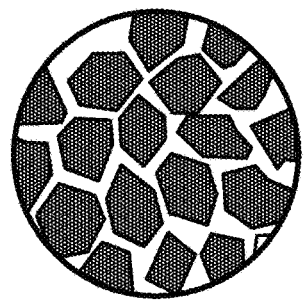

- Bio-ink #1 (e.g., liver lobules)
- Bio-ink #2 (e.g., stromal/vascular tissue)

(6) Perfused / Arrayed tissues

■ Component #1
□ Component #2

(7) Solid + liquid tissue / Liquid interfaces

■ Bio-ink #1
□ Bio-ink #2
▩ Component #3

(1) BARRIER TISSUE

- Barrier layer
- Interstitial layer
- Porous mesh or membrane
- Endothelial barrier layer (optional)

(2) Airway

- Airway epithelial cells
- Interstitial layer

(3) Renal tubule

- Renal tubular epithelial cells
- Interstitial layer
- Porous mesh or membrane
- Endothelial barrier (optional)

(4) Intestine

- Epithelial layer
- Submucosa
- Muscularis layer

(5) Mucosal surfaces

Mucosal layer
Underlying submucosal layer

(6) Mucocutaneous junction

Epithelium
Lamina Propria
Smooth Muscle
Mucosal surface | Epithelium / Skin
Epidermis
Dermis
Skeletal Muscle

ENGINEERED TISSUES FOR IN VITRO RESEARCH USES, ARRAYS THEREOF, AND METHODS OF MAKING THE SAME

CROSS REFERENCE TO RELATED APPLICATIONS

This application is a continuation of U.S. application Ser. No. 16/029,919, filed Jul. 9, 2018, which is a continuation of Ser. No. 13/612,768, filed Sep. 12, 2012, which claims the benefit of U.S. Application Ser. No. 61/533,757, filed Sep. 12, 2011, U.S. Application Ser. No. 61/533,753, filed Sep. 12, 2011, and U.S. Application Ser. No. 61/533,761, filed Sep. 12, 2011, all of which are hereby incorporated by reference in their entirety.

BACKGROUND OF THE INVENTION

The research and development cost of a new pharmaceutical compound is approximately $1.8 billion. See Paul, et al. (2010). How to improve R&D productivity: the pharmaceutical industry's grand challenge. *Nature Reviews Drug Discovery* 9(3):203-214. Drug discovery is the process by which drugs are discovered and/or designed. The process of drug discovery generally involves at least the steps of: identification of candidates, synthesis, characterization, screening, and assays for therapeutic efficacy. Despite advances in technology and understanding of biological systems, drug discovery is still a lengthy, expensive, and inefficient process with low rate of new therapeutic discovery.

SUMMARY OF THE INVENTION

There is a need for materials, tools, and techniques that substantially increase the number and quality of innovative, cost-effective new medicines, without incurring unsustainable R&D costs. Accordingly, the inventors describe herein engineered mammalian tissues and vascular wall segments, arrays thereof, and methods of making the same that have utility in tissue and organ engineering, in vitro assays, drug discovery, and other areas.

In one aspect, disclosed herein are living, three-dimensional tissue constructs comprising: at least one adherent cell type, the at least one adherent cell type cohered and fused to form a living, three-dimensional tissue construct, the tissue construct having a multi-layered architecture which is not a vascular tube, the tissue construct for in vitro use, provided that at least one component of the tissue construct was bioprinted. In some embodiments, the tissue construct is substantially free of any pre-formed scaffold at the time of bioprinting or at the time of use. In some embodiments, the tissue construct comprises at least one layer comprising a plurality of cell types, the cell types spatially arranged relative to each other to create a planar geometry. In some embodiments, the tissue construct comprises a plurality of layers, at least one layer compositionally or architecturally distinct from at least one other layer to create a laminar geometry. In some embodiments, the tissue construct further comprises non-adherent cell types. In some embodiments, the tissue construct is secured to a biocompatible surface. In further embodiments, the biocompatible surface is a porous membrane. In further embodiments, the biocompatible surface is coated with one of or more of the following: a biocompatible hydrogel, a protein, a chemical, a peptide, antibodies, or growth factors. In still further embodiments, the tissue construct is subjected to shear force, caused by fluid flow, on one or more sides. In some embodiments, the tissue construct is at least about 25 µm in its smallest dimension at the time of bioprinting. In some embodiments, the tissue construct is no greater than about 3 cm in its largest dimension at the time of bioprinting. In some embodiments, the tissue construct is for use in in vitro assays. In further embodiments, the tissue construct is for use in drug testing. In some embodiments, the adherent cells are differentiated cells. In other embodiments, the adherent cells are non-differentiated cells. In some embodiments, the adherent cells originated from a tissue selected from the group consisting of: liver, gastrointestinal, pancreatic, kidney, lung, tracheal, vascular, skeletal muscle, cardiac, skin, smooth muscle, connective tissue, corneal, genitourinary, breast, reproductive, endothelial, epithelial, fibroblast, neural, Schwann, adipose, bone, bone marrow, cartilage, pericytes, mesothelial, endocrine, stromal, lymph, blood, endoderm, ectoderm, and mesoderm. In some embodiments, the tissue construct is a vascular wall segment.

In another aspect, disclosed herein are arrays of living, three-dimensional tissue constructs, each tissue construct comprising: at least one adherent cell type, the at least one adherent cell type cohered and fused to form a living, three-dimensional tissue construct, each tissue construct having a multi-layered architecture, each tissue construct for in vitro use, provided that at least one component of each tissue construct was bioprinted. In some embodiments, each tissue construct is substantially free of any pre-formed scaffold at the time of bioprinting or the time of use. In some embodiments, the adherent cells are selected from the group consisting of: liver cells, gastrointestinal cells, pancreatic cells, kidney cells, lung cells, tracheal cells, vascular cells, skeletal muscle cells, cardiac cells, skin cells, smooth muscle cells, connective tissue cells, corneal cells, genitourinary cells, breast cells, reproductive cells, endothelial cells, epithelial cells, fibroblast, neural cells, Schwann cells, adipose cells, bone cells, bone marrow cells, cartilage cells, pericytes, mesothelial cells, cells derived from endocrine tissue, stromal cells, stem cells, progenitor cells, lymph cells, blood cells, endoderm-derived cells, ectoderm-derived cells, mesoderm-derived cells, and combinations thereof. In some embodiments, each tissue construct within the array is substantially similar. In other embodiments, one or more of the tissue constructs within the array is unique. In some embodiments, one or more individual tissues within the array represent human tissues selected from the group consisting of: blood or lymph vessel, muscle, uterus, nerve, mucous membrane, mesothelium, omentum, cornea, skin, liver, kidney, heart, trachea, lung, bone, bone marrow, adipose, connective, bladder, breast, pancreas, spleen, brain, esophagus, stomach, intestine, colon, rectum, ovary, prostate, endocrine tissue, endoderm, mesoderm, and ectoderm. In some embodiments, each tissue construct exists in a well of a biocompatible multi-well container. In further embodiments, the wells are coated with one of or more of the following: a biocompatible hydrogel, a protein, a chemical, a peptide, antibodies, or growth factors. In further embodiments, each tissue construct was placed onto a porous, biocompatible membrane within the wells of the container. In further embodiments, the container is compatible with an automated or semi-automated drug screening process. In some embodiments, each tissue construct is secured to a biocompatible surface. In further embodiments, the biocompatible surface is a porous membrane. In further embodiments, the biocompatible surface is coated with one of or more of the following: a biocompatible hydrogel, a protein, a chemical, a peptide, antibodies, or growth factors. In still further embodiments, each tissue construct is subjected to shear force, caused by fluid flow, on one or more sides. In some embodiments, each tissue construct within the array is maintained independently in culture. In other embodiments, two or more individual tissue constructs within the array exchange soluble factors. In some embodiments, the array is for use in in vitro assays. In further embodiments, the array is for use in drug testing. In some embodiments, at least one tissue within the array is a vascular wall segment.

In another aspect, disclosed herein are living, three-dimensional tissue constructs comprising: one or more layers, wherein each layer contains one or more cell types, the one or more layers cohered to form a living, three-dimensional tissue construct, the tissue construct characterized by having at least one of: at least one layer comprising a plurality of cell types, the cell types spatially arranged relative to each other to create a planar geometry; and a plurality of layers, at least one layer compositionally or architecturally distinct from at least one other layer to create a laminar geometry. In some embodiments, at least one component of the tissue construct was bioprinted. In further embodiments, the tissue construct is substantially free of any pre-formed scaffold at the time of bioprinting or at the time of use. In some embodiments, the tissue construct is for use in in vitro assays. In further embodiments, the tissue construct is for use in drug testing.

In another aspect, disclosed herein are methods for constructing a living, three-dimensional tissue construct comprising the steps of: bioprinting bio-ink comprising at least one adherent cell type into or onto a form; and fusing of the bio-ink into a living, three-dimensional tissue construct; provided that the tissue construct is for in vitro use and not a vascular tube. In some embodiments, the tissue construct is free of any pre-formed scaffold at the time of bioprinting or the time of use. In some embodiments, the form is bioprinted. In further embodiments, the form is bioprinted substantially contemporaneously with the bio-ink. In some embodiments, the method further comprises the step of dissolving the form.

In another aspect, disclosed herein are methods of constructing a living, three-dimensional tissue construct comprising the steps of: preparing one or more cohered multicellular aggregates comprising mammalian cells; placing said one or more cohered multicellular aggregates onto a support to form at least one of: at least one layer comprising a plurality of cell types, the cell types spatially arranged relative to each other to create a planar geometry; and a plurality of layers, at least one layer compositionally or architecturally distinct from at least one other layer to create a laminar geometry; and incubating said one or more multicellular aggregates to allow them to cohere and to form a living, three-dimensional tissue construct. In some embodiments, at least one component of the tissue construct was bioprinted. In further embodiments, the tissue construct is free of any pre-formed scaffold at the time of bioprinting or the time of use.

In another aspect, disclosed herein are methods of constructing an array of living, three-dimensional tissue constructs comprising the steps of: preparing cohered multicellular aggregates comprising mammalian cells; placing said cohered multicellular aggregates onto a biocompatible support; wherein said aggregates are spatially arranged in a form suitable for a tissue array; and incubating said multicellular aggregates to allow them to cohere and form an array of living, three-dimensional tissue constructs. In some embodiments, at least one component of each tissue construct was bioprinted. In further embodiments, each tissue construct is substantially free of any pre-formed scaffold at the time of bioprinting or the time of use.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 12 is a series of photomicrographs depicting analysis of multi-layered blood vessel wall segments with laminar geometry bioprinted on multi-well cell culture inserts under static and flow conditions. H&E staining of formalin-fixed paraffin-embedded tissues reveals well formed tissue constructs under both static (A) and flow/shear stress (D) culture conditions. Static culture of blood vessel constructs was sufficient to maintain proper cell arrangement which was characterized by a layer of CD31-positive EC at the laminar surface (C) and an α-SMA-positive SCM-rich media. Following exposure to 5 mL/min flow in a flow cell chamber, the CD31-positive EC layer appeared thicker (E) and the α-SMA-positive SMC-rich media appears to also be thicker and more well-organized, suggestive of a positive response to the biomechanical stimuli associated with shear stress and fluid flow.

FIG. 18 is a series of non-limiting examples of planar (A-C) and laminar (D-E) geometries, including combinations thereof (F) that are compatible with the methods of construction described herein, and reproduce architectural or spatial elements of native tissue architecture and biology.

FIG. 18A: Schematic diagrams of planar geometry examples (top view) of bioprinted tissues: (1) glandular tissue/cancer tissue, comprising bio-ink #1 (e.g., epithelial), bio-ink #2 (e.g., stromal) and a vascular component; (2) composite tissue/tissue interface, comprising bio-ink #1 (e.g., cartilage), bio-ink #2 (e.g., bone) and a third component (e.g., bone marrow); (3) architecturally-correct tissue with a vascular network, comprising bio-ink #1 (e.g., parenchymal tissue, including for example liver, pancreas, adipose, renal, muscle, skin, bone, cartilage, nervous, neural, urologic, cardiovascular, lymphoid, ocular, aural, or endocrine tissues, in any planar pattern) and bio-ink #2 (e.g., vascular network), with an optional flow through the bioprinted tissue; (4) zonal tissues, comprising bio-ink #1 (e.g., renal cortex), bio-ink #2 (e.g., renal medulla) and bio-ink #3 (e.g., renal papilla). The interface between bio-ink #1 and bio-ink #2 represents the cortico-medullary junction, for example; and (5) lobulated tissues, comprising bio-ink #1 (e.g., liver lobules), bio-ink #2 (e.g., stromal/vascular tissue). Note that each geometric "lobule" may also have spatially-directed architecture within it.

DETAILED DESCRIPTION OF THE INVENTION

Figure 1:
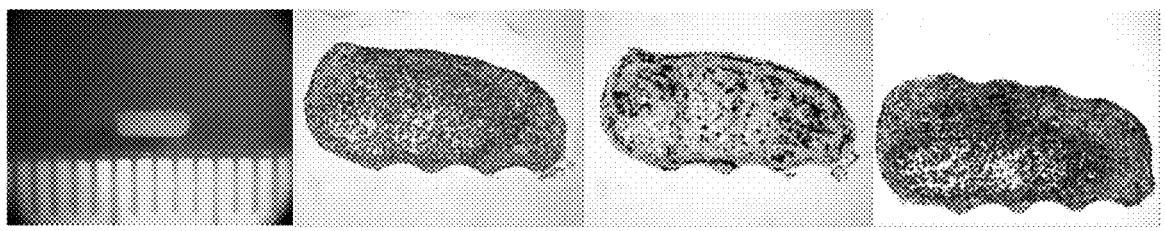
FIG. 1 depicts non-limiting examples of bioprinted vascular wall segments constructed with polytypic SMC: EC bio-ink in cylindrical format. Various staining conditions are shown to indicate distribution and position of cell types. (L to R) Bioprinted vessel wall constructs immediately after bioprinting in a 6-well plate. Hematoxylin and Eosin (H&E) staining of a construct after 5 days in culture demonstrating fusion of individual bio-ink particles into a contiguous structure and organization of cells at the periphery. CD31 staining of constructs generated with multicellular SMC: EC bio-ink shows organization of CD31-positive EC at the periphery and scattered CD31-positive cells within the wall. Trichrome staining of vessel wall constructs after 5 days shows robust collagen formation.

The invention relates to the field of regenerative medicine and tissue and/or organ engineering. More particularly, the invention relates to arrays of engineered mammalian tissues, engineered vascular wall segments, arrays thereof, and methods of fabrication.

Disclosed herein, in certain embodiments, are living, three-dimensional tissue constructs comprising: at least one adherent cell type, the at least one adherent cell type cohered and fused to form a living, three-dimensional tissue construct, the tissue construct having a multi-layered architecture which is not a vascular tube, the tissue construct for in vitro use, provided that at least one component of the tissue construct was bioprinted.

Also disclosed herein, in certain embodiments, are arrays of living, three-dimensional tissue constructs, each tissue construct comprising: at least one adherent cell type, the at least one adherent cell type cohered and fused to form a living, three-dimensional tissue construct, each tissue construct having a multi-layered architecture, each tissue construct for in vitro use, provided that at least one component of each tissue construct was bioprinted.

Also disclosed herein, in certain embodiments, are living, three-dimensional tissue constructs comprising: one or more layers, wherein each layer contains one or more cell types, the one or more layers cohered to form a living, three-dimensional tissue construct, the tissue construct characterized by having at least one of: at least one layer comprising a plurality of cell types, the cell types spatially arranged relative to each other to create a planar geometry; and a plurality of layers, at least one layer compositionally or architecturally distinct from at least one other layer to create a laminar geometry.

Also disclosed herein, in certain embodiments, are methods for constructing a living, three-dimensional tissue construct comprising the steps of: bioprinting bio-ink comprising at least one adherent cell type into or onto a form; and fusing of the bio-ink into a living, three-dimensional tissue construct; provided that the tissue construct is for in vitro use and not a vascular tube.

Also disclosed herein, in certain embodiments, are methods of constructing a living, three-dimensional tissue construct comprising the steps of: preparing one or more cohered multicellular aggregates comprising mammalian cells; placing said one or more cohered multicellular aggregates onto a support to form at least one of: at least one layer comprising a plurality of cell types, the cell types spatially arranged relative to each other to create a planar geometry; and a plurality of layers, at least one layer compositionally or architecturally distinct from at least one other layer to create a laminar geometry; and incubating said one or more multicellular aggregates to allow them to cohere and to form a living, three-dimensional tissue construct.

Also disclosed herein, in certain embodiments, are methods of constructing an array of living, three-dimensional tissue constructs comprising the steps of: preparing cohered multicellular aggregates comprising mammalian cells; placing said cohered multicellular aggregates onto a biocompatible support; wherein said aggregates are spatially arranged in a form suitable for a tissue array; and incubating said multicellular aggregates to allow them to cohere and form an array of living, three-dimensional tissue constructs.

Certain Definitions

Unless otherwise defined, all technical and scientific terms used herein have the same meaning as commonly understood by one of ordinary skill in the art to which this invention belongs.

As used in this specification and the appended claims, the singular forms "a," "an," and "the" include plural references unless the context clearly dictates otherwise. Thus, for example, references to "a nucleic acid" includes one or more nucleic acids, and/or compositions of the type described herein which will become apparent to those persons skilled in the art upon reading this disclosure and so forth. Any reference to "or" herein is intended to encompass "and/or" unless otherwise stated.

As used herein, "array" means a scientific tool including an association of multiple elements spatially arranged to allow a plurality of tests to be performed on a sample, one or more tests to be performed on a plurality of samples, or both.

As used herein, "assay" means a procedure for testing or measuring the presence or activity of a substance (e.g., a chemical, molecule, biochemical, protein, hormone, or drug, etc.) in an organic or biologic sample (e.g., cell aggregate, tissue, organ, organism, etc.).

As used herein, "biocompatible" means posing limited risk of injury or toxicity to cells. As presented in the specification and claims, "biocompatible multi-well containers" and "biocompatible membranes" pose limited risk of injury or toxicity to mammalian cells, but the definition does not extend to imply that these biocompatible elements could be implanted in vivo into a mammal.

As used herein, "bioprinting" means utilizing three-dimensional, precise deposition of cells (e.g., cell solutions, cell-containing gels, cell suspensions, cell concentrations, multicellular aggregates, multicellular bodies, etc.) via methodology that is compatible with an automated or semi-automated, computer-aided, three-dimensional prototyping device (e.g., a bioprinter).

As used herein, "blood vessel" means a singular simple or branched tubular structure having a smooth muscle cell-comprising wall and endothelial cells lining the lumen, and having an internal diameter greater than 100 µm, and not existing as a component of three-dimensional tissue construct that comprises non-blood vessel tissue.

As used herein, "cohere," "cohered," and "cohesion" refer to cell-cell adhesion properties that bind cells, cell aggregates, multicellular aggregates, multicellular bodies, and/or layers thereof. The terms are used interchangeably with "fuse," "fused," and "fusion."

As used herein, "laminar" means a multi-layered bioprinted tissue in which two or more planar layers are combined to increase the overall thickness of the tissue in the z-plane. In some embodiments, each planar layer is substantially similar in architecture and/or composition. In other embodiments, each planar layer is substantially distinct in architecture and/or composition. See, e.g., FIGS. 18A-F.

As used herein, "multi-layered" means being comprised of two or more layers of tissue, wherein each tissue layer is one or more cell-layers in thickness. In some embodiments, layers of tissue are deposited one at a time. In other embodiments, multiple layers are deposited simultaneously. Optionally, each layer is comprised of multiple cell types. Further, the multiple cell types within each layer are optionally arranged relative to each other in a spatially-defined architecture in the x-y planes (i.e., horizontal planes). Furthermore, addition of layers in the z-plane (i.e., vertical plane), in some cases, results in controlled spatial positioning of the cells within the layers relative to each other so that a spatially-defined architecture is continued in the z-plane.

As used herein, "planar" means a layer of multicellular bioprinted tissue in which multiple bio-ink compositions and/or void spaces are spatially arranged into a defined pattern relative to each other within the x-y plane of the tissue layer. See, e.g., FIGS. 18A-F.

As used herein, "scaffold" refers to synthetic scaffolds such as polymer scaffolds and porous hydrogels, non-synthetic scaffolds such as pre-formed extracellular matrix layers, dead cell layers, and decellularized tissues, and any other type of pre-formed scaffold that is integral to the physical structure of the engineered tissue and/or organ and not able to be removed from the tissue and/or organ without damage/destruction of said tissue and/or organ. In further embodiments, decellularized tissue scaffolds include decellularized native tissues or decellularized cellular material generated by cultured cells in any manner; for example, cell layers that are allowed to die or are decellularized, leaving behind the ECM they produced while living. The term "scaffoldless," therefore, is intended to imply that scaffold is not an integral part of the engineered tissue at the time of use, either having been removed or remaining as an inert component of the engineered tissue. "Scaffoldless" is used interchangeably with "scaffold-free" and "free of pre-formed scaffold."

As used herein, "subject" means any individual, which is a human, a non-human animal, any mammal, or any vertebrate. The term is interchangeable with "patient," "recipient" and "donor."

As used herein, "tissue" means an aggregate of cells. Examples of tissues include, but are not limited to, connective tissue (e.g., areolar connective tissue, dense connective tissue, elastic tissue, reticular connective tissue, and adipose tissue), muscle tissue (e.g., skeletal muscle, smooth muscle and cardiac muscle), genitourinary tissue, gastrointestinal tissue, pulmonary tissue, bone tissue, nervous tissue, and epithelial tissue (e.g., simple epithelium and stratified epithelium), endoderm-derived tissue, mesoderm-derived tissue, and ectoderm-derived tissue.

Tissue Engineering

Tissue engineering is an interdisciplinary field that applies and combines the principles of engineering and life sciences toward the development of biological substitutes that restore, maintain, or improve tissue function through augmentation, repair, or replacement of an organ or tissue. The basic approach to classical tissue engineering is to seed living cells into a biocompatible and eventually biodegradable environment (e.g., a scaffold), and then culture this construct in a bioreactor so that the initial cell population expands further and matures to generate the target tissue upon implantation. With an appropriate scaffold that mimics the biological extracellular matrix (ECM), the developing tissue, in some cases, adopts both the form and function of the desired organ after in vitro and in vivo maturation. However, achieving high enough cell density with a native tissue-like architecture is challenging due to the limited ability to control the distribution and spatial arrangement of the cells throughout the scaffold. These limitations often result in tissues or organs with poor mechanical properties and/or insufficient function. Additional challenges exist with regard to biodegradation of the scaffold, entrapment of residual polymer, and industrial scale-up of manufacturing processes. Scaffoldless approaches have been attempted. Current scaffoldless approaches are subject to several limitations:

Complex planar and/or laminar geometries, such as multi-layered structures wherein one or more layers is compositionally or architecturally distinct from other layers or wherein one or more layers comprise multiple cell types in spatially-defined positions relative to each other, often require definitive, high-resolution placement of cell types within a specific architecture to reproducibly achieve a native tissue-like outcome.

Scale and geometry are limited by diffusion and/or the requirement for functional vascular networks for nutrient supply.

The viability of the tissues is, in some cases, compromised by confinement material that limits diffusion and restricts the cells' access to nutrients.

Disclosed herein, in certain embodiments, are engineered mammalian tissues, engineered vascular wall segments, arrays thereof, and methods of fabrication. The tissue engineering methods disclosed herein have the following advantages:

They are capable of producing cell-comprising tissues and/or organs.

They mimic the environmental conditions found within the development, homeostasis, and/or pathogenesis of natural tissues by re-creating native tissue-like intercellular interactions.

They optionally achieve living, three-dimensional tissues and compound tissues with a broad array of complex topologies and geometries (e.g., multilayered structures, segments, sheets, tubes, sacs, etc.).

They are compatible with automated or semi-automated means of manufacturing and are scalable.

Bioprinting enables improved methods of generating micro-scale tissue analogues including those useful for in vitro assays (see below).

Bioprinting

In some embodiments, at least one component of the engineered tissues, including vascular wall segments, and arrays thereof is bioprinted. In further embodiments, bioprinted constructs are made with a method that utilizes a rapid prototyping technology based on three-dimensional, automated, computer-aided deposition of cells, including cell solutions, cell suspensions, cell-comprising gels or pastes, cell concentrations, multicellular bodies (e.g., cylinders, spheroids, ribbons, etc.), and, optionally, confinement material onto a biocompatible surface (e.g., composed of hydrogel and/or a porous membrane) by a three-dimensional delivery device (e.g., a bioprinter). As used herein, in some embodiments, the term "engineered," when used to refer to tissues and/or organs means that cells, cell solutions, cell suspensions, cell-comprising gels or pastes, cell concentrates, multicellular aggregates, and layers thereof are positioned to form three-dimensional structures by a computer-aided device (e.g., a bioprinter) according to a computer script. In further embodiments, the computer script is, for example, one or more computer programs, computer applications, or computer modules. In still further embodiments, three-dimensional tissue structures form through the post-printing fusion of cells or multicellular bodies which, in some cases, is similar to self-assembly phenomena in early morphogenesis.

While a number of methods are available to arrange cells, multicellular aggregates, and/or layers thereof on a biocompatible surface to produce a three-dimensional structure including manual placement, positioning by an automated, computer-aided machine such as a bioprinter is advantageous. Advantages of delivery of cells or multicellular bodies with this technology include rapid, accurate, and reproducible placement of cells or multicellular bodies to produce constructs exhibiting planned or pre-determined orientations or patterns of cells, multicellular aggregates and/or layers thereof with various compositions. Advantages also include assured high cell density, while minimizing cell damage.

In some embodiments, the method of bioprinting is continuous and/or substantially continuous. A non-limiting example of a continuous bioprinting method is to dispense bio-ink (i.e., cells, cells combined with an excipient or extrusion compound, or aggregates of cells) from a bioprinter via a dispense tip (e.g., a syringe, needle, capillary tube, etc.) connected to a reservoir of bio-ink. In further non-limiting embodiments, a continuous bioprinting method is to dispense bio-ink in a repeating pattern of functional units. In various embodiments, a repeating functional unit has any suitable geometry, including, for example, circles, squares, rectangles, triangles, polygons, and irregular geometries, thereby resulting in one or more tissue layers with planar geometry achieved via spatial patterning of distinct bio-inks and/or void spaces. In further embodiments, a repeating pattern of bioprinted function units comprises a layer and a plurality of layers are bioprinted adjacently (e.g., stacked) to form an engineered tissue or organ with laminar geometry. In various embodiments, 2, 3, 4, 5, 6, 7, 8, 9, 10, 11, 12, 13, 14, 15, or more layers are bioprinted adjacently (e.g., stacked) to form an engineered tissue or organ. In further embodiments, one or more layers of a tissue with laminar geometry also has planar geometry.

Figure 6:
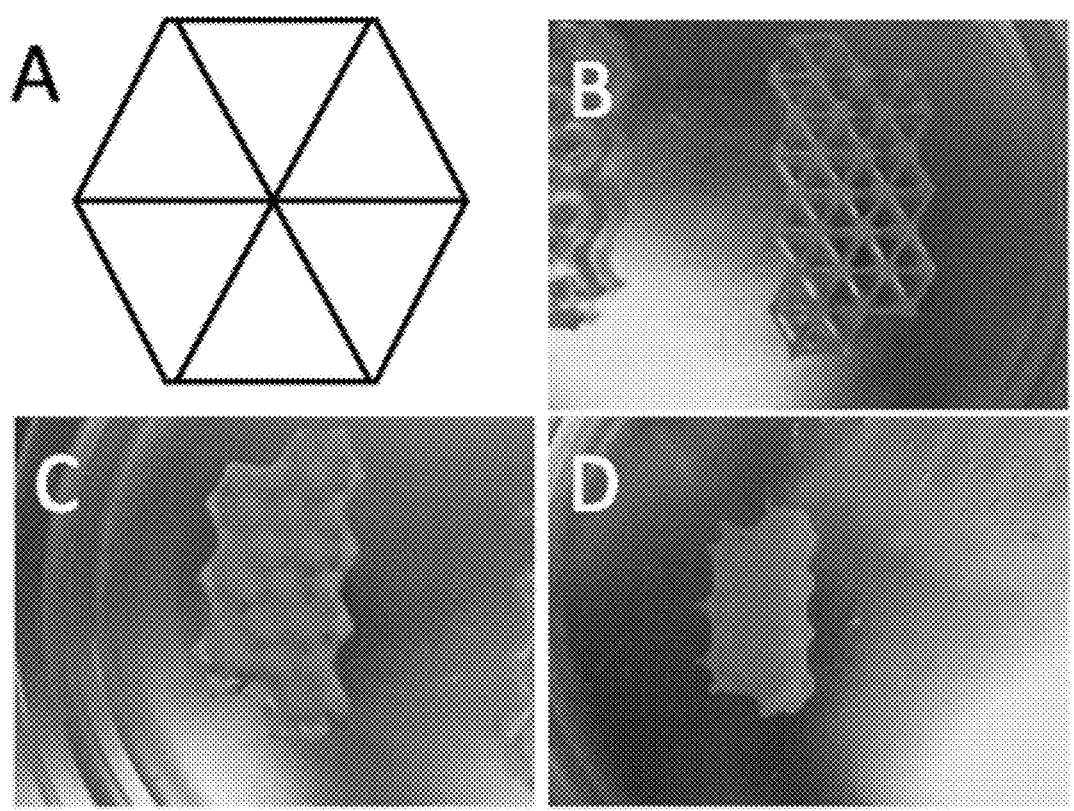
FIG. 6 is a macroscopic image depicting a non-limiting example of an engineered liver tissue, in this case, a multi-layered liver tissue bioprinted using a continuous deposition mechanism using bio-ink composed of multiple liver cell types encapsulated in a water-soluble extrusion compound (e.g., PF-127). (A) shows a schematic diagram of a single functional unit highlighting the planar geometry created by patterning bio-ink and negative space; (B) shows tessellated, bioprinted functional units bioprinted with PF-127 containing $2 \times 10^8$ cells; (C) and (D) show the construct after application of media and dissolution of the extrusion compound, 20 minutes and 18 hours after application of media to the structure, respectively; note retention of the planar geometry over time.
Figure 17:
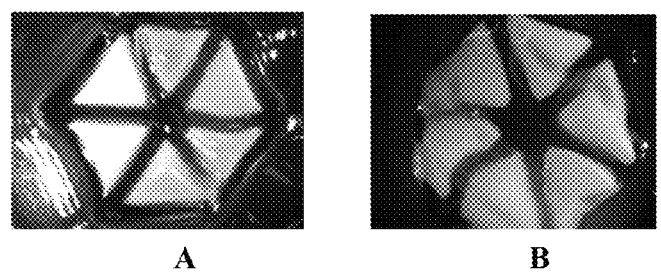
FIG. 17 is a pair of macroscopic photographs depicting co-molded functional liver tissue microstructure formed by continuous deposition bioprinting of a patterned 6-layer hexagon of PF-127 with bioprinting of cell paste into each triangle (A), followed by dissolution of PF-127 border (B). Dissolution of PF-127 border after media addition allows for distinct regions to be created and additional cells types and complexity to be generated (B).

In some embodiments, a bioprinted functional unit repeats in a tessellated pattern. A "tessellated pattern" is a plane of figures that fills the plane with no overlaps and no gaps. FIG. 6A shows an example of a functional unit that is optionally repeated to produce the tessellation pattern depicted in FIGS. 6B-D and 7. Advantages of continuous and/or tessellated bioprinting includes, by way of non-limiting example, increased productivity of bioprinted tissue. Another non-limiting, exemplary advantage is eliminating the need to align the bioprinter with previously deposited elements of bio-ink. In some embodiments, continuous bioprinting facilitates printing larger tissues from a large reservoir of bio-ink, optionally using a syringe mechanism. Continuous bioprinting is also a convenient way to co-print spatially-defined boundaries, using an extrusion compound, a hydrogel, a polymer, bio-ink, or any printable material that is capable of retaining its shape post-printing; wherein the boundaries that are created are optionally filled in via the bioprinting of a one or more bio-inks, thereby creating a mosaic tissue with spatially-defined planar geometry, see for example, the embodiment illustrated in FIG. 17.

In some embodiments, methods in continuous bioprinting involve optimizing and/or balancing parameters such as print height, pump speed, robot speed, or combinations thereof independently or relative to each other. In one example, the bioprinter head speed for deposition was 3 mm/s, with a dispense height of 0.5 mm for the first layer and dispense height was increased 0.4 mm for each subsequent layer. In some embodiments, the dispense height is approximately equal to the diameter of the bioprinter dispense tip. Without limitation a suitable and/or optimal dispense distance does not result in material flattening or adhering to the dispensing needle. In various embodiments, the bioprinter dispense tip has an inner diameter of about, 20, 50, 100, 150, 200, 250, 300, 350, 400, 450, 500, 550, 600, 650, 700, 750, 800, 850, 900, 950, 1000 µm, or more, including increments therein. In various embodiments, the bio-ink reservoir of the bioprinter has a volume of about 0.05, 0.1, 0.5, 1, 2, 3, 4, 5, 6, 7, 8, 9, 10, 15, 20, 25, 30, 35, 40, 45, 50, 55, 60, 65, 70, 75, 80, 85, 90, 95, 100 cubic centimeters, or more, including increments therein. The pump speed is, in some cases, suitable and/or optimal when the residual pressure build-up in the system is low. Favorable pump speeds, in some cases, depend on the ratio between the cross-sectional areas of the reservoir and dispense needle with larger ratios requiring lower pump speeds. In some embodiments, a suitable and/or optimal print speed enables the deposition of a uniform line without affecting the mechanical integrity of the material.

The inventions disclosed herein include business methods. In some embodiments, the speed and scalability of the techniques and methods disclosed herein are utilized to design, build, and operate industrial and/or commercial facilities for production of engineered tissues and/or organs for implantation or use in generation of cell-based tools for research and development, such as in vitro assays. In further embodiments, the engineered tissues and/or organs and arrays thereof are produced, stored, distributed, marketed, advertised, and sold as, for example, cellular arrays (e.g., microarrays or chips), tissue arrays (e.g., microarrays or chips), and kits for biological assays and high-throughput drug screening. In other embodiments, the engineered tissues and/or organs and arrays thereof are produced and utilized to conduct biological assays and/or drug screening as a service.

Engineered Tissues

Figure 10:
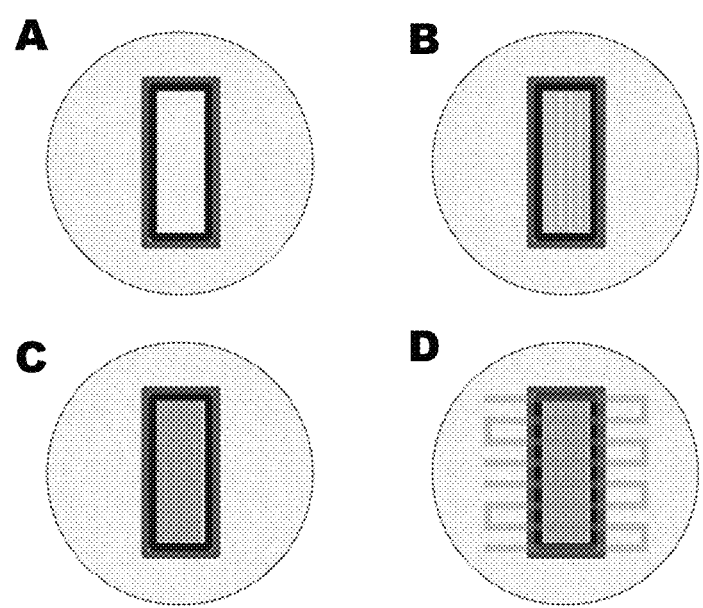
FIG. 10 is a non-limiting schematic diagram of a bioprinted human lung tissue construct with laminar geometry, depicting steps for fabrication. A double-walled box using hydrogel cylinders is bioprinted on the cell culture insert membrane (A). Next, NHLF: EC bio-ink cylinder is then bioprinted inside the box (B). The SAEC suspension is the bioprinted on top of the NHLF-EC tissue (C). The bioprinted lung tissue construct is constrained with a top layer of hydrogel cylinders (D) and the construct submerged in complete media for culture.
Figure 11:
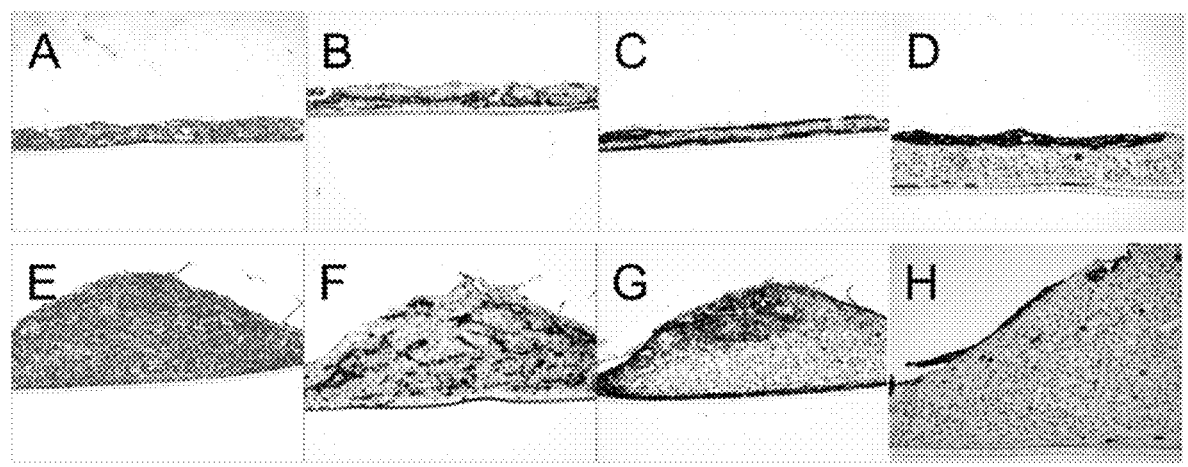
FIG. 11 is a series of photomicrographs depicting characterization of bioprinted human lung tissues. H&E staining of formalin-fixed tissue sections from bioprinted lung tissue after 12d in culture reveals tissue fusion (A). CD31-postive EC are found organized throughout (B) and α-SMA-positive NHLF (C) localized at the periphery of the construct. Cytokeratin 19-positive SAEC are found only at the apical surface of the tissue (D). Stimulation with 10 ng/ml IL-13 results in thickening of the tissue (E) and increased organization of CD31-postive EC within the construct wall (F). Cytokine stimulation also increases the number of a-SMA positive NHLF found in the sub-epithelial zone (G). CK19-positive SAEC remain confined to the apical surface (H).

Disclosed herein, in some embodiments, are living, three-dimensional tissue constructs comprising at least one adherent cell type, wherein the at least one adherent cell type is cohered and fused to form a tissue construct with a multi-layered architecture. In further embodiments, at least one component of the tissue construct was bioprinted. In some embodiments, the tissues are vascular wall segments (see, e.g., Example 16 and FIGS. 12 and 13). Therefore, also disclosed herein, in some embodiments, are engineered vascular wall segments comprising: smooth muscle cells; and optionally, fibroblasts and/or endothelial cells; wherein the cells are cohered to one another; wherein the vascular wall segment was bioprinted and is non-tubular. In other embodiments, the tissues are airway analogues (see, e.g., Example 15 and FIGS. 10 and 11). In some embodiments, the airway analogues comprise: pulmonary fibroblasts and optionally, smooth muscle cells and/or endothelial cells, wherein at least one surface of the tissue is layered with small airway epithelial cells. In other embodiments, the tissues are liver analogues (see, e.g., Examples 13 and 19 and FIGS. 6A-D, 7, and 17A-B). In further embodiments, the liver tissue analogues comprise: hepatocytes or hepatocyte-like cells and optionally bile duct epithelial cells and optionally, non-parenchymal cell types including, but not limited to, stellate cells, endothelial cells, kupffer cells, immune cells, or myofibroblasts.

Also disclosed herein, in certain embodiments, are engineered tissues comprising cohered, mammalian cells, and further comprising one or more layers of mammalian cells, wherein at least one component of the tissue was bioprinted. In some embodiments, one or more of the tissue layers is characterized by a planar geometry, wherein multiple cell types or bio-ink types and/or void spaces exist in spatially-defined positions in the x-y planes. In some embodiments, the tissues are multi-layered wherein at least one of the layers is architecturally or compositionally distinct from the other layers, giving the tissue a characteristic laminar geometry. In further embodiments, the layers are of similar thickness in the z-plane. In still further embodiments, the layers are of variable thickness in the z-plane. In further embodiments, any single layer is one cell layer in thickness. In some embodiments, the tissues are vascular wall segments. Therefore, also disclosed herein, in certain embodiments, are engineered vascular wall segments comprising cohered smooth muscle cells, and a layer of endothelial cells on one or more surfaces, a layer of fibroblasts on one or more surfaces, or both, wherein at least one component of said vascular wall segment was bioprinted; and wherein said vascular wall segment is non-tubular. In other embodiments, the tissues are airway analogues. In some embodiments, the airway analogues comprise: pulmonary fibroblasts and optionally, smooth muscle cells and/or endothelial cells, wherein at least one surface of the tissue is layered with small airway epithelial cells. In other embodiments, the tissues are liver analogues. In further embodiments, the liver tissue analogues comprise: hepatocytes or hepatocyte-like cells and optionally bile duct epithelial cells and optionally, non-parenchymal cell types including, but not limited to, stellate cells, endothelial cells, kupffer cells, immune cells, or myofibroblasts.

In some embodiments, the engineered tissues, including vascular wall segments, are bioprinted, a methodology described herein. In further embodiments, at least one component of the engineered tissue is bioprinted. In further embodiments, the bioprinted component comprises cohered smooth muscle cells. In still further embodiments, additional components of the tissue are bioprinted. In further embodiments, the additional bioprinted layers comprise fibroblasts and/or endothelial cells. In further embodiments, the tissues are free of any pre-formed scaffold as described further herein at the time of manufacture or at the time of use. In some embodiments, as a result of being fabricated by tissue engineering techniques, including bioprinting, the tissues of the present invention are further distinguished from tissues developed in vivo, as part of an organism. In some embodiments, one layer of the engineered tissue consists of interstitial tissue, comprising various cell types such as fibroblasts, smooth muscle cells, myofibroblasts, pericytes, and endothelial cells. In further embodiments, the interstitial tissue is layered on one or more surfaces with a second tissue type comprising generic or tissue-specific endothelial or epithelial cells. In still further embodiments, the second tissue layer is contiguous and serves as a barrier for passage of molecules to the underlying interstitial tissue layer.

Figure 2A:
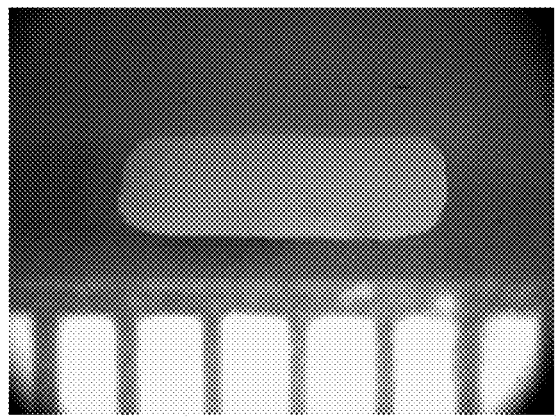
FIG. 2a is a macroscopic image depicting a non-limiting example of three-dimensional bioprinted vascular wall segments 24 hours post printing. The patch was constructed with polytypic bio-ink cylinders of multicellular HASMC: HAEC at a ratio of 85:15.
Figure 2B:
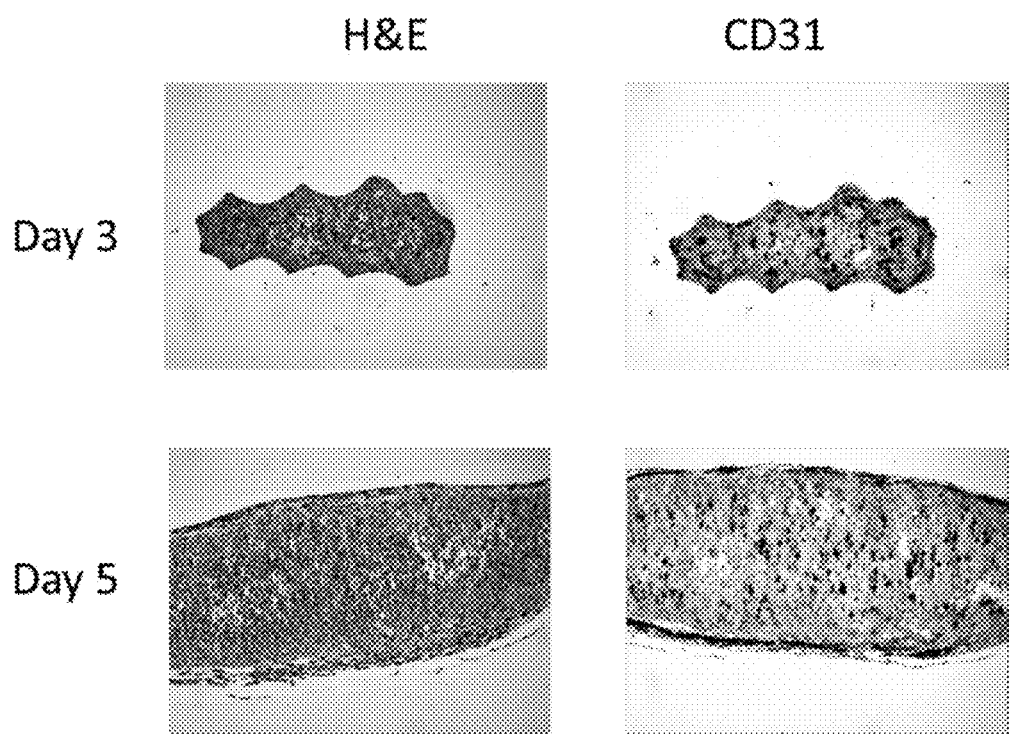
FIG. 2b depicts histology images of bioprinted patches in non-limiting examples of bioprinted vascular wall segments constructed with bio-ink comprised of multicellular HASMC:HAEC at a ratio of 85:15. HAEC stain positive for CD31.

In some embodiments, the engineered tissues, including vascular wall segments, include any type of mammalian cell. In various further embodiments, the tissues, including vascular wall segments, include 1, 2, 3, 4, 5, 6, 7, 8, 9, 10, 11, 12, 13, 14, 15, 16, 17, 18, 19, 20 or more cell types. In some embodiments, the tissues include only smooth muscle cells. In some embodiments, the tissues include smooth muscle cells and endothelial cells. Example 3 demonstrates fabrication of polytypic cylindrical bio-ink consisting of human aortic smooth muscle cells and human aortic endothelial cells while Example 4 demonstrates bioprinting and fusion of such cylinders to form blood vessel wall segments (see e.g., FIGS. 1, 2a, and 2b). Example 7 demonstrates fabrication of polytypic cylindrical bio-ink consisting of smooth muscle cells and endothelial cells cultured from the stromal vascular fraction of human lipoaspirate while Example 8 demonstrates bioprinting and fusion of such cylinders to form blood vessel wall segments. In other embodiments, the tissues include smooth muscle cells and fibroblasts. In yet other embodiments, the tissues include smooth muscle cells, endothelial cells, and fibroblasts. Example 5 demonstrates fabrication of polytypic cylindrical bio-ink consisting of human aortic smooth muscle cells, human dermal fibroblasts, and human aortic endothelial cells while Example 6 demonstrates bioprinting and fusion of such cylinders to form blood vessel wall segments. In some embodiments, the cells of the engineered tissues, including vascular wall segments are "cohered" or "adhered" to one another. In further embodiments, cohesion or adhesion refers to cell-cell adhesion properties that bind cells, multicellular aggregates, multicellular bodies, and/or layers thereof.

In some embodiments, the engineered tissues, including vascular wall segments, include one or more layers of cells on one or more surfaces. In further embodiments, one or more layers of cells are on one or more surfaces of the cohered smooth muscle cells. In further various embodiments, there are 1, 2, 3, 4, 5, 6, 7, 8, 9, 10 or more layers of cells on one or more surfaces of the cohered smooth muscle cells. In still further various embodiments, there is at least one layer of cells on 1, 2, 3, 4 or more surfaces of the cohered smooth muscle cells, creating a laminar geometry in the engineered tissue. In further embodiments, one or more of the layers is characterized by having a planar geometry. In still further embodiments, multiple layers of the engineered tissue have a planar geometry; wherein the planar geometries are variable among layers or are the same. In still further embodiments, planar geometries (x-y planes) in individual layers are aligned in the z-plane during fabrication so that additional geometry is created in the z-plane in the composite tissue (see, e.g., embodiments presented in FIGS. 18D-F).

In some embodiments, a layer of tissue comprises a monolayer of cells. In further embodiments, the monolayer is confluent. In other embodiments, the monolayer is not confluent. In some embodiments, a layer of cells comprises one or more sheets of cells. In various embodiments, a sheet of cells is about 1, 2, 3, 4, 5, 6, 7, 8, 9, 10, 20, 30, 40, 50, 60, 70, 80, 90, 100 or more cells thick, including increments therein. In other various embodiments, a sheet of cells is about 3, 5, 10, 15, 20, 25, 30, 35, 40, 45, 50, 55, 60, 65, 70, 75, 80, 85, 90, 95, 100, 125, 150, 175, 200, 225, 250, 275, 300, 325, 350, 375, 400, 425, 450, 475, 500 or more μm thick, including increments therein. In some embodiments, a layer of tissue comprises fused aggregates of cells. In further embodiments, prior to fusion, the aggregates of cells have, by way of non-limiting examples, a defined shape and/or architecture, being substantially spherical, elongate, substantially cylindrical and ribbon-like shape. In various embodiments, fused aggregates of cells form a layer about 10, 15, 20, 25, 30, 35, 40, 45, 50, 55, 60, 65, 70, 75, 80, 85, 90, 95, 100, 125, 150, 175, 200, 225, 250, 275, 300, 325, 350, 375, 400, 425, 450, 475, 500 or more μm thick, including increments therein.

In some embodiments, the one or more layers include any type of mammalian cell. In various further embodiments, each layer includes 1, 2, 3, 4, 5, 6, 7, 8, 9, 10, 11, 12, 13, 14, 15, 16, 17, 18, 19, 20 or more cell types. In some embodiments, the engineered tissues, including vascular wall segments, include one or more layers of endothelial cells on one or more surfaces. Example 9 demonstrates construction of vascular wall segments by bioprinting a layer of vascular media tissue comprising cylindrical smooth muscle cell bio-ink, followed by application of a second layer of endothelial cells to the top surface, achieved by bioprinting a cell concentrate directly onto the SMC construct to generate a laminar geometry that recapitulates the media and intima of the blood vessel wall. Example 10 demonstrates construction of vascular wall segments by bioprinting of cylindrical bio-ink comprising human aortic smooth muscle cells followed by application of a layer of endothelial cells to the top surface, achieved by deposition of specifically positioned droplets of endothelial cells onto the SMC construct. In some embodiments, the engineered tissues, including vascular wall segments, include one or more layers of fibroblasts on one or more surfaces.

In some embodiments, the engineered tissues, including vascular wall segments, include one or more layers of endothelial cells on one or more surfaces and one or more layers of fibroblasts on one or more surfaces. In further embodiments, the one or more layers of endothelial cells are on the same surfaces as the one or more layers of fibroblasts. In other embodiments, the one or more layers of endothelial cells are on surfaces distinct from surfaces with one or more layers of fibroblasts. In further embodiments, one or more of the layers within the multi-layered architecture is characterized further by having planar geometry.

Figure 4A:
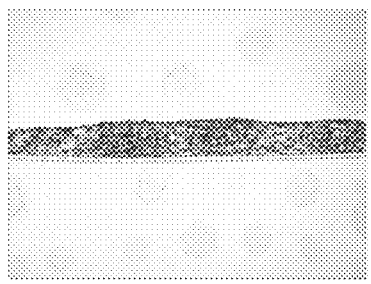
FIG. 4a depicts non-limiting examples of bioprinted vascular wall segments constructed with HASMC bioprinted on top of a first layer of human dermal fibroblasts (HDFa) and subsequently layered with HAEC, creating a tri-layered laminar architecture. Depicted are histology images of tri-layered bioprinted patches. Patch made using HASMC bio-ink printed on top of a confluent layer of HDFa on a Transwell® membrane, and finally top seeded with HAEC to form a third layer. HAEC cells stain positive for CD31. HASMC stain positive for alpha SMA. Timepoint=4 days post printing.
Figure 4A:
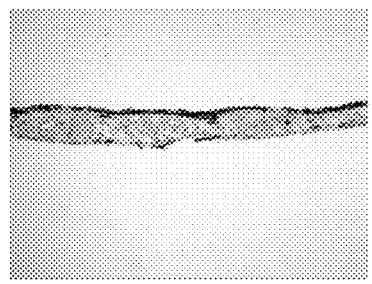
Figure 4A:
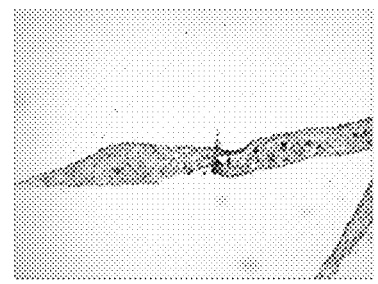
Figure 4B:
FIG. 4b is a macroscopic image depicting a non-limiting example of HASMC bio-ink bioprinted within a co-printed NovoGel™ containment window and layered with HAEC, but without a third layer of NovoGel™ lattice (e.g., mesh) on top. Depicted is a macroscopic image of three-dimensional bioprinted patch. Shown is a 2× magnification image of cylindrical HASMC bio-ink shown immediately after bioprinting. HAECs were bioprinted on top of the HASMC patch. A top layer of NovoGel™ mesh was not utilized on this construct.
Figure 12:
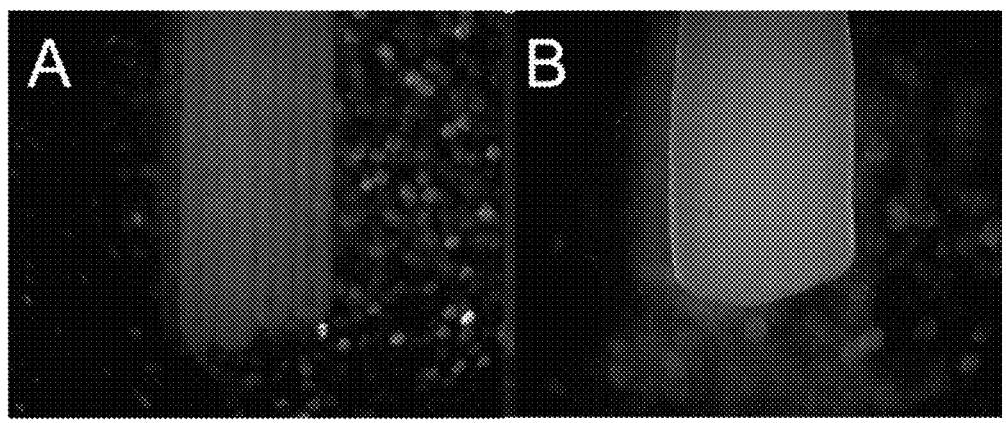
FIG. 12 is a pair of macroscopic photographs depicting a bioprinted vascular wall segment immediately after bioprinting (A) and following 24 hours of incubation in media (B). Bi-layered blood vessel wall segments were bioprinted with SMC or SMC: Fb bio-ink and highly-concentrated EC cell suspensions. Immediately after bioprinting (A) individual bio-ink cylinders are identifiable. Following 24 hours of incubation in media, the individual bio-ink cylinders and layer of EC have completely fused to form a single contiguous construct (B).
Figure 13:
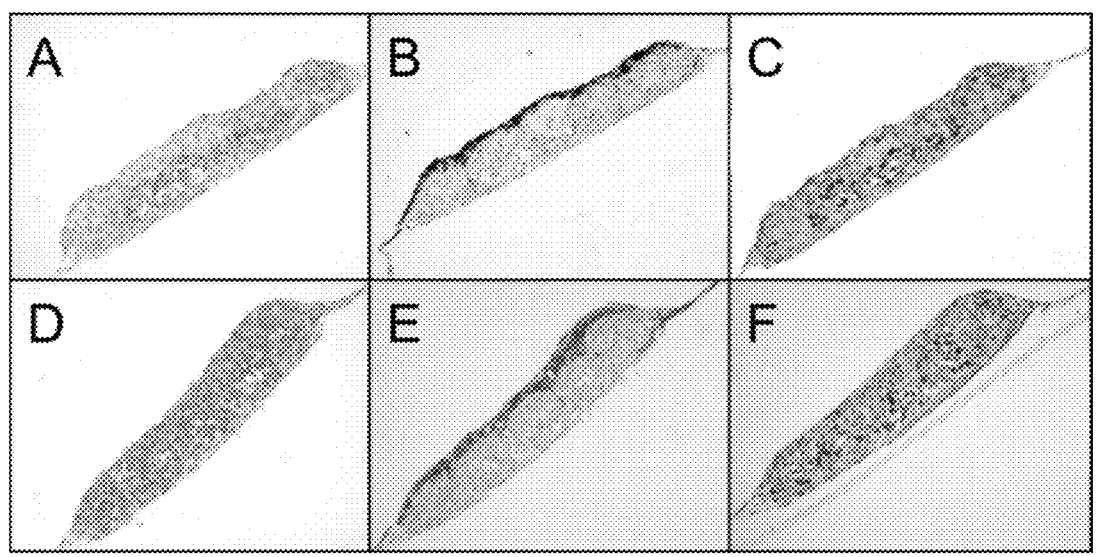

Example 11 demonstrates construction of vascular wall segments by bioprinting cylindrical bio-ink comprising human aortic smooth muscle cells directly onto a first layer of fibroblasts, followed by application of a third layer comprising endothelial cells to the top surface, thereby creating a tri-layered laminar geometry wherein each layer is compositionally distinct and of variable thickness and architecture (see, e.g., FIG. 12). The layer of endothelial cells is applied by deposition of specifically positioned droplets of endothelial cell suspension onto the construct. The procedures of Example 11 result in a tri-layered tissue comprising cohered smooth muscle cells, a layer of fibroblasts on one surface of the smooth muscle cells, and a layer of fibroblasts on an opposing surface of the smooth muscle cells. The cells within each layer are cohered to each other, and the cells positioned at the interface between layers are also cohered, thereby bonding the individual layers together by cellular interactions (see, e.g., FIGS. 4a and 4b).

The engineered tissues, including vascular wall segments, in various embodiments, are any suitable size. In some embodiments, the size of bioprinted tissues, including vascular wall segments, change over time. In further embodiments, a bioprinted tissue shrinks or contracts after bioprinting due to, for example, cell migration, cell death, intercellular interactions, contraction, or other forms of shrinkage. In other embodiments, a bioprinted tissue grows or expands after bioprinting due to, for example, cell migration, cell growth and proliferation, production of extracellular matrix or other cell-produced components of native tissue, cell/tissue maturation or other forms of expansion.

In some embodiments, the physical dimensions of the engineered tissues, including vascular wall segments, are limited by the capacity for nutrients, including oxygen, to diffuse into the interior of the construct. In various embodiments, the engineered tissues, including vascular wall segments, are at least about 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 550, 600, 650, 700, 750, 800, 850, 900, 950, or 1000 μm in their smallest dimension at the time of bioprinting. In various embodiments, the engineered tissues, including vascular wall segments, are at least about 0.25, 0.5, 0.75, 1.0, 1.25, 1.5, 1.75, 2.0, 2.25, 2.5, 2.75, 3.0, 3.25, 3.5, 3.75, 4.0, 4.25, 4.5, 4.75, or 5.0 mm in their smallest dimension at the time of bioprinting. In further embodiments, the engineered tissues, including vascular wall segments, are between about 25 μm and about 500 μm in their smallest dimension at the time of bioprinting. In other embodiments, the engineered tissues, including vascular wall segments, are less than 3 cm in the largest dimension at the time of fabrication.

The engineered tissues, including vascular wall segments, in various embodiments, are any suitable shape. In some embodiments, the shape is selected to mimic a particular natural tissue or organ. In further embodiments, the shape is selected to mimic a particular pathology, condition, or disease state. In some embodiments, the engineered tissues, including vascular wall segments, have a shape that is substantially planar. In further embodiments, planar tissues have any suitable planar geometry including, by way of non-limiting examples, square, rectangle, polygon, circle, oval, or irregular. In some embodiments, a planar geometry is generated in an engineered tissue by positioning specific cellular or bio-ink components and/or void spaces in the x-y planes relative to each other. In some embodiments, the engineered tissues, including vascular wall segments, have a shape that is substantially a sheet or disk. In some embodiments, the engineered vascular wall segments have a shape that is non-tubular, being a vascular wall segment, patch, or sheet, rather than a vascular tube.

In some embodiments, the engineered tissues, including vascular wall segments, are secured to containment vessel by a means suitable to fix the position of the tissue in space relative to the containment vessel. In further embodiments, the engineered tissues are affixed to a surface. In further embodiments, the tissues are affixed to a biocompatible surface. In still further embodiments, a plurality of tissues are associated by affixation to a surface and spatially arranged to form an array, as described herein. In some embodiments, engineered tissues, including vascular wall segments, are subjected to shear force, caused by fluid flow, on one or more sides (see, e.g., FIG. 13). In further embodiments, application of shear force serves to facilitate the maturation and development of a tissue and/or facilitate the migration, differentiation, proliferation, deposition of extracellular matrix, or transport of proteins or molecules into or out of cells within the tissue.

Tissue Geometries

Native tissues are characterized by the presence of spatial and compositional patterns driven by the cellular and extracellular (i.e., void spaces, extracellular matrices, proteinaceous matter, etc.) components of a tissue. Inherent challenges to tissue engineering strategies that deploy synthetic scaffolding to achieve three-dimensionality is the inability to reproduce both the geometric and biologic attributes of native tissue. To date, attempts to create native tissue-like laminar or planar geometry within a scaffold structure while also enabling the incorporation of cells at a density that mimics native tissue have been hampered by technical limitations. Bioprinting overcomes both inherent challenges (planar/laminar geometry and cell density) through the spatially-defined deposition of bio-ink comprised of cells, according to the examples illustrated in FIGS. 18A-F. In some embodiments, planar geometries are created from multiple bio-ink formulations, whereby two or more tissue components (i.e., stromal, epithelial, vascular, bone, cartilage, parenchymal, cortical, medullary, papillary, lobular, etc.) are fabricated in a manner that positions each tissue component/cell population/bio-ink formulation in a defined position relative to each other in the x, y, and/or z planes according to the examples set forth in FIG. 18A-C. In some embodiments, the planar geometries are generated by bioprinting. In some embodiments, the planar geometry recapitulates at least one spatial element of glandular tissue, cancer tissue, a tissue interface (bone:cartilage, for example), vascularized tissue, pyramidal tissue, zonal tissue, or lobulated tissue. In some embodiments, the planar geometry incorporates void spaces. In further embodiments, the void spaces within the planar geometry accommodate fluids that mimic at least one element of bodily fluids, such as blood, lymph, bile, urine, secretions, and the like. In further embodiments, the void spaces optionally contain non-adherent cell types or bodily-fluid-derived components (e.g., blood cells, marrow cells, lymphatic cells, immune cells, cancer cells, platelets, proteins, etc.). In still further embodiments, non-adherent cell types of bodily-fluid-derived components optionally exist as a component of non-void spaces having been introduced into the cell-comprising components of the planar geometry before, during, or after fabrication. In still further embodiments, non-adherent cellular components or bodily-fluid-derived components are recruited from void spaces into cell-comprising spaces within the planar geometry as a result of intercellular interactions or response to secreted factors.

In some embodiments, fluid flow or perfusion is optionally initiated through the void spaces within a geometry. In some embodiments, planar geometries enable the generation of tissue-tissue or tissue-liquid interfaces, as highlighted in FIG. 18B. In further embodiments, the tissues are fabricated into containers that are optically clear to enable real-time observation of cells at the interface(s) created by the geometry.

In some embodiments, tissues comprise multiple layers wherein at least one of the layers is architecturally or compositionally distinct from other layers within the construct, thereby creating a laminar architecture in the z-plane. Examples of laminar architecture include barrier tissues that possess an endothelial or epithelial barrier to an underlying interstitial tissue as depicted by the examples shown in FIG. 18D-F. In some embodiments, laminar tissues represent a portion of the wall of a luminal or tubular structure (e.g., intestine, blood vessel, lymph vessel, renal tubule, ureter, bladder, trachea, esophagus, airway, fallopian tube, urethra, ductular structures, etc.). In other embodiments, laminar tissues represent zones or layers of a tissue (e.g., mucosal tissues, dermal tissues, renal tissues, cardiac tissues, etc.) (see, e.g., FIGS. 8-11). In further embodiments, one or more layers of a tissue incorporate vascular or microvascular components. In still further embodiments, the incorporation of vascular or microvascular components leads to the formation of microvascular or pseudovascular networks within one or more components of the engineered tissue. In some embodiments, one or more components of the tissue with laminar geometry are bioprinted. In some embodiments, one or more tissues with laminar geometry are fabricated adjacent to each other, thereby creating a tissue interface, such as a mucocutaneous junction as drawn in FIG. 18E.

Figure 18B:
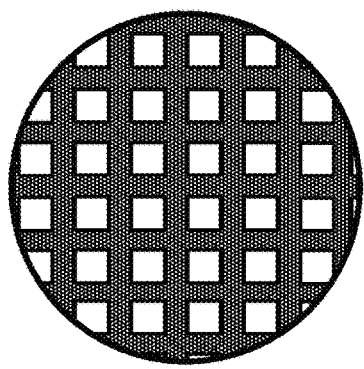
FIG. 18B: Continued schematic diagrams of planar geometry examples (top view) of bioprinted tissues: (6) perfused/arrayed tissues, comprising component #1 (representing channels (i.e., architected to exist as void spaces), vessels (i.e., artery, vein, lymph) or tubes with lumens (i.e., ducts, tubules generated from cells, and/or cell-material composites) and component #2 (each patch can be same or different shape/size, patches can be the same (multiples of the same tissue type), patches can be distinct (multiple tissue types presented within the interconnected grid); each patch may contain one or more cell types and may have one or more architectural or geometrical spatial pattern, achieved by directed patterning in the x, y, and/or z plane; and each patch may be a composite of one or more tissue types (e.g. bone and cartilage); (7) solid and liquid tissue/liquid interfaces, comprising bio-ink #1 (the outer wall of a luminal structure—blood vessel, heart, lymph vessel, stomach, bladder, esophagus, intestine, bone, renal tubule, uterus, airway, fallopian tube, etc.), bio-ink #2 (can be the inner wall of a luminal structure when required—the vascular media, for example, or the mucosal lining of a luminal component of the gastrointestinal system, the epithelial or endothelial lining of a tubular structure, for example), and a third component (a fluid, optionally containing cells or biologically-relevant components (e.g., protein, drugs, pathogens etc.) that interact with the lumenal structure wall as a lumenal fluid or cell-containing solution. The fluid is a liquid or semi-liquid component with a + or − flow through the tissue. In some embodiments, a lining of cells (endothelial, epithelial) may be present in the single- or double-walled structure to serve as the physiologically-correct barrier. In some embodiments, the interactions between component #3 and lumenal surface/wall tissue can be observed by ensuring that the top and/or bottom surface(s) of the container are optically clear.
Figure 18B:
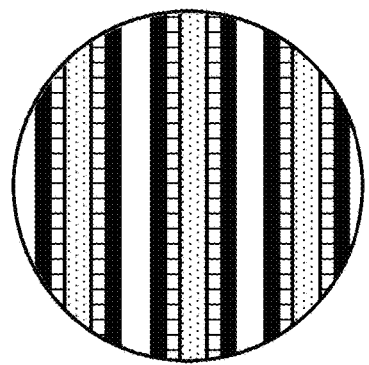
Figure 18C:
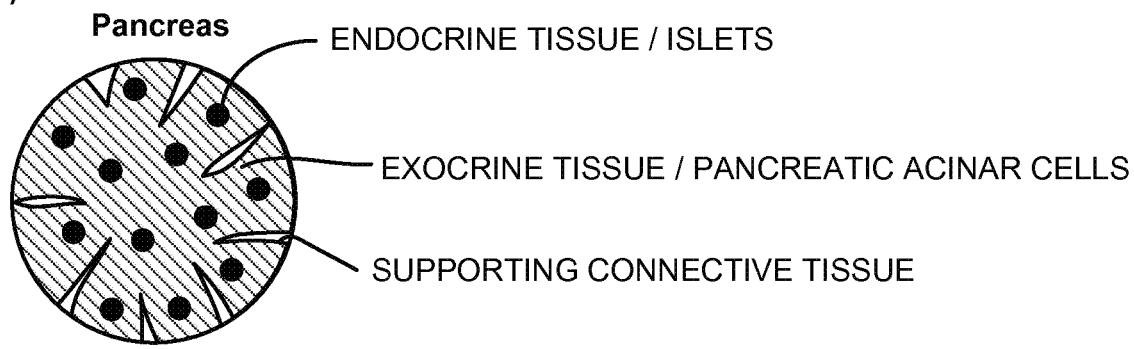
FIG. 18C: Continued schematic diagram of a planar geometry example (top view) of a bioprinted tissue. (8) endocrine/exocrine pancreas tissue, comprising endocrine tissue/islets, exocrine tissue/pancreatic acinar cells and supporting connective tissue. The tissue optionally contains an incorporated microvascular network.
Figure 18D:
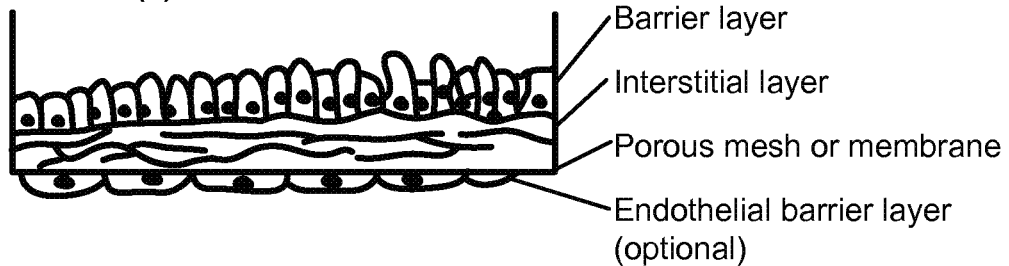
FIG. 18D: Schematic diagrams of laminar geometry examples (side view) of bioprinted tissues. Barrier tissues and specific examples of barrier-like tissues (airway, renal tubule and intestine) are shown. (1) Exemplary barrier tissue, comprising a barrier layer (endothelial or epithelial; single or multiple cells types; one or more cell layers; cells may be positional patterned (small→large airway), an interstitial layer/wall and/or surface of a lumenal tissue, a porous mesh or membrane and an optional endothelial layer. (2) Exemplary airway barrier-like tissue, comprising airway epithelial cells from any level of the airway and an interstitial layer with one or more of: fibroblasts, smooth muscle cells, cartilaginous cells, incorporating a vascular network comprising endothelial cells. Note that the interstitial layer optionally includes planar geometry, for example, spatial positioning of smooth muscle, fibroblasts, and cartilage components as well as positioning of the endothelial network. (3) Exemplary renal tubule barrier-like tissue, comprising renal tubular epithelial cells (homogenous or heterogeneous and can optionally be spatially arranged proximal tubule→collecting duct, for example), an interstitial tissue layer (containing real stromal cells, one or more of the following; vascular cells, erythropoietin-producing cells, pericytes, mesenchymal cells, glomerular cells; also comprising a vascular network); a porous mesh or membrane support and an optional endothelial barrier. (4) Exemplary intestinal barrier-like tissue, comprising an epithelial layer, submucosa layer, and a muscularis layer comprising smooth muscle cells. The epithelial layer comprises gut epithelium, with the potential to utilize epithelial cells from various portion of the gut tube, spatially positional cells to provide directionality to the tissue (small→large intestine, for example). A microvascular network is incorporated into submucosa/mucosa.
Figure 18D:
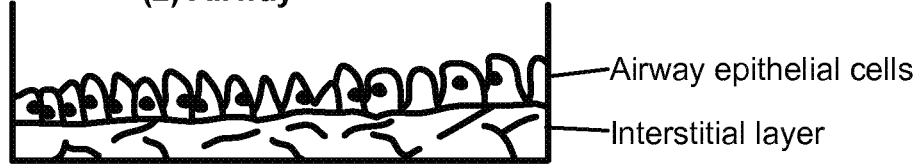
Figure 18D:
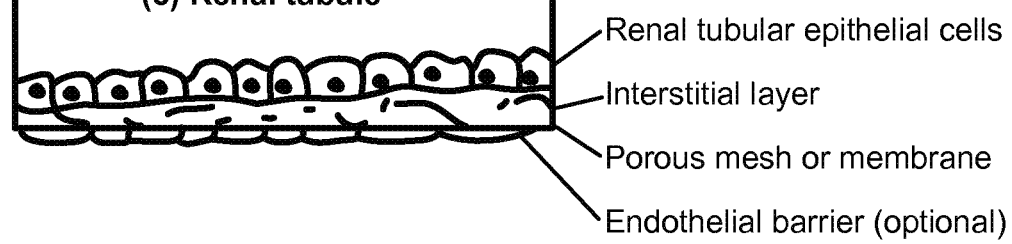
Figure 18D:
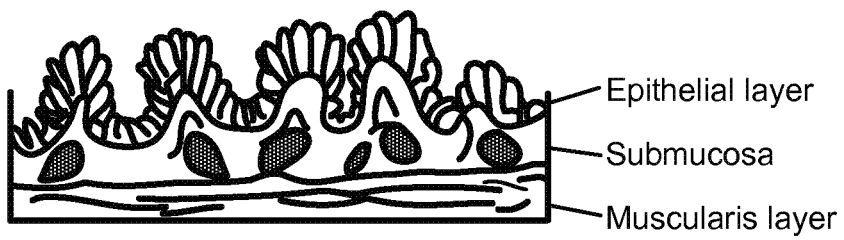
Figure 18E:
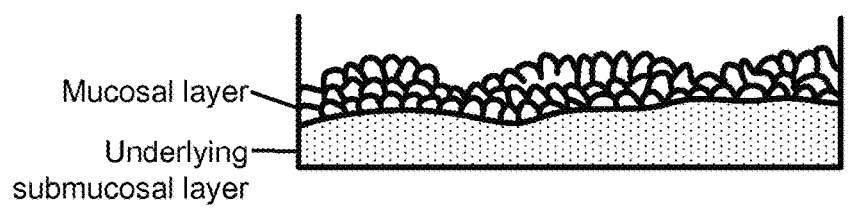
FIG. 18E: Continued schematic diagrams of laminar geometry examples (side view) of bioprinted tissues. Specific examples of barrier-like tissues are shown. (5) Exemplary mucosal surface (e.g., oral) barrier-like tissue, comprising a mucosal layer (comprising epithelial cells and one or more layers of cells, optionally patterned) and an underlying submucosal layer, which may comprise connective tissue, smooth muscle cell and optionally comprise a microvascular network. The surfaces can be constructed from oral, gut, nasal, bladder, bronchial, uterine (endometrial), or penile mucosa. Composite constructs can also be made, a mucocutaneous junction, for example, that adjoins skin to a mucosal tissue such as intestine or bladder. (6) Exemplary mucocutaneous junction barrier-like tissue, comprising an epithelial layer, a lamina propria layer, and a smooth muscle layer on the mucosal side (e.g., oral, nasal conjunctival, urethral, vaginal, anal) and an epidermal layer, a dermal layer, and a skeletal muscle layer, respectively, on the epithelium/skin side (epithelium→epidermis, lamina propria→dermis, smooth muscle→skeletal muscle. Additional tissue-specific components (nerve, gland, etc) can be added in spatially defined locations.
Figure 18E:
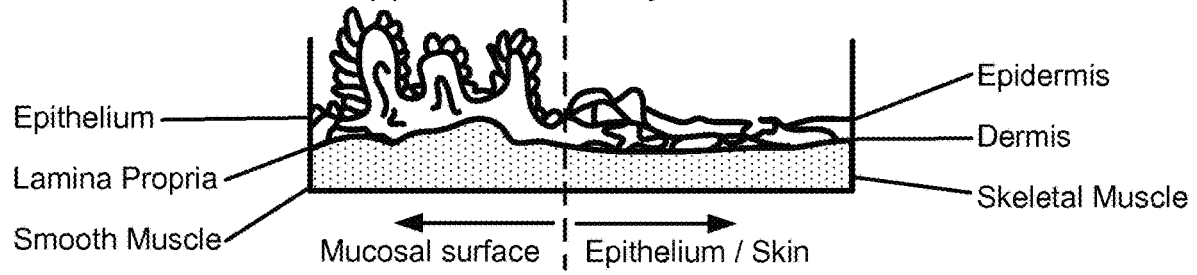
Figure 18F:
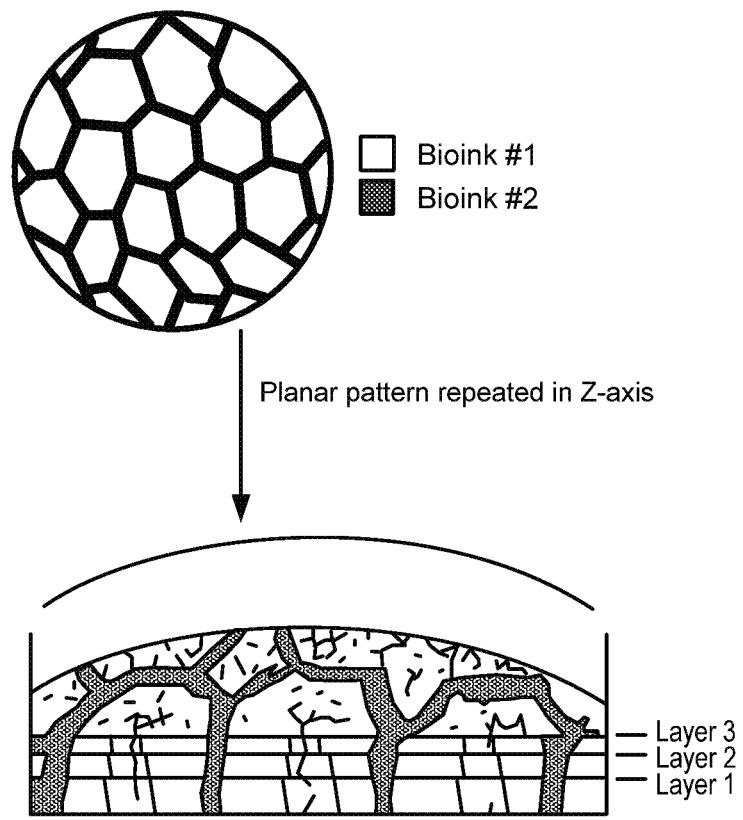
FIG. 18F: Schematic diagrams of combined planar and laminar geometry examples of bioprinted tissues. (1) Exemplary combined planar and laminar geometry bioprinted tissue (top view), comprising a bio-ink #1 in any planar pattern (e.g. lobulated pattern), which can be repeated precisely in the Z axis and a bio-ink #2. (2) Cross-section of exemplary combined planar and laminar geometry bioprinted tissue showing multiple layers (layer 1, layer 2, layer 3). The planar patterns are repeated in layers so that thicker tissues are built up, carrying both the planar geometry elements and the vertical (z-axis) continuations of the pattern into the final tissue product. Features may include contiguous channels, cellular compartments within a tissue (e.g., epithelial glands within a stromal field). Planar patterns may also be varied in the z-axis, layer by layer, to create architectural features. (3) Cross-section of exemplary combined planar and laminar geometry bioprinted tissue showing multiple layers varied in the z-axis. The diagram shows a cross-section of an example of renal tissue comprising medullary renal tissue, papillary renal tissue, and renal tubules, for example, in multiple layers. A similar strategy can be applied to build specific features (glands, follicles, tubes, dusts etc.) into multi-layered tissue structures.
Figure 18F:
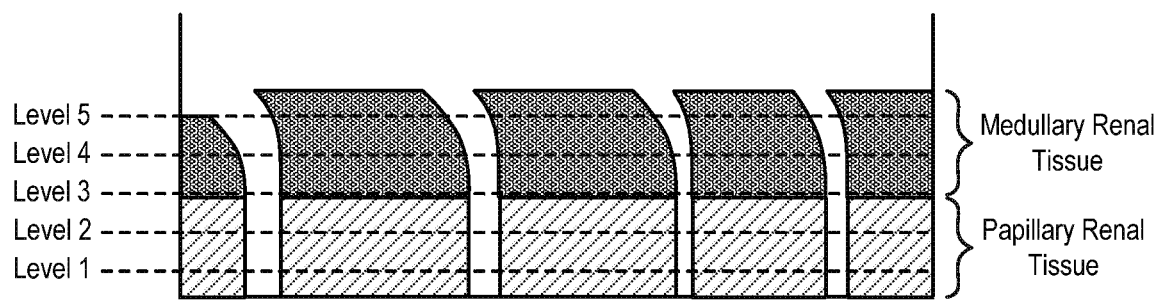

In some embodiments, one or more layers of a multi-layered engineered tissue with laminar geometry also comprise planar geometry, according to the non-limiting examples set forth in FIG. 18F. In some embodiments, the same planar geometry is continued in each layer, resulting in a three-dimensional tissue with continuous architecture in the x, y, and z planes. In some embodiments, the composition or planar geometry of one or more laminar layers is varied, such that the resulting three-dimensional tissue possesses a complex architecture in both the x, y and z planes according to the non-limiting example of renal tubules illustrated in FIG. 18F.

Cells

Disclosed herein, in some embodiments, are engineered tissues comprising one or more types of mammalian cells. Also disclosed herein, in some embodiments, are engineered vascular wall segments comprising smooth muscle cells; and optionally, fibroblasts and/or endothelial cells. In other embodiments, the tissues are airway analogues. In some embodiments, the airway analogues comprise: pulmonary fibroblasts and optionally, smooth muscle cells and/or endothelial cells, wherein at least one surface of the tissue is layered with small airway epithelial cells. In other embodiments, the tissues are liver analogues. In further embodiments, the liver tissue analogues comprise: hepatocytes or hepatocyte-like cells and optionally bile duct epithelial cells and optionally, non-parenchymal cell types including, but not limited to, stellate cells, endothelial cells, kupffer cells, immune cells, or myofibroblasts.

In some embodiments, any mammalian cell is suitable for inclusion in the engineered tissues and arrays thereof. In further embodiments, at least one component of the engineered tissues is an adherent cell type. In further embodiments, the mammalian cells are, by way of non-limiting examples, contractile or muscle cells (e.g., skeletal muscle cells, cardiomyocytes, smooth muscle cells, and myoblasts), connective tissue cells (e.g., bone cells, cartilage cells, fibroblasts, and cells differentiating into bone forming cells, chondrocytes, or lymph tissues), bone marrow cells, endothelial cells, skin cells, epithelial cells, breast cells, vascular cells, blood cells, lymph cells, neural cells, Schwann cells, gastrointestinal cells, liver cells, pancreatic cells, lung cells, tracheal cells, corneal cells, genitourinary cells, kidney cells, reproductive cells, adipose cells, parenchymal cells, pericytes, mesothelial cells, stromal cells, undifferentiated cells (e.g., embryonic cells, stem cells, and progenitor cells), endoderm-derived cells, mesoderm-derived cells, ectoderm-derived cells, cancer-derived cells and combinations thereof.

In one embodiment, the cells are smooth muscle cells. In another embodiment, the cells are smooth muscle cells and fibroblasts. In yet another embodiment, the cells are smooth muscle cells and endothelial cells. In still another embodiment, the cells are smooth muscle cells, fibroblasts, and endothelial cells. In embodiments including more than one cell type, the cell types are present in many suitable ratios, examples of which are described herein.

In some embodiments, the cells are adult, differentiated cells. In further embodiments, "differentiated cells" are cells with a tissue-specific phenotype consistent with, for example, a smooth muscle cell, a fibroblast, or an endothelial cell at the time of isolation, wherein tissue-specific phenotype (or the potential to display the phenotype) is maintained from the time of isolation to the time of use. In other embodiments, the cells are adult, non-differentiated cells. In further embodiments, "non-differentiated cells" are cells that do not have, or have lost, the definitive tissue-specific traits of for example, smooth muscle cells, fibroblasts, or endothelial cells. In some embodiments, non-differentiated cells include stem cells. In further embodiments, "stem cells" are cells that exhibit potency and self-renewal. Stem cells include, but are not limited to, totipotent cells, pluripotent cells, multipotent cells, oligopotent cells, unipotent cells, and progenitor cells. In various embodiments, stem cells are embryonic stem cells, adult stem cells, amniotic stem cells, and induced pluripotent stem cells. In yet other embodiments, the cells are a mixture of adult, differentiated cells and adult, non-differentiated cells.

In some embodiments, the smooth muscle cells are human smooth muscle cells. In some embodiments, suitable smooth muscle cells originated from tissue including, by way of non-limiting example, blood, blood vessel, lymphatic vessel, tissue of the digestive tract, tissue of the genitourinary tract, adipose tissue, tissue of the respiratory tract, tissue of the reproductive system, bone marrow, and umbilical tissue. In some embodiments, the endothelial cells are human endothelial cells. In some embodiments, suitable endothelial cells originate from tissue including, by way of non-limiting example, blood, blood vessel, lymphatic vessel, tissue of the digestive tract, tissue of the genitourinary tract, adipose tissue, tissue of the respiratory tract, tissue of the reproductive system, bone marrow, and umbilical tissue. In some embodiments, the fibroblasts are human fibroblasts. In some embodiments, suitable fibroblasts are non-vascular fibroblasts. In other embodiments, suitable fibroblasts are derived from vascular adventitia. In some embodiments, some or all of the cells are derived from mammalian lipoaspirate. In further embodiments, some or all of the cells are cultured from the stromal vascular fraction of mammalian lipoaspirate. See Example 1.

In various embodiments, the cell types and/or source of the cells are selected, configured, treated, or modulated based on a specific research goal or objective. In some embodiments, one or more specific cell types are selected, configured, treated, or modulated to facilitate investigation of a particular disease or condition. In some embodiments, one or more specific cell types are selected, configured, treated, or modulated to facilitate investigation of a disease or a condition of a particular subject. In some embodiments, one or more specific cell types are derived from two or more distinct human donors. In some embodiments, one or more specific cell types are derived from a particular vertebrate subject. In further embodiments, one or more specific cell types are derived from a particular mammalian subject. In still further embodiments, one or more specific cell types are derived from a particular human subject. In further embodiments, one or more specific cell types are derived from a particular subject with a specific phenotype associated with disease or tissue functionality. In still further embodiments, the subject-specific cells are isolated from the target tissue of interest by way of biopsy or tissue sampling. In further embodiments, the subject-specific cells are utilized to fabricate tissue immediately after isolation. In other embodiments, the subject-specific cells are manipulated in vitro prior to use in the fabrication of three-dimensional tissues; wherein the manipulation includes one or more of: expansion, differentiation, directed differentiation, proliferation, exposure to proteins or nucleic acids, incorporation of genetic vectors, incorporation of genetic or non-genetic cell-tracing moieties, de-differentiation (i.e., generation of induced pluripotent stem cells or equivalents), cryopreservation. In some embodiments, subject-specific cells are isolated from a tissue other than the target tissue. In further embodiments, the subject-specific cells require differentiation into cell types of interest within the target tissue. In still further embodiments, subject-specific cells that require differentiation are differentiated prior to, during, or after fabrication into a three-dimensional structure.

Methods of Culturing Cells

The cell types used in the engineered tissues of the invention are suitably cultured in any manner known in the art. Methods of cell and tissue culturing are known in the art, and are described, for example, in Freshney, R., *Culture of Animal Cells: A Manual of Basic Techniques*, Wiley (1987), the contents of which are incorporated herein by reference for such information. General mammalian cell culture techniques, cell lines, and cell culture systems suitably used in conjunction with the present invention are also described in Doyle, A., Griffiths, J. B., Newell, D. G., (eds.) *Cell and Tissue Culture: Laboratory Procedures*, Wiley (1998), the contents of which are incorporated herein by reference for such information.

Appropriate growth conditions for mammalian cells in culture are well known in the art. See, e.g., Example 1. Cell culture media generally include essential nutrients and, optionally, additional elements such as growth factors, salts, minerals, vitamins, platelet-rich plasma, etc., that are optionally selected according to the cell type(s) being cultured. In some embodiments, particular ingredients are selected to enhance cell growth, differentiation, secretion of specific proteins, etc. In general, standard growth media include Dulbecco's Modified Eagle Medium (DMEM) or low glucose with 110 mg/L pyruvate and glutamine, supplemented with 1-20% fetal bovine serum (FBS), calf serum, or human serum, 100 U/mL penicillin, and 0.1 mg/mL streptomycin are appropriate, as are various other standard media well known to those in the art. Preferably cells are cultured under sterile conditions in an atmosphere of 1-21% $O_2$ and preferably 3-5% $CO_2$, at a temperature at or near the body temperature of the animal of origin of the cell. For example, human cells are preferably cultured at approximately 37° C.

The cells are optionally cultured with cellular differentiation agents to induce differentiation of the cell along the desired line. For instance, cells are optionally cultured with growth factors, cytokines, etc. In some embodiments, the term "growth factor" refers to a protein, a polypeptide, or a complex of polypeptides, including cytokines, that are produced by a cell and affect itself and/or a variety of other neighboring or distant cells. Typically growth factors affect the growth and/or differentiation of specific types of cells, either developmentally or in response to a multitude of physiological or environmental stimuli. Some, but not all, growth factors are hormones. Exemplary growth factors are insulin, insulin-like growth factor (IGF), nerve growth factor (NGF), vascular endothelial growth factor (VEGF), keratinocyte growth factor (KGF), fibroblast growth factors (FGFs), including basic FGF (bFGF), platelet-derived growth factors (PDGFs), including PDGF-AA and PDGF-AB, hepatocyte growth factor (HGF), transforming growth factor alpha (TGF-α), transforming growth factor beta (TGF-β), including TGFβ1 and TGFβ3, epidermal growth factor (EGF), granulocyte-macrophage colony-stimulating factor (GM-CSF), granulocyte colony-stimulating factor (G-CSF), interleukin-6 (IL-6), IL-8, and the like. Growth factors are discussed in, among other places, *Molecular Cell Biology*, Scientific American Books, Darnell et al., eds., 1986; *Principles of Tissue Engineering,* 2d ed., Lanza et al., eds., Academic Press, 2000. The skilled artisan will understand that any and all culture-derived growth factors in the conditioned media described herein are within the scope of the invention.

Bio-Ink and Multicellular Aggregates

Disclosed herein, in certain embodiments, are three-dimensional living tissues, including vascular wall segments, arrays thereof, and methods that comprise bioprinted cells. In some embodiments, cells are bioprinted by depositing or extruding bio-ink from a bioprinter. In some embodiments, "bio-ink" includes liquid, semi-solid, or solid compositions comprising a plurality of cells. In some embodiments, bio-ink comprises liquid or semi-solid cell solutions, cell suspensions, or cell concentrations. In further embodiments, a cell solution, suspension, or concentration comprises a liquid or semi-solid (e.g., viscous) carrier and a plurality of cells. In still further embodiments, the carrier is a suitable cell nutrient media, such as those described herein. In some embodiments, bio-ink comprises a plurality of cells that optionally cohere into multicellular aggregates prior to bioprinting. In further embodiments, bio-ink comprises a plurality of cells and is bioprinted to produce a specific planar and/or laminar geometry; wherein cohesion of the individual cells within the bio-ink takes place before, during and/or after bioprinting. In some embodiments, the bio-ink is produced by 1) collecting a plurality of cells in a fixed volume; wherein the cellular component(s) represent at least about 30% and at most 100% of the total volume. In some embodiments, bio-ink comprises semi-solid or solid multicellular aggregates or multicellular bodies. In further embodiments, the bio-ink is produced by 1) mixing a plurality of cells or cell aggregates and a biocompatible liquid or gel in a pre-determined ratio to result in bio-ink, and 2) compacting the bio-ink to produce the bio-ink with a desired cell density and viscosity. In some embodiments, the compacting of the bio-ink is achieved by centrifugation, tangential flow filtration ("TFF"), or a combination thereof. In some embodiments, the compacting of the bio-ink results in a composition that is extrudable, allowing formation of multicellular aggregates or multicellular bodies. In some embodiments, "extrudable" means able to be shaped by forcing (e.g., under pressure) through a nozzle or orifice (e.g., one or more holes or tubes). In some embodiments, the compacting of the bio-ink results from growing the cells to a suitable density. The cell density necessary for the bio-ink will vary with the cells being used and the tissue or organ being produced. In some embodiments, the cells of the bio-ink are cohered and/or adhered. In some embodiments, "cohere," "cohered," and "cohesion" refer to cell-cell adhesion properties that bind cells, multicellular aggregates, multicellular bodies, and/or layers thereof. In further embodiments, the terms are used interchangeably with "fuse," "fused," and "fusion." In some embodiments, the bio-ink additionally comprises support material, cell culture medium (or supplements thereof), extracellular matrix (or components thereof), cell adhesion agents, cell death inhibitors, anti-apoptotic agents, anti-oxidants, extrusion compounds, and combinations thereof.

In various embodiments, the cells are any suitable cell. In further various embodiments, the cells are vertebrate cells, mammalian cells, human cells, or combinations thereof. In some embodiments, the type of cell used in a method disclosed herein depends on the type of construct or tissue being produced. In some embodiments, the bio-ink comprises one type of cell (also referred to as a "homogeneous" or "monotypic" bio-ink). In some embodiments, the bio-ink comprises more than one type of cell (also referred to as a "heterogeneous" or "polytypic" bio-ink).

Cell Culture Media

In some embodiments, the bio-ink comprises a cell culture medium. The cell culture medium is any suitable medium. In various embodiments, suitable cell culture media include, by way of non-limiting examples, Dulbecco's Phosphate Buffered Saline, Earle's Balanced Salts, Hanks' Balanced Salts, Tyrode's Salts, Alsever's Solution, Gey's Balanced Salt Solution, Kreb's-Henseleit Buffer Modified, Kreb's-Ringer Bicarbonate Buffer, Puck's Saline, Dulbecco's Modified Eagle's Medium, Dulbecco's Modified Eagle's Medium/Nutrient F-12 Ham, Nutrient Mixture F-10 Ham (Ham's F-10), Medium 199, Minimum Essential Medium Eagle, RPMI-1640 Medium, Ames' Media, BGJb Medium (Fitton-Jackson Modification), Click's Medium, CMRL-1066 Medium, Fischer's Medium, Glasgow Minimum Essential Medium (GMEM), Iscove's Modified Dulbecco's Medium (IMDM), L-15 Medium (Leibovitz), McCoy's 5 A Modified Medium, NCTC Medium, Swim's S-77 Medium, Waymouth Medium, William's Medium E, or combinations thereof. In some embodiments, the cell culture medium is modified or supplemented. In some embodiments, the cell culture medium further comprises albumin, selenium, transferrins, fetuins, sugars, amino acids, vitamins, growth factors, cytokines, hormones, antibiotics, lipids, lipid carriers, cyclodextrins, platelet-rich plasma, or a combination thereof.

Extracellular Matrix

In some embodiments, the bio-ink further comprises one or more components of an extracellular matrix or derivatives thereof. In some embodiments, "extracellular matrix" includes proteins that are produced by cells and transported out of the cells into the extracellular space, where they serve as a support to hold tissues together, to provide tensile strength, and/or to facilitate cell signaling. Examples, of extracellular matrix components include, but are not limited to, collagens, fibronectin, laminins, hyaluronates, elastin, and proteoglycans. For example, in some embodiments, the multicellular aggregates contain various ECM proteins (e.g., gelatin, fibrinogen, fibrin, collagens, fibronectin, laminins, elastin, and/or proteoglycans). The ECM components or derivatives of ECM components are optionally added to the cell paste used to form the multicellular aggregate. The ECM components or derivatives of ECM components added to the cell paste are optionally purified from a human or animal source, or produced by recombinant methods known in the art. Alternatively, the ECM components or derivatives of ECM components are naturally secreted by the cells in the elongate cellular body, or the cells used to make the elongate cellular body are optionally genetically manipulated by any suitable method known in the art to vary the expression level of one or more ECM components or derivatives of ECM components and/or one or more cell adhesion molecules or cell-substrate adhesion molecules (e.g., selectins, integrins, immunoglobulins, and adherins). In some embodiments, the ECM components or derivatives of ECM components promote cohesion of the cells in the multicellular aggregates. For example, gelatin and/or fibrinogen is suitably added to the cell paste, which is used to form multicellular aggregates. The fibrinogen is converted to fibrin by the addition of thrombin.

In some embodiments, the bio-ink further comprises an agent that encourages cell adhesion.

Figure 15:
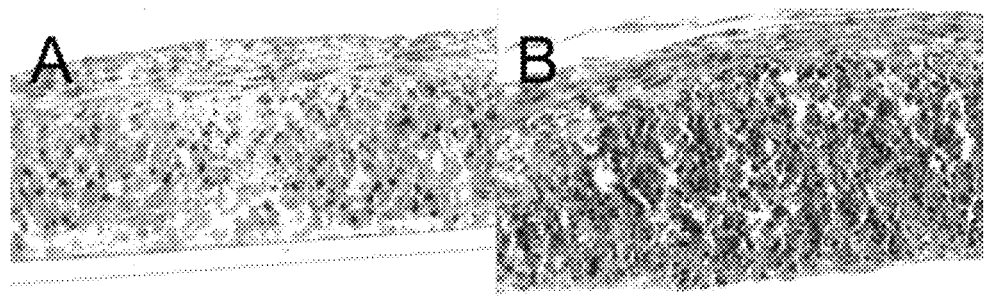
FIG. 15 is a pair of non-limiting photomicrographs depicting stimulation of bioprinted multi-layered blood vessel wall segments with TGF-β1. Stimulation of the bioprinted blood vessel wall segment with the fibroproliferative cytokine TGF-β1 (10 ng/ml) results in a significant increase in collagen deposition and organization as seen by trichrome staining of formalin-fixed paraffin-embedded tissue constructs following 5+ days of stimulation. Control (A), TGF-β1-treated (B).
Figure 16:
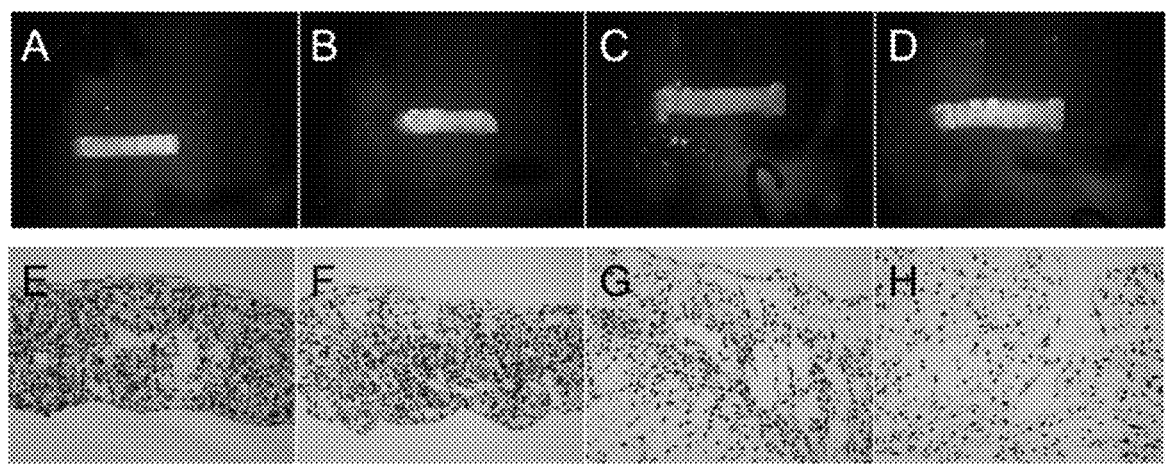
FIG. 16 is a series of photomicrographs depicting stimulation of bioprinted liver tissue containing hepatic stellate cells with TGF-β1. Incubation of bioprinted hepatic stellate cell sheets with increasing concentrations of TGF-b1 (0, 1, 10, 50 ng/ml), results in changes in gross observation of the bioprinted tissues as increases in cytokine concentration lead to increases in tissue outgrowth formation (A-D, 0-50 ng/mL). Trichrome staining of tissue sections from bioprinted hepatic stellate-containing tissues reveals increases in collagen deposition and construct size and dramatic decreases in cell density (E-H, 0-50 ng/ml).

In some embodiments, the bio-ink further comprises an agent that inhibits cell death (e.g., necrosis, apoptosis, or autophagocytosis). In some embodiments, the bio-ink further comprises an anti-apoptotic agent. Agents that inhibit cell death include, but are not limited to, small molecules, antibodies, peptides, peptibodies, or combination thereof. In some embodiments, the agent that inhibits cell death is selected from: anti-TNF agents, agents that inhibit the activity of an interleukin, agents that inhibit the activity of an interferon, agents that inhibit the activity of an GCSF (granulocyte colony-stimulating factor), agents that inhibit the activity of a macrophage inflammatory protein, agents that inhibit the activity of TGF-B (transforming growth factor B) (see, e.g., FIGS. 15 and 16), agents that inhibit the activity of an MMP (matrix metalloproteinase), agents that inhibit the activity of a caspase, agents that inhibit the activity of the MAPK/JNK signaling cascade, agents that inhibit the activity of a Src kinase, agents that inhibit the activity of a JAK (Janus kinase), or a combination thereof. In some embodiments, the bio-ink comprises an anti-oxidant. In some embodiments, the bio-ink comprises oxygen-carriers or other cell-specific nutrients.

Extrusion Compounds

In some embodiments, the bio-ink further comprises an extrusion compound (i.e., a compound that modifies the extrusion properties of the bio-ink). Examples of extrusion compounds include, but are not limited to gels, hydrogels, peptide hydrogels, amino acid-based gels, surfactant polyols (e.g., Pluronic F-127 or PF-127), thermo-responsive polymers, hyaluronates, alginates, extracellular matrix components (and derivatives thereof), collagens, other biocompatible natural or synthetic polymers, nanofibers, and self-assembling nanofibers. In some embodiments, extrusion compounds are removed after bioprinting by physical, chemical, or enzymatic means.

Gels, sometimes referred to as jellies, have been defined in various ways. For example, the United States Pharmacopoeia defines gels as semisolid systems consisting of either suspensions made up of small inorganic particles or large organic molecules interpenetrated by a liquid. Gels include a single-phase or a two-phase system. A single-phase gel consists of organic macromolecules distributed uniformly throughout a liquid in such a manner that no apparent boundaries exist between the dispersed macromolecules and the liquid. Some single-phase gels are prepared from synthetic macromolecules (e.g., carbomer) or from natural gums (e.g., tragacanth). In some embodiments, single-phase gels are generally aqueous, but will also be made using alcohols and oils. Two-phase gels consist of a network of small discrete particles.

Gels, in some cases, are classified as being hydrophobic or hydrophilic. In certain embodiments, the base of a hydrophobic gel consists of a liquid paraffin with polyethylene or fatty oils gelled with colloidal silica, or aluminum or zinc soaps. In contrast, the base of hydrophobic gels usually consists of water, glycerol, or propylene glycol gelled with a suitable gelling agent (e.g., tragacanth, starch, cellulose derivatives, carboxyvinylpolymers, and magnesium-aluminum silicates). In certain embodiments, the rheology of the compositions or devices disclosed herein is pseudo plastic, plastic, thixotropic, or dilatant.

Suitable hydrogels include those derived from collagen, hyaluronate, fibrin, alginate, agarose, chitosan, and combinations thereof. In other embodiments, suitable hydrogels are synthetic polymers. In further embodiments, suitable hydrogels include those derived from poly(acrylic acid) and derivatives thereof, poly(ethylene oxide) and copolymers thereof, poly(vinyl alcohol), polyphosphazene, and combinations thereof. In various specific embodiments, the confinement material is selected from: hydrogel, NovoGel™, agarose, alginate, gelatin, Matrigel™, hyaluronan, poloxamer, peptide hydrogel, poly(isopropyl n-polyacrylamide), polyethylene glycol diacrylate (PEG-DA), hydroxyethyl methacrylate, polydimethylsiloxane, polyacrylamide, poly(lactic acid), silicon, silk, or combinations thereof.

In some embodiments, hydrogel-based extrusion compounds are thermoreversible gels (also known as thermo-responsive gels or thermogels). In some embodiments, a suitable thermoreversible hydrogel is not a liquid at room temperature. In specific embodiments, the gelation temperature (Tgel) of a suitable hydrogel is about 10° C., 11° C., 12° C., 13° C., 14° C., 15° C., 16° C., 17° C., 18° C., 19° C., 20° C., 21° C., 22° C., 23° C., 24° C., 25° C., 26° C., 27° C., 28° C., 29° C., 30° C., 31° C., 32° C., 33° C., 34° C., 35° C., 36° C., 37° C., 38° C., 39° C., 40° C., including increments therein. In certain embodiments, the Tgel of a suitable hydrogel is about 10° C. to about 40° C. In further embodiments, the Tgel of a suitable hydrogel is about 20° C. to about 30° C. In some embodiments, the bio-ink (e.g., comprising hydrogel, one or more cell types, and other additives, etc.) described herein is not a liquid at room temperature. In some embodiments, a suitable thermoreversible hydrogel is not a liquid at mammalian body temperature. In specific embodiments, the gelation temperature (Tgel) of a suitable hydrogel is about 22° C., 23° C., 24° C., 25° C., 26° C., 27° C., 28° C., 29° C., 30° C., 31° C., 32° C., 33° C., 34° C., 35° C., 36° C., 37° C., 38° C., 39° C., 40° C., 41° C., 43° C., 44° C., 45° C., 46° C., 47° C., 48° C., 49° C., 50° C., 51° C., 52° C., including increments therein. In certain embodiments, the Tgel of a suitable hydrogel is about 22° C. to about 52° C. In further embodiments, the Tgel of a suitable hydrogel is about 32° C. to about 42° C. In some embodiments, the bio-ink (e.g., comprising hydrogel, one or more cell types, and other additives, etc.) described herein is not a liquid at mammalian body temperature. In specific embodiments, the gelation temperature (Tgel) of a bio-ink described herein is about 10° C., about 15° C., about 20° C., about 25° C., about 30° C., about 35° C., about 40° C., about 45° C., about 50° C., about 55° C., including increments therein. In a specific embodiment, the Tgel of a bio-ink described herein is about 10° C. to about 15° C. In another specific embodiment, the Tgel of a bio-ink described herein is about 15° C. to about 20° C. In another specific embodiment, the Tgel of a bio-ink described herein is about 20° C. to about 25° C. In another specific embodiment, the Tgel of a bio-ink described herein is about 25° C. to about 30° C. In another specific embodiment, the Tgel of a bio-ink described herein is about 30° C. to about 35° C. In another specific embodiment, the Tgel of a bio-ink described herein is about 35° C. to about 40° C. In another specific embodiment, the Tgel of a bio-ink described herein is about 40° C. to about 45° C. In another specific embodiment, the Tgel of a bio-ink described herein is about 45° C. to about 50° C.

Polymers composed of polyoxypropylene and polyoxyethylene form thermoreversible gels when incorporated into aqueous solutions. These polymers have the ability to change from the liquid state to the gel state at temperatures maintainable in a bioprinter apparatus. The liquid state-to-gel state phase transition is dependent on the polymer concentration and the ingredients in the solution.

Poloxamer 407 (Pluronic F-127 or PF-127) is a nonionic surfactant composed of polyoxyethylene-polyoxypropylene copolymers. Other poloxamers include 188 (F-68 grade), 237 (F-87 grade), 338 (F-108 grade). Aqueous solutions of poloxamers are stable in the presence of acids, alkalis, and metal ions. PF-127 is a commercially available polyoxyethylene-polyoxypropylene triblock copolymer of general formula E106 P70 E106, with an average molar mass of 13,000. The polymer is optionally further purified by suitable methods that will enhance gelation properties of the polymer. It contains approximately 70% ethylene oxide, which accounts for its hydrophilicity. It is one of the series of poloxamer ABA block copolymers. PF-127 has good solubilizing capacity, low toxicity and is, therefore, considered a suitable extrusion compound.

In some embodiments, the viscosity of the hydrogels and bio-inks presented herein is measured by any means described. For example, in some embodiments, an LVDV-II+CP Cone Plate Viscometer and a Cone Spindle CPE-40 is used to calculate the viscosity of the hydrogels and bio-inks. In other embodiments, a Brookfield (spindle and cup) viscometer is used to calculate the viscosity of the hydrogels and bio-inks. In some embodiments, the viscosity ranges referred to herein are measured at room temperature. In other embodiments, the viscosity ranges referred to herein are measured at body temperature (e.g., at the average body temperature of a healthy human).

In further embodiments, the hydrogels and/or bio-inks are characterized by having a viscosity of between about 500 and 1,000,000 centipoise, between about 750 and 1,000,000 centipoise; between about 1000 and 1,000,000 centipoise; between about 1000 and 400,000 centipoise; between about 2000 and 100,000 centipoise; between about 3000 and 50,000 centipoise; between about 4000 and 25,000 centipoise; between about 5000 and 20,000 centipoise; or between about 6000 and 15,000 centipoise.

In some embodiments, the bio-ink comprises cells and extrusion compounds suitable for continuous bioprinting. In specific embodiments, the bio-ink has a viscosity of about 1500 mPa·s. In some embodiments, a mixture of Pluronic F-127 and cellular material is suitable for continuous bioprinting. Such a bio-ink is suitably prepared by dissolving Pluronic F-127 powder by continuous mixing in cold (4° C.) phosphate buffered saline (PBS) over 48 hours to 30% (w/v). Pluronic F-127 is also suitably dissolved in water. In some embodiments, cells are cultivated and expanded using standard sterile cell culture techniques. In further embodiments, the cells are pelleted at 200 g for example, and re-suspended in the 30% Pluronic F-127 and aspirated into a reservoir affixed to a bioprinter where it is, in some embodiments, allowed to solidify at a gelation temperature from about 10 to about 25° C. Gelation of the bio-ink prior to bioprinting is optional. The bio-ink, including bio-ink comprising Pluronic F-127 is optionally dispensed as a liquid.

In various embodiments, the concentration of Pluronic F-127 is any value with suitable viscosity and/or cytotoxicity properties. In some embodiments, a suitable concentration of Pluronic F-127 is able to support weight while retaining its shape when bioprinted. In some embodiments, the concentration of Pluronic F-127 is about 10%, about 15%, about 20%, about 25%, about 30%, about 35%, about 40%, about 45%, or about 50%. In some embodiments, the concentration of Pluronic F-127 is between about 30% and about 40%, or between about 30% and about 35%.

In some embodiments, the non-cellular components of the bio-ink (e.g., extrusion compounds, etc.) are removed prior to use. In further embodiments, the non-cellular components are, for example, hydrogels, peptide hydrogels, amino acid-based gels, surfactant polyols, thermo-responsive polymers, hyaluronates, alginates, collagens, or other biocompatible natural or synthetic polymers. In still further embodiments, the non-cellular components are removed by physical, chemical, or enzymatic means. In some embodiments, a proportion of the non-cellular components remain associated with the cellular components at the time of use.

In some embodiments, the cells are pre-treated to increase cellular interaction. For example, cells are suitably incubated inside a centrifuge tube after centrifugation in order to enhance cell-cell interactions prior to shaping the bio-ink.

Exemplary Cell Ratios

In some embodiments, the bio-ink comprises multicellular bodies, which further comprise smooth muscle cells and endothelial cells. In further embodiments, the ratio of smooth muscle cells to endothelial cells is any suitable ratio. In still further embodiments, the ratio of smooth muscle cells to endothelial cells is about 90:10 to about 60:40. In a particular embodiment, the multicellular bodies comprise smooth muscle cells and endothelial cells and the ratio of smooth muscle cells to endothelial cells is about 85:15. In another particular embodiment, the multicellular bodies comprise smooth muscle cells and endothelial cells and the ratio of smooth muscle cells to endothelial cells is about 70:30.

In some embodiments, the bio-ink comprises multicellular bodies, which further comprise smooth muscle cells and fibroblasts. In further embodiments, the ratio of smooth muscle cells to fibroblasts is any suitable ratio. In still further embodiments, the ratio of smooth muscle cells to fibroblasts is about 90:10 to about 60:40.

In some embodiments, the bio-ink comprises multicellular bodies, which further comprise smooth muscle cells, fibroblasts, and endothelial cells. In further embodiments, the ratio of smooth muscle cells, fibroblasts, and endothelial cells is any suitable ratio. In still further embodiments, the ratio of smooth muscle cells to fibroblasts and endothelial cells is about 70:25:5.

Self-Sorting of Cells

In some embodiments, multicellular aggregates used to form the construct or tissue comprises all cell types to be included in the engineered tissue (e.g., endothelial cells, smooth muscle cells, fibroblasts, etc.); in such an example each cell type migrates to an appropriate position (e.g., during maturation) to form the engineered tissue, such as a vascular wall segment. In other embodiments, the multicellular aggregates used to form the structure comprises fewer than all the cell types to be included in the engineered tissue. In some embodiments, cells of each type are uniformly distributed within a multicellular aggregates, or region or layer of the tissue. In other embodiments, cells of each type localize to particular regions within a multicellular aggregate or layers or regions of the tissue.

Figure 3:
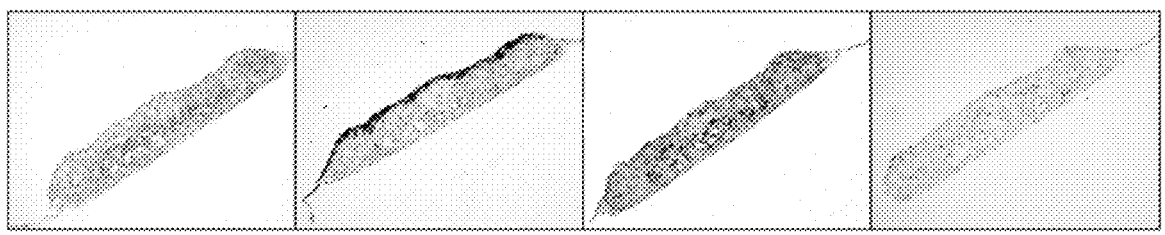
FIG. 3 depicts non-limiting examples of bioprinted vascular wall segments constructed with SMC-only bio-ink cylinders followed by bioprinting of a second layer composed of EC concentrate, creating a laminar architecture. Various staining conditions are shown to indicate distribution and position of cell types. (L to R) H&E, CD31, a-SMA and TUNEL staining of vessel wall constructs bioprinted with SMC bio-ink to form a first layer atop a porous membrane, followed by deposition of an EC concentrate from the NovoGen MMX Bioprinter™ to form a second layer. Following 5 days of culture organization of an EC lining is observed on the top of the construct and an SMC rich vessel construct wall is present. A limited number of TUNEL-positive nuclei are found throughout the bioprinted structure.

For example, in the case of an engineered vascular wall segment (e.g., vascular tissue sheet) comprising smooth muscle cells and endothelial cells in a suitable ratio (e.g., 85:15, 70:30, etc.), neighboring, bioprinted cohered polytypic cylindrical bio-ink units fuse. During maturation, endothelial cells localize to some extent to the periphery of the construct and collagen is formed. See, e.g., FIGS. 1, 3, and 4a. By way of further example, in the case of a bioprinted vascular wall segment comprising smooth muscle cells, fibroblasts, and endothelial cells in a suitable ratio (e.g., 70:25:5, etc.), bioprinted polytypic cylindrical bio-ink fuse and endothelial cells localize to some extent to the periphery of the construct. In some embodiments, localization of cell types within a construct mimics the layered structure of in vivo or ex vivo mammalian tissues. In further embodiments, for example in an engineered vascular wall segment, localization of cell types within a construct forms putative tunica intima, tunica media, and tunica adventitia.

In some embodiments, the sorting or self-sorting of cells is accelerated, enhanced, or augmented by the application of one or more layers of cells. For example, in some embodiments, a construct bioprinted with multicellular aggregates including smooth muscle cells and endothelial cells is further subjected to application of a layer of endothelial cells on one or more surfaces of the construct. In further embodiments, the result is augmentation of the layering produced by the localization of the endothelial cells to the periphery of the construct.

Pre-Formed Scaffold

In some embodiments, disclosed herein are engineered, implantable tissues and organs that are free or substantially free of any pre-formed scaffold. In further embodiments, "scaffold" refers to synthetic scaffolds such as polymer scaffolds and porous hydrogels, non-synthetic scaffolds such as pre-formed extracellular matrix layers, dead cell layers, and decellularized tissues, and any other type of pre-formed scaffold that is integral to the physical structure of the engineered tissue and/or organ and not removed from the tissue and/or organ. In still further embodiments, decellularized tissue scaffolds include decellularized native tissues or decellularized cellular material generated by cultured cells in any manner; for example, cell layers that are allowed to die or are decellularized, leaving behind the ECM they produced while living.

In some embodiments, the engineered tissues, including vascular wall segments, and arrays thereof do not utilize any pre-formed scaffold, e.g., for the formation of the tissue, any layer of the tissue, or formation of the tissue's shape. As a non-limiting example, the engineered tissues of the present invention do not utilize any pre-formed, synthetic scaffolds such as polymer scaffolds, pre-formed extracellular matrix layers, or any other type of pre-formed scaffold at the time of manufacture or at the time of use. In some embodiments, the engineered tissues are substantially free of any pre-formed scaffolds. In further embodiments, the cellular components of the tissues contain a detectable, but trace or trivial amount of scaffold, e.g., less than 2.0%, less than 1.0%, or less than 0.5% of the total composition. In still further embodiments, trace or trivial amounts of scaffold are insufficient to affect long-term behavior of the tissue, or array thereof, or interfere with its primary biological function. In additional embodiments, scaffold components are removed post-printing, by physical, chemical, or enzymatic methods, yielding an engineered tissue that is free or substantially-free of scaffold components.

In some embodiments, the engineered tissues free, or substantially free, of pre-formed scaffold disclosed herein are in stark contrast to those developed with certain other methods of tissue engineering in which a scaffolding material is first formed, and then cells are seeded onto the scaffold, and subsequently the cells proliferate to fill and take the shape of the scaffold for example. In one aspect, the methods of bioprinting described herein allow production of viable and useful tissues that are free or substantially free of pre-formed scaffold. In another aspect, the cells of the invention are, in some embodiments, held in a desired three-dimensional shape using a confinement material. The confinement material is distinct from a scaffold at least in the fact that the confinement material is temporary and/or removable from the cells and/or tissue.

Arrays

In some embodiments, disclosed herein are arrays of engineered tissues, including vascular wall segments. In some embodiments, an "array" is a scientific tool including an association of multiple elements spatially arranged to allow a plurality of tests to be performed on a sample, one or more tests to be performed on a plurality of samples, or both. In some embodiments, the arrays are adapted for, or compatible with, screening methods and devices, including those associated with medium- or high-throughput screening. In further embodiments, an array allows a plurality of tests to be performed simultaneously. In further embodiments, an array allows a plurality of samples to be tested simultaneously. In some embodiments, the arrays are cellular microarrays. In further embodiments, a cellular microarray is a laboratory tool that allows for the multiplex interrogation of living cells on the surface of a solid support. In other embodiments, the arrays are tissue microarrays. In further embodiments, tissue microarrays include a plurality of separate tissues or tissue samples assembled in an array to allow the performance of multiple biochemical, metabolic, molecular, or histological analyses.

Figure 14:
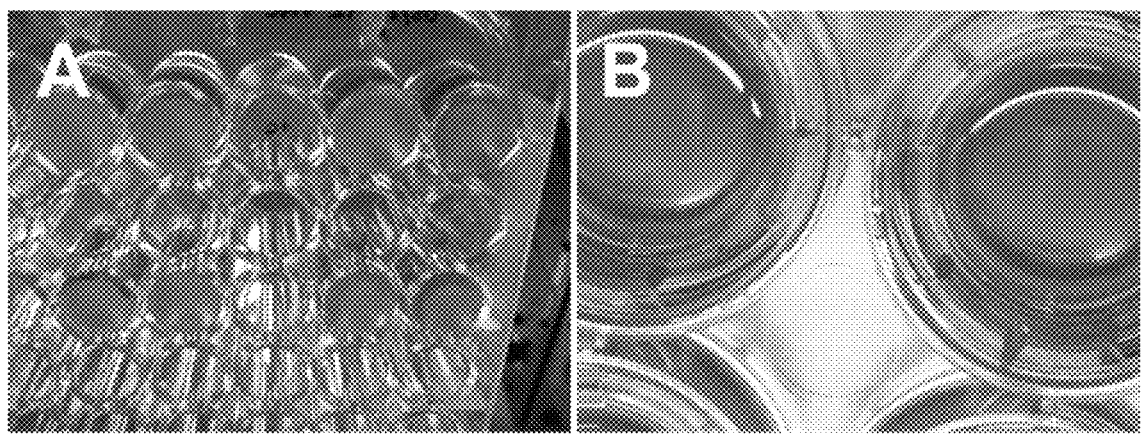
FIG. 14 is a pair of non-limiting macroscopic photographs depicting tissues bioprinted in multi-well plates (A) or within multi-well cell culture inserts (B). Bioprinted tissue constructs are generated in multi-well plates (A) or within multi-well culture inserts (B), which are optionally placed in an appropriate multi-well plate for long-term maintenance and maturation. Here, tissue constructs were bioprinted in a 24-well polystyrene plate (A) and on the porous membrane of a 6-well cell culture insert (B).

In some embodiments, the engineered tissues, including vascular wall segments each exist in a well of a biocompatible multi-well container (see, e.g., FIG. 14). In some embodiments, each tissue is placed into a well. In other embodiments, each tissue is bioprinted into a well. In further embodiments, the wells are coated. In various further embodiments, the wells are coated with one or more of: a biocompatible hydrogel, one or more proteins, one or more chemicals, one or more peptides, one or more antibodies, and one or more growth factors, including combinations thereof. In some embodiments, the wells are coated with NovoGel™. In other embodiments, the wells are coated with agarose. In some embodiments, each tissue exists on a porous, biocompatible membrane within a well of a biocompatible multi-well container. In some embodiments, each well of a multi-well container contains two or more tissues.

In some embodiments, the engineered tissues, including vascular wall segments are secured to a biocompatible surface on one or more sides. Many methods are suitable to secure a tissue to a biocompatible surface. In various embodiments, a tissue is suitably secured to a biocompatible surface, for example, along one or more entire sides, only at the edges of one or more sides, or only at the center of one or more sides. In various further embodiments, a tissue is suitably secured to a biocompatible surface with a holder or carrier integrated into the surface or associated with the surface. In various further embodiments, a tissue is suitably secured to a biocompatible surface with one or more pinchclamps or plastic nubs integrated into the surface or associated with the surface. In some embodiments, a tissue is suitably secured to a biocompatible surface by cell-attachment to a porous membrane. In some embodiments, the engineered tissues, including vascular wall segments are held in an array configuration by affixation to a biocompatible surface on one or more sides. In further embodiments, the tissue is affixed to a biocompatible surface on 1, 2, 3, 4, or more sides. In some embodiments, the biocompatible surface any surface that does not pose a significant risk of injury or toxicity to the tissue or an organism contacting the tissue. In further embodiments, the biocompatible surface is any surface suitable for traditional tissue culture methods. Suitable biocompatible surfaces include, by way of non-limiting examples, treated plastics, membranes, porous membranes, coated membranes, coated plastics, metals, coated metals, glass, treated glass, and coated glass, wherein suitable coatings include hydrogels, ECM components, chemicals, proteins, etc., and coatings or treatments provide a means to stimulate or prevent cell and tissue adhesion to the biocompatible surface.

In some embodiments, securing of an engineered tissue to a biocompatible surface on one or more sides facilitates subjecting the tissue to shear force, caused by fluid flow. In further embodiments, the engineered tissues, including vascular wall segments, are subjected to shear force, caused by fluid flow. In various embodiments, the engineered tissues are subjected to shear force on 1, 2, 3, 4, or more sides (see, e.g., FIG. 13).

In some embodiments, the arrays of engineered tissues, including vascular wall segments, comprise an association of two or more elements. In various embodiments, the arrays comprise an association of 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, 125, 150, 175, 200, 225, 250, 275, 300, 325, 350, 375, 400, 425, 450, 475, or 500 elements, including increments therein. In further embodiments, each element comprises one or more cells, multicellular aggregates, tissues, organs, or combinations thereof.

In some embodiments, the arrays of engineered tissues, including vascular wall segments, comprise multiple elements spatially arranged in a pre-determined pattern. In further embodiments, the pattern is any suitable spatial arrangement of elements. In various embodiments, patterns of arrangement include, by way of non-limiting examples, a two-dimensional grid, a three-dimensional grid, one or more lines, arcs, or circles, a series of rows or columns, and the like. In further embodiments, the pattern is chosen for compatibility with high-throughput biological assay or screening methods or devices.

In various embodiments, the cell types and/or source of the cells used to fabricate one or more tissues in an array are selected based on a specific research goal or objective. In further various embodiments, the specific tissues in an array are selected based on a specific research goal or objective. In some embodiments, one or more specific engineered tissues are included in an array to facilitate investigation of a particular disease or condition. In some embodiments, one or more specific engineered tissues are included in an array to facilitate investigation of a disease or a condition of a particular subject. In further embodiments, one or more specific engineered tissues within the array are generated with one or more cell types derived from two or more distinct human donors. In some embodiments, each tissue within the array is substantially similar with regard to cell types, sources of cells, layers of cells, ratios of cells, methods of construction, size, shape, and the like. In other embodiments, one or more of the tissues within the array is unique with regard to cell types, sources of cells, layers of cells, ratios of cells, methods of construction, size, shape, and the like. In various embodiments, 1, 2, 3, 4, 5, 6, 7, 8, 9, 10, 15, 20, 25, 30, 35, 40, 45, 50, 55, 60, 65, 70, 75, 80, 85, 90, 95, 100, 125, 150, 175, 200, 225, 250, 275, 300, or more of the tissues within the array, including increments therein, is/are unique. In other various embodiments, 1, 2, 3, 4, 5, 6, 7, 8, 9, 10, 15, 20, 25, 30, 35, 40, 45, 50, 55, 60, 65, 70, 75, 80, 85, 90, 91, 92, 93, 94, 95, 96, 97, 98, 99, or 100% of the tissues within the array, including increments therein, is/are unique.

In some embodiments, one or more tissues within an array represent one or more specific tissues in the human body. In further embodiments, one or more individual tissues within an array represent human tissues including, by way of non-limiting example, blood or lymph vessel, muscle, uterus, nerve, mucous membrane, mesothelium, omentum, cornea, skin, liver, kidney, heart, trachea, lung, bone, bone marrow, adipose, connective tissue, bladder, breast, pancreas, spleen, brain, esophagus, stomach, intestine, colon, rectum, ovary, prostate, tumor, endoderm, ectoderm, and mesoderm. In one embodiment, the tissues within an array are selected to represent all the major tissue types in a subject.

In some embodiments, each tissue within the array is maintained independently in culture. In further embodiments, the culture conditions of each tissue within the array are such that they are isolated from the other tissues and cannot exchange media or factors soluble in the media. In other embodiments, two or more individual tissues within the array exchange soluble factors. In further embodiments, the culture conditions of two or more individual tissues within the array are such that they exchange media and factors soluble in the media with other tissues. In various embodiments, 1, 2, 3, 4, 5, 6, 7, 8, 9, 10, 15, 20, 25, 30, 35, 40, 45, 50, 55, 60, 65, 70, 75, 80, 85, 90, 95, 100, 125, 150, 175, 200, 225, 250, 275, 300, or more of the tissues within the array, including increments therein, exchange media and/or soluble factors. In other various embodiments, 1, 2, 3, 4, 5, 6, 7, 8, 9, 10, 15, 20, 25, 30, 35, 40, 45, 50, 55, 60, 65, 70, 75, 80, 85, 90, 91, 92, 93, 94, 95, 96, 97, 98, 99, or 100% of the tissues within the array, including increments therein, exchange media and/or soluble factors.

In Vitro Assays

In some embodiments, the engineered tissues, including vascular wall segments, and arrays disclosed herein are for use in in vitro assays. In some embodiments, an "assay" is a procedure for testing or measuring the presence or activity of a substance (e.g., a chemical, molecule, biochemical, drug, etc.) in an organic or biologic sample (e.g., cell aggregate, tissue, organ, organism, etc.). In further embodiments, assays include qualitative assays and quantitative assays. In still further embodiments, a quantitative assay measures the amount of a substance in a sample.

In various embodiments, the engineered tissues, including vascular wall segments and arrays are for use in, by way of non-limiting examples, image-based assays, measurement of secreted proteins, expression of markers, and production of proteins. In various further embodiments, the engineered tissues, including vascular wall segments, and arrays are for use in assays to detect or measure one or more of: molecular binding (including radioligand binding), molecular uptake, activity (e.g., enzymatic activity and receptor activity, etc.), gene expression, protein expression, receptor agonism, receptor antagonism, cell signaling, apoptosis, chemosensitivity, transfection, cell migration, chemotaxis, cell viability, cell proliferation, safety, efficacy, metabolism, toxicity, and abuse liability.

In some embodiments, the engineered tissues, including vascular wall segments, and arrays are for use in immunoassays. In further embodiments, immunoassays are competitive immunoassays or noncompetitive immunoassays. In a competitive immunoassay, for example, the antigen in a sample competes with labeled antigen to bind with antibodies and the amount of labeled antigen bound to the antibody site is then measured. In a noncompetitive immunoassay (also referred to as a "sandwich assay"), for example, antigen in a sample is bound to an antibody site; subsequently, labeled antibody is bound to the antigen and the amount of labeled antibody on the site is then measured.

In some embodiments, the engineered tissues, including vascular wall segments, and arrays are for use in enzyme-linked immunosorbent assays (ELISA). In further embodiments, an ELISA is a biochemical technique used to detect the presence of an antibody or an antigen in a sample. In ELISA, for example, at least one antibody with specificity for a particular antigen is utilized. By way of further example, a sample with an unknown amount of antigen is immobilized on a solid support (e.g., a polystyrene microtiter plate) either non-specifically (via adsorption to the surface) or specifically (via capture by another antibody specific to the same antigen, in a "sandwich" ELISA). By way of still further example, after the antigen is immobilized, the detection antibody is added, forming a complex with the antigen. The detection antibody is, for example, covalently linked to an enzyme, or is itself detected by a secondary antibody that is linked to an enzyme through bioconjugation.

For example, in some embodiments, an array, microarray, or chip of cells, multicellular aggregates, or tissues is used for drug screening or drug discovery. In further embodiments, an array, microarray, or chip of tissues is used as part of a kit for drug screening or drug discovery. In some embodiments, each vascular wall segment exists within a well of a biocompatible multi-well container, wherein the container is compatible with one or more automated drug screening procedures and/or devices. In further embodiments, automated drug screening procedures and/or devices include any suitable procedure or device that is computer or robot-assisted.

In further embodiments, arrays for drug screening assays or drug discovery assays are used to research or develop drugs potentially useful in any therapeutic area. In still further embodiments, suitable therapeutic areas include, by way of non-limiting examples, infectious disease, hematology, oncology, pediatrics, cardiology, central nervous system disease, neurology, gastroenterology, hepatology, urology, infertility, ophthalmology, nephrology, orthopedics, pain control, psychiatry, pulmonology, vaccines, wound healing, physiology, pharmacology, dermatology, gene therapy, toxicology, and immunology.

Methods

Disclosed herein, in some embodiments, are methods for constructing a living, three-dimensional tissue construct comprising the steps of bioprinting bio-ink comprising at least one adherent cell type into or onto a form, and fusing of the bio-ink into a living, three-dimensional tissue construct. In further embodiments, the tissue construct is for in vitro use. In still further embodiments, the tissue construct is not a vascular tube.

Also disclosed herein, in some embodiments, are methods of constructing tissues, including vascular wall segments, comprising the steps of: preparing cohered multicellular aggregates comprising smooth muscle cells; placing said cohered multicellular aggregates onto a support; and incubating said multicellular aggregates to allow them to cohere and form a tissue such as a vascular wall segment; wherein said incubation has a duration of about 2 hours to about 10 days. In some embodiments, the methods utilize bioprinting. In further embodiments, the methods produce engineered tissues, including vascular wall segments, free or substantially free of any pre-formed scaffold.

Also disclosed herein, in some embodiments, are methods of constructing living, three-dimensional tissues, including vascular wall segments, comprising the steps of: preparing one or more cohered multicellular aggregates comprising mammalian cells; placing said one or more cohered multicellular aggregates onto a support; applying, to said one or more cohered multicellular aggregates, one or more of: a layer of a first type of mammalian cells on one or more external surfaces; a layer of a second type of mammalian cells on one or more external surfaces; and incubating said one or more multicellular aggregates to allow them to cohere and to form a tissue; wherein said incubation has a duration of about 2 hours to about 10 days. In some embodiments, the methods utilize bioprinting. In further embodiments, the methods produce engineered tissues, including vascular wall segments, free or substantially free of any pre-formed scaffold.

Also disclosed herein, in some embodiments, are methods of constructing living, three-dimensional tissue constructs comprising the steps of: preparing one or more cohered multicellular aggregates comprising mammalian cells; placing said one or more cohered multicellular aggregates onto a support to form at least one of: at least one layer comprising a plurality of cell types, the cell types spatially arranged relative to each other to create a planar geometry; and a plurality of layers, at least one layer compositionally or architecturally distinct from at least one other layer to create a laminar geometry; and incubating said one or more multicellular aggregates to allow them to cohere and to form a living, three-dimensional tissue construct.

Preparing Cohered Multicellular Aggregates

In some embodiments, the methods involve preparing cohered multicellular aggregates comprising one or more types of mammalian cells. In some embodiments, the methods involve preparing cohered multicellular aggregates comprising smooth muscle cells. In some embodiments, the methods involve preparing cohered multicellular aggregates further comprising endothelial cells. See, e.g., Examples 3, 4, and 7. In some embodiments, the methods involve preparing cohered multicellular aggregates further comprising fibroblasts. See, e.g., Examples 5 and 6.

There are various ways to make multicellular aggregates having the characteristics described herein. In some embodiments, a multicellular aggregate is fabricated from a cell paste containing a plurality of living cells or with a desired cell density and viscosity. In further embodiments, the cell paste is shaped into a desired shape and a multicellular body formed through maturation (e.g., incubation). In some embodiments, the multicellular aggregates are substantially cylindrical. In some embodiments, the multicellular aggregates are substantially ribbon-shaped. In some embodiments, the multicellular aggregates are substantially spherical. In other embodiments, the engineered tissues are constructed from multicellular aggregates with a range of shapes. In a particular embodiment, an elongate multicellular body is produced by shaping a cell paste including a plurality of living cells into an elongate shape (e.g., a cylinder, a ribbon, etc.). In further embodiments, the cell paste is incubated in a controlled environment to allow the cells to adhere and/or cohere to one another to form the elongate multicellular body. In another particular embodiment, a multicellular body is produced by shaping a cell paste including a plurality of living cells in a device that holds the cell paste in a three-dimensional shape. In further embodiments, the cell paste is incubated in a controlled environment while it is held in the three dimensional shape for a sufficient time to produce a body that has sufficient cohesion to support itself on a flat surface.

In various embodiments, a cell paste is provided by: 1) collecting cells or cell aggregates (of one or more cell types) and a biocompatible gel or liquid, such as cell culture medium (e.g., in a pre-determined ratio) to result in a cell suspension, and 2) compacting the cellular suspension to produce a cell paste with a desired cell density and viscosity. In various embodiments, compacting is achieved by a number of methods, such as by concentrating a particular cell suspension that resulted from cell culture to achieve the desired cell concentration (density), viscosity, and consistency required for the cell paste. In a particular embodiment, a relatively dilute cell suspension from cell culture is centrifuged for a determined time to achieve a cell concentration in the pellet that allows shaping in a mold. Tangential flow filtration ("TFF") is another suitable method of concentrating or compacting the cells. In some embodiments, compounds are combined with the cell suspension to lend the extrusion properties required. Suitable compounds include, by way of non-limiting examples, surfactant polyols, collagens, hydrogels, peptide hydrogels, amino acid-based gels, Matrigel™, nanofibers, self-assembling nanofibers, gelatin, fibrinogen, etc.

In some embodiments, the cell paste is produced by mixing a plurality of living cells with a tissue culture medium, and compacting the living cells (e.g., by centrifugation). One or more ECM components (or derivative of an ECM component) is optionally included by, resuspending the cell pellet in one or more physiologically acceptable buffers containing the ECM component(s) (or derivative(s) of ECM component(s)) and the resulting cell suspension centrifuged again to form a cell paste.

In some embodiments, the cell density of the cell paste desired for further processing varies with cell types. In further embodiments, interactions between cells determine the properties of the cell paste, and different cell types will have a different relationship between cell density and cell-cell interaction. In still further embodiments, the cells are pre-treated to increase cellular interactions before shaping the cell paste. For example, in some cases, cells are incubated inside a centrifuge tube after centrifugation in order to enhance cell-cell interactions prior to shaping the cell paste. In some embodiments, the cell paste is shaped concomitantly with bioprinting; wherein the cohesion of individual cells to each other to form bio-ink occurs during or after bioprinting.

In various embodiments, many methods are used to shape the cell paste. For example, in a particular embodiment, the cell paste is manually molded or pressed (e.g., after concentration/compaction) to achieve a desired shape. By way of a further example, the cell paste is taken up (e.g., aspirated) into an instrument, such as a micropipette (e.g., a capillary pipette), that shapes the cell paste to conform to an interior surface of the instrument. The cross-sectional shape of the micropipette (e.g., capillary pipette) is alternatively circular, square, rectangular, triangular, or other non-circular cross-sectional shape. In some embodiments, the cell paste is shaped by depositing it into a preformed mold, such as a plastic mold, metal mold, or a gel mold. In some embodiments, centrifugal casting or continuous casting is used to shape the cell paste. In some embodiments, the shaping of the bio-ink occurs concomitantly or after bioprinting. In further embodiments, the shaping of the bio-ink occurs as the result of a co-printed mold; wherein the mold is optionally deposited via bioprinting; wherein the mold comprises one or more of: gel, hydrogel, synthetic polymer, carbohydrate, protein, or mammalian cells. In still further embodiments, one or more components of the co-printed mold are removed after bioprinting; wherein the removal method is selected from one of: physical means, solubilization with aqueous media; chemical treatment; enzymatic treatment; modulating temperature.

In some embodiments, multicellular aggregates of a defined shape are also suitable to build the tissues, including vascular wall segments, described herein. Spherical multicellular aggregates are optionally generated by a variety of methods, including, but not limited to, cellular self-assembly, the use of molds, and hanging drop methods. In further embodiments, a method to produce substantially spherical multicellular aggregates comprises the steps of 1) providing a cell paste containing a plurality of pre-selected cells or cell aggregates with a desired cell density and viscosity, 2) manipulating the cell paste into a cylindrical shape, 3) cutting cylinders into equal fragments, 4) optionally letting the fragments round up overnight on a gyratory shaker, and 5) forming the substantially spherical multicellular aggregates through maturation. In further embodiments, cellular aggregates are generated via acoustic focusing methodologies.

In some embodiments, a partially adhered and/or cohered cell paste is used for bioprinting; wherein cohesion and bio-ink formation occurs primarily post-printing. In other embodiments, the cellular paste is shaped in a first step prior to bioprinting. In further embodiments, the cell paste is transferred from the first shaping device (e.g., capillary pipette) to a second shaping device (e.g., a mold) that allows nutrients and/or oxygen to be supplied to the cells while they are retained in the second shaping device for an additional maturation period. One example of a suitable shaping device that allows the cells to be supplied with nutrients and oxygen is a mold for producing a plurality of multicellular aggregates (e.g., substantially identical multicellular aggregates). By way of further example, such a mold includes a biocompatible substrate made of a material that is resistant to migration and ingrowth of cells into the substrate and resistant to adherence of cells to the substrate. In various embodiments, the substrate is suitably be made of Teflon® (PTFE), stainless steel, NovoGel™, agarose, polyethylene glycol, glass, metal, plastic, or gel materials (e.g., agarose or other hydrogels), and similar materials. In some embodiments, the mold is also suitably configured to allow supplying tissue culture media to the cell paste (e.g., by dispensing tissue culture media onto the top of the mold).

Thus, in embodiments where a second shaping device is used, the partially adhered and/or cohered cell paste is transferred from the first shaping device (e.g., a capillary pipette) to the second shaping device (e.g., a mold). In further embodiments, the partially adhered and/or cohered cell paste is transferred by the first shaping device (e.g., the capillary pipette) into the grooves of a mold. In still further embodiments, following a maturation period in which the mold is incubated along with the cell paste retained therein in a controlled environment to allow the cells in the cell paste to further adhere and/or cohere to one another to form the multicellular aggregate, the cohesion of the cells will be sufficiently strong to allow the resulting multicellular aggregate to be picked up with an implement (e.g., a capillary pipette). In still further embodiments, the capillary pipette is suitably be part of a printing head of a bioprinter or similar apparatus operable to automatically place the multicellular aggregate into a three-dimensional construct.

In some embodiments, the cross-sectional shape and size of the multicellular aggregates will substantially correspond to the cross-sectional shapes and sizes of the first shaping device and optionally the second shaping device used to make the multicellular aggregates, and the skilled artisan will be able to select suitable shaping devices having suitable cross-sectional shapes, cross-sectional areas, diameters, and lengths suitable for creating multicellular aggregates having the cross-sectional shapes, cross-sectional areas, diameters, and lengths discussed above.

Placing Cohered Multicellular Aggregates onto a Support

A number of methods are suitable to place multicellular aggregates on a support to produce a desired three-dimensional structure. For example, in some embodiments, the multicellular aggregates are manually placed in contact with one another, deposited in place by extrusion from a pipette, nozzle, or needle, or positioned by an automated, computer-assisted device such as a bioprinter.

As described herein, in various embodiments, multicellular aggregates have many suitable shapes and sizes. In some embodiments, multicellular aggregates are elongate with any of several suitable cross-sectional shapes including, by way of non-limiting example, circular, oval, square, triangular, polygonal, and irregular. In further embodiments, multicellular aggregates are elongate and in the form of a cylinder. In some embodiments, elongate multicellular aggregates are of similar lengths and/or diameters. In other embodiments, elongate multicellular aggregates are of differing lengths and/or diameters. In some embodiments, multicellular aggregates are substantially spherical. In some embodiments, the engineered tissues (e.g., vascular wall segments, etc.) include substantially spherical multicellular aggregates that are substantially similar in size. In other embodiments, the engineered tissues (e.g., vascular wall segments, etc.) include substantially spherical multicellular aggregates that are of differing sizes. In some embodiments, engineered tissues (e.g., vascular wall segments, etc.) of different shapes and sizes are formed by arranging multicellular aggregates of various shapes and sizes.

In some embodiments, the cohered multicellular aggregates are placed onto a support. In various embodiments, the support is any suitable biocompatible surface. In still further embodiments, suitable biocompatible surfaces include, by way of non-limiting examples, polymeric material, porous membranes, plastic, glass, metal, hydrogel, and combinations thereof. In some embodiments, the support is coated with a biocompatible substance including, by way of non-limiting examples, a hydrogel, a protein, a chemical, a peptide, antibodies, growth factors, or combinations thereof. In one embodiment, the support is coated with NovoGel™. In another embodiment, the support is coated with agarose. In one embodiment, the cohered multicellular aggregates are placed into the wells of a biocompatible multi-well container.

Once placement of the cohered multicellular aggregates is complete, in some embodiments, a tissue culture medium is poured over the top of the construct. In further embodiments, the tissue culture medium enters the spaces between the multicellular bodies to support the cells in the multicellular bodies.

Applying a Layer of a First Type of Cells and/or a Layer of a Second Type of Cells A number of methods are suitable to apply one or more layers of cells on one or more external surfaces of the cohered mammalian cell construct. For example, in some embodiments, applying a layer of cells comprises coating one or more surfaces of said cohered multicellular aggregates with a suspension, sheet, monolayer, or fused aggregates of cells. In various embodiments, 1, 2, 3, 4, or more surfaces of the cohered mammalian cell construct are coated.

In some embodiments, applying a layer of cells comprises bioprinting an additional layer of fused multicellular aggregates. In other embodiments, applying a layer of cells comprises bioprinting, spraying, or ink-jetting a solution, suspension, or liquid concentrate of cells. In further embodiments, a suitable cell suspension comprises about $1 \times 10^4$ to about $1 \times 10^6$ cells/W. In still further embodiments, a suitable cell suspension comprises about $1 \times 10^5$ to about $1.5 \times 10^5$ cells/W. In further embodiments, applying a layer of cells comprises dispensing a suspension of cells directly onto one or more surfaces of the cohered mammalian cell construct as spatially-distributed droplets. In still further embodiments, applying a layer of cells comprises dispensing a suspension of cells directly onto one or more surfaces of the cohered mammalian cell construct as a spray. Layers of cells are, in various embodiments, applied at any suitable time in the construction process. In some embodiments, one or more layers of cells are applied on one or more external surfaces of the cohered mammalian cell construct immediately after bioprinting (e.g., up to 10 min.). In other embodiments, one or more layers are applied after bioprinting (e.g., after 10 min.). In yet other embodiments, one or more layers are applied during maturation of the construct.

Any type of cell is suitable for application as a layer by bioprinting as bio-ink. Moreover, any type of cell is suitable for application as a layer by deposition as droplets of suspension, solution, or concentrate, or spraying as a suspension, solution, or concentrate. In some embodiments, fibroblasts are applied as one or more layers of cells on one or more external surfaces of the cohered mammalian cell construct. In other embodiments, endothelial cells are applied as one or more layers of cells on one or more external surfaces of the cohered mammalian cell construct. In further embodiments, a layer of endothelial cells is applied to one or more external surfaces of the cohered mammalian cell construct and a layer of fibroblasts is applied to one or more distinct surfaces of the construct.

Example 9 demonstrates vascular wall constructs bioprinted with cohered smooth muscle cell aggregates, which were further coated with an endothelial cell concentrate (e.g., $1$-$1.5 \times 10^5$ cells/μl). The techniques of Example 9 resulted in a vascular wall construct comprised of SMC and a covering of EC (e.g., a putative tunica media and tunica intima). See, e.g., FIGS. 3, 4B.

Example 10 demonstrates vascular wall constructs bioprinted with cohered human aortic smooth muscle cell aggregates. Further, human aortic endothelial cells in suspension were dispensed from a bioprinter on top of the smooth muscle cylindrical bio-ink as 2.5 μL droplets.

In some embodiments, the methods further comprise the step of culturing a layer of cells on a support. In such embodiments, applying a layer of cells, in some cases, comprises placing one or more surfaces of the cohered smooth muscle cell construct in direct contact with an established culture of cells. In further embodiments, the construct is bioprinted directly onto a cultured layer of cells or a monolayer of cells. Any type of cultured cell layer on a biocompatible support is suitable. In some embodiments, multicellular aggregates are bioprinted onto a layer of endothelial cells. In other embodiments, multicellular aggregates are bioprinted onto a layer of fibroblasts. In further embodiments, the layer of cells adheres and/or coheres with the multicellular aggregates of the bioprinted construct. In some embodiments, each layer of a multi-layered structure are bioprinted. In further embodiments, the individual layers comprise variable forms of bio-ink, including but not limited to: cohered cell aggregates, cell paste, cell paste in combination with extrusion compound(s) or other additives, cell monolayers, and cell sheets.

Example 11 demonstrates construction of the same constructs of Example 10; however, the constructs were bioprinted onto a support on which a confluent monolayer of human dermal fibroblasts had been pre-cultured. The techniques of Example 11 resulted in a vascular wall construct comprised of SMC and coverings of EC and Fb (e.g., a putative tunica media, tunica intima, and tunica adventitia). See, e.g., FIGS. 4a and 4b.

Incubating Multicellular Aggregates

In some embodiments, the multicellular aggregates are incubated. In further embodiments, the incubation allows the multicellular aggregates adhere and/or cohere to form a tissue, such as a vascular wall segment. In some embodiments, the multicellular aggregates cohere to form a tissue in a cell culture environment (e.g., a Petri dish, cell culture flask, bioreactor, etc.). In further embodiments, the multicellular aggregates cohere to form a tissue in an environment with conditions suitable to facilitate growth of the cell types included in the multicellular aggregates. In one embodiment, the multicellular aggregates are incubated at about 37° C., in a humidified atmosphere containing about 5% $CO_2$, in the presence of cell culture medium containing factors and/or ions to foster adherence and/or coherence. In other embodiments, the multicellular aggregates are maintained in an environment that contains 0.1% to 21% $O_2$.

The incubation, in various embodiments, has any suitable duration. In further various embodiments, the incubation has a duration of about 20, 30, 40, 50, 60, 70, 80, 90, 100, 110, 120, 130, 140, 150, 160, 170, 180, or more minutes, including increments therein. In further various embodiments, the incubation has a duration of about 1, 2, 3, 4, 5, 6, 7, 8, 9, 10, 11, 12, 13, 14, 15, 16, 17, 18, 19, 20, 21, 22, 23, 24, 36, 48, or more hours, including increments therein. In further various embodiments, the incubation has a duration of about 1, 2, 3, 4, 5, 6, 7, 8, 9, 10, 11, 12, 13, 14, 15, 16, 17, 18, 19, 20, or more days, including increments therein. Several factors influence the time required for multicellular aggregates to cohere to form a tissue including, by way of non-limiting examples, cell types, cell type ratios, culture conditions, and the presence of additives such as growth factors.

Additional Steps for Increasing Viability of the Engineered Tissue

In some embodiments, the method further comprises steps for increasing the viability of the engineered tissue. In further embodiments, these steps involve providing direct contact between the tissue and a nutrient medium through a temporary or semi-permanent lattice of confinement material. In some embodiments, the tissue is constrained in a porous or gapped material. Direct access of at least some of the cells of the engineered tissue to nutrients increases the viability of the engineered tissue.

Figure 5:
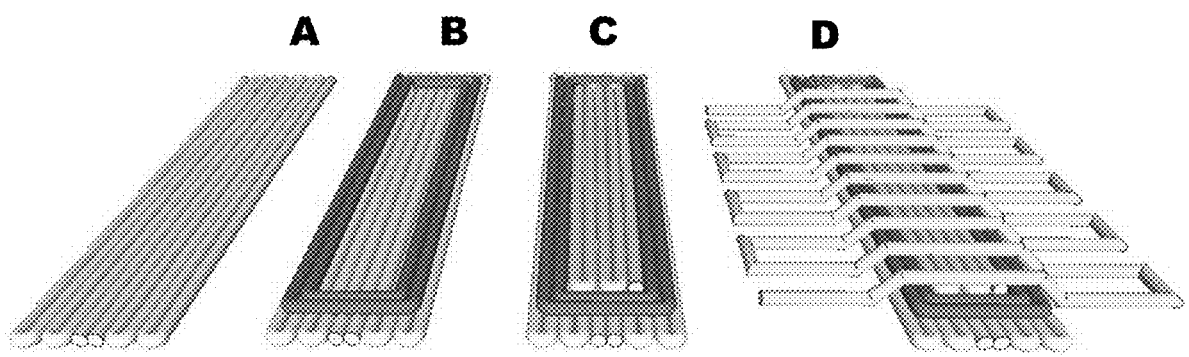
FIG. 5 is a non-limiting example of a bioprinted cell sheet and a temporary or removable bioprinted confinement lattice structure; also depicted are exemplary steps for fabricating the same. A simple example of a lattice structure printed on the top surface of a three-dimensional cell sheet. (A) Optionally dispensing base layer of confinement material. (B) Optionally dispensing a perimeter of confinement material. (C) Bioprinting cells within a defined geometry. (D) Dispensing cylinders of confinement material overlaying the cells.

In further embodiments, the additional and optional steps for increasing the viability of the engineered tissue include: 1) optionally dispensing base layer of confinement material prior to placing cohered multicellular aggregates; 2) optionally dispensing a perimeter of confinement material; 3) bioprinting cells of the tissue within a defined geometry; and 4) dispensing elongate bodies (e.g., cylinders, ribbons, etc.) of confinement material overlaying the nascent tissue in a pattern that introduces gaps in the confinement material, such as a lattice, mesh, or grid. See, e.g., Example 12 and FIG. 5.

Many confinement materials are suitable for use in the methods described herein. In some embodiments, hydrogels are exemplary confinement materials possessing one or more advantageous properties including: non-adherent, biocompatible, extrudable, bioprintable, non-cellular, of suitable strength, and not soluble in aqueous conditions. In some embodiments, suitable hydrogels are natural polymers. In one embodiment, the confinement material is comprised of NovoGel™. In further embodiments, suitable hydrogels include those derived from surfactant polyols such as Pluronic F-127, collagen, hyaluronate, fibrin, alginate, agarose, chitosan, and derivatives or combinations thereof. In other embodiments, suitable hydrogels are synthetic polymers. In further embodiments, suitable hydrogels include those derived from poly(acrylic acid) and derivatives thereof, poly(ethylene oxide) and copolymers thereof, poly (vinyl alcohol), polyphosphazene, and combinations thereof. In various specific embodiments, the confinement material is selected from: hydrogel, NovoGel™, agarose, alginate, gelatin, Matrigel™, hyaluronan, poloxamer, peptide hydrogel, poly(isopropyl n-polyacrylamide), polyethylene glycol diacrylate (PEG-DA), hydroxyethyl methacrylate, polydimethylsiloxane, polyacrylamide, poly(lactic acid), silicon, silk, and combinations thereof.

In some embodiments, the gaps overlaying pattern are distributed uniformly or substantially uniformly around the surface of the tissue. In other embodiments, the gaps are distributed non-uniformly, whereby the cells of the tissue are exposed to nutrients non-uniformly. In non-uniform embodiments, the differential access to nutrients is optionally exploited to influence one or more properties of the tissue. For instance, in some cases, it is desirable to have cells on one surface of a bioprinted tissue proliferate faster than cells on another surface of the bioprinted tissue. In some embodiments, the exposure of various parts of the tissue to nutrients is changed at various times to influence the development of the tissue toward a desired endpoint.

In some embodiments, the confinement material is removed at any suitable time, including but not limited to, immediately after bioprinting (e.g., within 10 minutes), after bioprinting (e.g., after 10 minutes), before the cells are substantially cohered to each other, after the cells are substantially cohered to each other, before the cells produce an extracellular matrix, after the cells produce an extracellular matrix, just prior to use, and the like. In various embodiments, confinement material is removed by any suitable method. For example, in some embodiments, the confinement material is excised, pulled off the cells, digested, or dissolved.

In some embodiments, the methods further comprise the step of subjecting the engineered tissue (e.g., vascular wall segment, etc.) to shear force, caused by fluid flow, on one or more sides.

Particular Exemplary Embodiments

In certain embodiments, disclosed herein are living, three-dimensional tissues wherein at least one component of said tissue was bioprinted; and wherein said tissue is not a vascular tube. In some embodiments, the tissue is substantially free of any pre-formed scaffold. In some embodiments, the tissue is substantially free of any pre-formed scaffold at the time of bioprinting. In some embodiments, the tissue is substantially free of any pre-formed scaffold at the time of use. In some embodiments, at least one component of the tissue comprises a laminar or planar geometry. In some embodiments, the tissue is secured to a biocompatible surface on one or more sides. In further embodiments, the biocompatible surface is a porous membrane. In further embodiments, the tissue is subjected to shear force, caused by fluid flow, on one or more sides. In some embodiments, the tissue is at least about 25 µm in its smallest dimension at the time of bioprinting. In further embodiments, the tissue is at least about 100 µm in its smallest dimension at the time of bioprinting. In still further embodiments, the tissue is at least about 250 µm in its smallest dimension at the time of bioprinting. In still further embodiments, the tissue is at least about 500 µm in its smallest dimension at the time of bioprinting. In some embodiments, the tissue is less than 3.0 cm in its largest dimension at the time of bioprinting. In some embodiments, the tissue comprises smooth muscle cells and endothelial cells, wherein the ratio of smooth muscle cells to endothelial cells is about 90:10 to about 60:40. In some embodiments, the tissue comprises smooth muscle cells and endothelial cells, wherein the ratio of smooth muscle cells to endothelial cells is about 85:15. In some embodiments, the tissue comprises smooth muscle cells and endothelial cells, wherein the ratio of smooth muscle cells to endothelial cells is about 70:30. In some embodiments, the tissue comprises smooth muscle cells and fibroblasts, wherein the ration of smooth muscle cells to fibroblasts is about 90:10 to about 60:40. In some embodiments, the tissue comprises smooth muscle cells, fibroblasts, and endothelial cells, wherein the ratio of smooth muscle cells to fibroblasts and endothelial cells is about 70:25:5. In some embodiments, the tissue is for use in in vitro assays. In further embodiments, the tissue is for use in drug testing. In still further embodiments, the tissue is for use in cardiovascular drug testing. In some embodiments, the smooth muscle cells, fibroblasts, and endothelial cells are adult, differentiated cells. In some embodiments, the smooth muscle cells, fibroblasts, and endothelial cells are adult, non-differentiated cells. In some embodiments, the smooth muscle cells are human smooth muscle cells. In further embodiments, the smooth muscle cells originated from a tissue selected from the group consisting of: blood, blood vessel, lymphatic vessel, tissue of the digestive tract, tissue of the genitourinary tract, adipose tissue, tissue of the respiratory tract, tissue of the reproductive system, mesoderm-derived tissue, bone marrow, and umbilical tissue. In some embodiments, the endothelial cells are human endothelial cells. In further embodiments, the endothelial cells originated from a tissue selected from the group consisting of: blood, blood vessel, lymphatic vessel, tissue of the digestive tract, tissue of the genitourinary tract, adipose tissue, tissue of the respiratory tract, tissue of the reproductive system, mesoderm-derived tissue, bone marrow, and umbilical tissue. In some embodiments, the fibroblasts are non-vascular fibroblasts. In other embodiments, the fibroblasts are derived from the vascular adventitia. In some embodiments, one or more of said cell types are derived from a particular vertebrate subject. In further embodiments, the cells are derived from a vertebrate subject that has a disease or condition that affects the cardiovascular system. In some embodiments, the cells are selected to mimic a particular disease state. In some embodiments, the cells are configured to mimic a particular disease state. In some embodiments, the cells are treated or modulated in a manner that mimics a particular disease state.

In certain embodiments, disclosed herein are arrays of living, three-dimensional, tissues, wherein each said tissue comprises one or more types of mammalian cells; wherein said cells are cohered to one another; wherein at least one component of each said tissue was bioprinted; and wherein each said tissue is maintained in culture. In some embodiments, each tissue within the array is free of any pre-formed scaffold at the time of use. In some embodiments, the mammalian cells are selected from the group consisting of: liver cells, gastrointestinal cells, pancreatic cells, kidney cells, lung cells, tracheal cells, vascular cells, skeletal muscle cells, cardiac cells, skin cells, smooth muscle cells, connective tissue cells, corneal cells, genitourinary cells, reproductive cells, endothelial cells, epithelial cells, fibroblasts, neural cells, Schwann cells, adipose cells, bone cells, bone marrow cells, cartilage cells, pericytes, mesenchymal cells, mesothelial cells, stromal cells, stem cells, progenitor cells, lymph cells, blood cells, tumor-derived cells, and combinations thereof. In some embodiments, each tissue within the array is substantially similar. In other embodiments, one or more of the tissues within the array is unique. In some embodiments, individual tissues within the array represent one or more specific tissues in the human body. In further embodiments, one or more individual tissues within the array represent human tissues selected from the group consisting of: blood or lymph vessel, muscle, uterus, nerve, mucous membrane, mesothelium, omentum, cornea, skin, liver, kidney, heart, trachea, lung, bone, bone marrow, adipose, connective, bladder, breast, pancreas, spleen, brain, esophagus, stomach, intestine, colon, rectum, ovary, and prostate; wherein each of the tissues optionally incorporates compositional or architectural features of specific disease states (e.g., fibrosis, cancer, inflammation, etc.). In some embodiments, each tissue exists in a well of a biocompatible multi-well container. In further embodiments, the wells are coated with one of or more of the following: a biocompatible hydrogel, a protein, a chemical, a peptide, antibodies, or growth factors. In still further embodiments, the wells are coated with agarose. In some embodiments, each tissue was placed onto a porous, biocompatible membrane within said wells of said container. In some embodiments, the container is compatible with automated drug screening. In some embodiments, each tissue is affixed to a biocompatible surface on one or more sides. In further embodiments, the biocompatible surface is a porous membrane. In still further embodiments, each tissue is subjected to shear force, caused by fluid flow, on one or more sides. In some embodiments, the tissues within the array are generated with one or more cell types derived from two or more distinct human donors. In some embodiments, each tissue within the array is maintained independently in culture. In other embodiments, two or more individual tissues within the array exchange soluble factors. In some embodiments, the array is for use in in vitro assays. In further embodiments, the array is for use in drug testing.

In certain embodiments, disclosed herein are methods of constructing an array of living, three-dimensional mammalian tissues comprising the steps of: preparing cohered multicellular aggregates comprising mammalian cells; placing said cohered multicellular aggregates onto a biocompatible support; wherein said aggregates are spatially arranged in a form suitable for a tissue array; and incubating said multicellular aggregates to allow them to cohere and form an array of three-dimensional tissues; wherein said incubation has a duration of about 2 hours to about 10 days. In some embodiments, at least one component of each tissue within the array was bioprinted. In further embodiments, each tissue within the array is substantially free of any pre-formed scaffold at the time of use. In various embodiments, the array comprises from 2 to 500 distinct tissues. In further embodiments, the tissues are spatially arranged in a defined pattern. In still further embodiments, the tissues are arranged in a grid of rows and columns. In some embodiments, the cohered multicellular aggregates comprise one cell type. In other embodiments, the cohered multicellular aggregates comprise more than one cell type. In some embodiments, the cohered multicellular aggregates are substantially spherical and/or substantially cylindrical. In some embodiments, the biocompatible support consists of: a polymeric material, a porous membrane, plastic, glass, metal, or hydrogel. In some embodiments, each tissue within the array is at least about 25 µm in its smallest dimension at the time of bioprinting. In further embodiments, each tissue is at least about 150 µm in its smallest dimension at the time of bioprinting. In still further embodiments, each tissue is at least about 250 µm in its smallest dimension at the time of bioprinting. In still further embodiments, each tissue is at least about 500 µm in its smallest dimension at the time of bioprinting. In some embodiments, each tissue within the array is maintained in culture. In some embodiments, the methods further comprise the step of subjecting each said tissue to shear force, caused by fluid flow, on one or more sides.

In certain embodiments, disclosed herein are living, three-dimensional vascular wall segments comprising: smooth muscle cells; and optionally, one or more cell types selected from the group consisting of: fibroblasts and endothelial cells; wherein said cells are cohered to one another; wherein at least one component of said vascular wall segment was bioprinted; and wherein said vascular wall segment is non-tubular. In some embodiments, the vascular wall segment is free of any pre-formed scaffold. In some embodiments, the vascular wall segment is substantially planar. In some embodiments, the vascular wall segment is affixed to a biocompatible surface on one or more sides. In further embodiments, the biocompatible surface is a porous membrane. In still further embodiments, the vascular wall segment is subjected to shear force, caused by fluid flow, on one or more sides. In some embodiments, the vascular wall segment is at least about 25 µm in its smallest dimension at the time of bioprinting. In further embodiments, the vascular wall segment is at least about 150 µm in its smallest dimension at the time of bioprinting. In still further embodiments, the vascular wall segment is at least about 250 µm in its smallest dimension at the time of bioprinting. In still further embodiments, the vascular wall segment is at least about 500 µm in its smallest dimension at the time of bioprinting. In some embodiments, the vascular wall segment comprises smooth muscle cells and endothelial cells, wherein the ratio of smooth muscle cells to endothelial cells is about 90:10 to about 60:40. In further embodiments, the vascular wall segment comprises smooth muscle cells and endothelial cells, wherein the ratio of smooth muscle cells to endothelial cells is about 85:15. In other embodiments, the vascular wall segment comprises smooth muscle cells and endothelial cells, wherein the ratio of smooth muscle cells to endothelial cells is about 70:30. In some embodiments, the vascular wall segment comprises smooth muscle cells and fibroblasts, wherein the ration of smooth muscle cells to fibroblasts is about 90:10 to about 60:40. In some embodiments, the vascular wall segment comprises smooth muscle cells, fibroblasts, and endothelial cells, wherein the ratio of smooth muscle cells to fibroblasts and endothelial cells is about 70:25:5. In some embodiments, the vascular wall segment is for use in in vitro assays. In further embodiments, the vascular wall segment is for use in drug testing. In still further embodiments, the vascular wall segment is for use in cardiovascular drug testing. In some embodiments, the smooth muscle cells, fibroblasts, and endothelial cells are adult, differentiated cells. In other embodiments, the smooth muscle cells, fibroblasts, and endothelial cells are adult, non-differentiated cells. In some embodiments, the smooth muscle cells are human smooth muscle cells. In further embodiments, the smooth muscle cells originated from a tissue selected from the group consisting of: blood, blood vessel, lymphatic vessel, tissue of the digestive tract, tissue of the genitourinary tract, adipose tissue, tissue of the respiratory tract, tissue of the reproductive system, bone marrow, and umbilical tissue. In some embodiments, the endothelial cells are human endothelial cells. In further embodiments, the endothelial cells originated from a tissue selected from the group consisting of: blood, blood vessel, lymphatic vessel, tissue of the digestive tract, tissue of the genitourinary tract, adipose tissue, tissue of the respiratory tract, tissue of the reproductive system, bone marrow, and umbilical tissue. In some embodiments, the fibroblasts are non-vascular fibroblasts. In some embodiments, the fibroblasts are derived from the vascular adventitia. In some embodiments, the cells are derived from a particular vertebrate subject. In further embodiments, one or more of the cell types are derived from a vertebrate subject that has a disease or condition that affects the cardiovascular system. In some embodiments, the cells are selected to mimic a particular disease state. In some embodiments, the cells are configured to mimic a particular disease state. In some embodiments, the cells are treated or modulated in a manner that mimics a particular disease state.

In certain embodiments, disclosed herein are arrays of living, three-dimensional, vascular wall segments, wherein each said vascular wall segment comprises smooth muscle cells, and optionally, one or more cell types selected from the group consisting of: fibroblasts and endothelial cells; wherein said cells are cohered to one another; wherein each said vascular wall segment is engineered. In some embodiments, at least one component of each vascular wall segment within the array was bioprinted. In further embodiments, each vascular wall segment within the array is free of any pre-formed scaffold at the time of use. In some embodiments, each vascular wall segment exists within a well of a biocompatible multi-well container. In further embodiments, the wells are coated with one of or more of the following: a biocompatible hydrogel, a protein, a chemical, a peptide, antibodies, or growth factors. In still further embodiments, the wells are coated with NovoGel™. In other embodiments, the wells are coated with agarose. In some embodiments, each vascular wall segment was placed onto a porous, biocompatible membrane within said wells of said container. In further embodiments, the container is compatible with automated drug screening. In some embodiments, each vascular wall segment is affixed to a biocompatible surface on one or more sides. In further embodiments, the biocompatible surface is a porous membrane. In still further embodiments, each vascular wall segment is subjected to shear force, caused by fluid flow, on one or more sides. In some embodiments, each vascular wall segment within the array is substantially similar. In other embodiments, one or more of the vascular wall segments within the array are unique. In some embodiments, the vascular wall segments within the array represent one or more distinct vascular tissues in the human body. In some embodiments, the vascular wall segments within the array are generated with one or more cell types derived from two or more distinct human donors. In some embodiments, each vascular wall segment within the array is maintained independently in culture. In other embodiments, two or more individual vascular wall segments within the array exchange soluble factors. In some embodiments, the array is for use in in vitro assays. In further embodiments, the array is for use in drug testing. In still further embodiments, the array is for use in cardiovascular drug testing.

In certain embodiments, disclosed herein are methods of constructing a living, three-dimensional vascular wall segment comprising the steps of: preparing cohered multicellular aggregates comprising smooth muscle cells; placing said cohered multicellular aggregates onto a support; and incubating said multicellular aggregates to allow them to cohere and form a vascular wall segment; wherein said incubation has a duration of about 2 hours to about 10 days. In some embodiments, at least one component of the vascular wall segment was bioprinted. In further embodiments, the vascular wall segment is used in in vitro assays and is free of any pre-formed scaffold at the time of use. In some embodiments, the cohered multicellular aggregates further comprise endothelial cells. In some embodiments, the cohered multicellular aggregates further comprise fibroblasts. In some embodiments, the cohered multicellular aggregates are substantially spherical or substantially cylindrical. In some embodiments, the cohered multicellular aggregates are placed onto a biocompatible surface. In further embodiments, the biocompatible surface consists of: a polymeric material, a porous membrane, plastic, glass, metal, or hydrogel. In some embodiments, the vascular wall segment is at least about 50 µm in its smallest dimension at the time of bioprinting. In further embodiments, the vascular wall segment is at least about 150 µm in its smallest dimension at the time of bioprinting. In still further embodiments, the vascular wall segment is at least about 266 µm in its smallest dimension at the time of bioprinting. In other embodiments, the vascular wall segment is at least about 500 µm in its smallest dimension at the time of bioprinting. In some embodiments, the method further comprises the step of subjecting said vascular wall segment to shear force, caused by fluid flow, on one or more sides.

In certain embodiments, disclosed herein are living, three-dimensional tissues comprising: smooth muscle cells, wherein said smooth muscle cells are cohered to one another; and one or more of: a layer of endothelial cells on one or more surfaces; a layer of fibroblasts on one or more surfaces; wherein at least one component of said tissue was bioprinted; and wherein said tissue is non-tubular. In some embodiments, the tissue is substantially free of any pre-formed scaffold. In some embodiments, the tissue is substantially free of any pre-formed scaffold at the time of bioprinting. In some embodiments, the tissue is substantially free of any pre-formed scaffold at the time of use. In some embodiments, the tissue is substantially planar. In some embodiments, the layer of endothelial cells comprises a monolayer, one or more sheets, or fused aggregates of endothelial cells. In some embodiments, the tissue comprises a layer of endothelial cells on one or more surfaces of said tissue. In some embodiments, the layer of fibroblasts comprises a monolayer, one or more sheets, or fused aggregates of fibroblasts. In some embodiments, the tissue comprises a layer of fibroblasts on one or more surfaces of said tissue. In some embodiments, the tissue comprises a layer of endothelial cells and a layer of fibroblasts; wherein said layer of endothelial cells is on one or more external surfaces of said tissue and said layer of fibroblasts is one or more distinct surfaces of said tissue. In some embodiments, the tissue is at least about 50 µm in its smallest dimension at the time of bioprinting. In further embodiments, the tissue is at least about 150 µm in its smallest dimension at the time of bioprinting. In still further embodiments, the tissue is at least about 250 µm in its smallest dimension at the time of bioprinting. In still further embodiments, the tissue is at least about 500 µm in its smallest dimension at the time of bioprinting. In some embodiments, the tissue is affixed to a biocompatible surface on one or more sides. In further embodiments, the biocompatible surface is a porous membrane. In further embodiments, the tissue is subjected to shear force, caused by fluid flow, on one or more sides. In some embodiments, the tissue is for use in in vitro assays. In further embodiments, the tissue is for use in drug testing. In still further embodiments, the tissue is for use in cardiovascular drug testing. In some embodiments, the smooth muscle cells, fibroblasts, and endothelial cells are adult, differentiated cells. In some embodiments, the smooth muscle cells, fibroblasts, and endothelial cells are adult, non-differentiated cells. In some embodiments, the smooth muscle cells are human smooth muscle cells. In further embodiments, the smooth muscle cells originated from a tissue selected from the group consisting of: blood, vascular tissue, blood vessel, lymphatic vessel, tissue of the digestive tract, tissue of the genitourinary tract, adipose tissue, tissue of the respiratory tract, tissue of the reproductive system, bone marrow, muscle tissue, connective tissue, mesoderm-derived tissue, and umbilical tissue. In some embodiments, the endothelial cells are human endothelial cells. In further embodiments, the endothelial cells originated from a tissue selected from the group consisting of: vascular tissue, blood, blood vessel, lymphatic vessel, tissue of the digestive tract, tissue of the genitourinary tract, adipose tissue, tissue of the respiratory tract, tissue of the reproductive system, mesoderm-derived tissue, bone marrow, and umbilical tissue. In some embodiments, the fibroblasts are non-vascular fibroblasts. In other embodiments, the fibroblasts are derived from the vascular adventitia. In some embodiments, the cells are derived from a particular vertebrate subject. In further embodiments, the cells are derived from a vertebrate subject that has a disease or condition that affects the cardiovascular system. In some embodiments, the cells are selected to mimic a particular disease state. In some embodiments, the cells are configured to mimic a particular disease state. In some embodiments, the cells are treated or modulated in a manner that mimics a particular disease state.

In certain embodiments, disclosed herein are arrays of living, three-dimensional, tissues, wherein each said tissue comprises mammalian cells, wherein said cells are cohered to one another; and one or more of: a layer of a first type of mammalian cells on one or more surfaces; a layer of a second type of mammalian cells on one or more surfaces; wherein at least one component of each said tissue was bioprinted; wherein each said tissue is maintained in culture. In some embodiments, each tissue within the array is free of any pre-formed scaffold at the time of use. In some embodiments, the mammalian cells include smooth muscle cells derived from a tissue selected from the group consisting of: vascular tissue, blood, blood vessel, lymphatic vessel, tissue of the digestive tract, tissue of the genitourinary tract, adipose tissue, tissue of the respiratory tract, tissue of the reproductive system, bone marrow, muscle tissue, mesenchymal tissue, connective tissue, mesoderm-derived tissue, and umbilical tissue. In some embodiments, the mammalian cells include endothelial cells derived from a tissue selected from the group consisting of: vascular tissue, blood, blood vessel, lymphatic vessel, tissue of the digestive tract, tissue of the genitourinary tract, adipose tissue, tissue of the respiratory tract, tissue of the reproductive system, mesoderm-derived tissue, bone marrow, and umbilical tissue. In some embodiments, the said mammalian cells include non-vascular fibroblasts. In other embodiments, the mammalian cells include vascular fibroblasts. In further embodiments, the vascular fibroblasts are derived from vascular adventitia. In some embodiments, each tissue within the array is substantially similar. In other embodiments, one or more of the tissues within the array is unique. In some embodiments, individual tissues within the array represent one or more specific tissues in the human body. In further embodiments, one or more individual tissues within the array represent human tissues selected from the group consisting of: blood or lymph vessel, muscle, uterus, nerve, mucous membrane, mesothelium, omentum, cornea, skin, liver, kidney, heart, trachea, lung, bone, bone marrow, adipose, connective, bladder, breast, pancreas, spleen, brain, esophagus, stomach, intestine, colon, rectum, ovary, and prostate. In some embodiments, each tissue exists in a well of a biocompatible multi-well container. In further embodiments, the wells are coated with one of or more of the following: a biocompatible hydrogel, a protein, a chemical, a peptide, antibodies, or growth factors. In some embodiments, the wells are coated with NovoGel™. In still further embodiments, the wells are coated with agarose. In some embodiments, each tissue was placed onto a porous, biocompatible membrane within the wells of the container. In some embodiments, the container is compatible with automated drug screening. In some embodiments, each tissue within the array is affixed to a biocompatible surface on one or more sides. In further embodiments, the biocompatible surface is a porous membrane. In still further embodiments, each tissue is subjected to shear force, caused by fluid flow, on one or more sides. In some embodiments, the tissues within the array are generated with one or more cell types derived from two or more distinct human donors. In some embodiments, each tissue within the array is maintained independently in culture. In other embodiments, two or more individual tissues within the array exchange soluble factors. In some embodiments, the array is for use in in vitro assays. In further embodiments, the array is for use in drug testing.

In certain embodiments, disclosed herein are methods of constructing a living, three-dimensional tissue comprising the steps of: preparing one or more cohered multicellular aggregates comprising mammalian cells; placing said one or more cohered multicellular aggregates onto a support; applying, to said one or more cohered multicellular aggregates, one or more of: a layer of a first type of mammalian cells on one or more external surfaces; a layer of a second type of mammalian cells on one or more external surfaces; and incubating said one or more multicellular aggregates to allow them to cohere and to form a tissue; wherein said incubation has a duration of about 2 hours to about 10 days. In some embodiments, at least one component of said tissue was bioprinted. In some embodiments, the tissue is free of any pre-formed scaffold at the time of manufacture. In further embodiments, the tissue is substantially free of any pre-formed scaffold at the time of manufacture. In other embodiments, the tissue is substantially free of any pre-formed scaffold at the time of use. In some embodiments, the tissue is at least about 50 µm in its smallest dimension at the time of bioprinting. In further embodiments, the tissue is at least about 150 µm in its smallest dimension at the time of bioprinting. In still further embodiments, the tissue is at least about 250 µm in its smallest dimension at the time of bioprinting. In other embodiments, the tissue is at least about 500 µm in its smallest dimension at the time of bioprinting. In further embodiments, the tissue has a length, width, or height, or thickness of about 50 µm to about 600 µm in the smallest dimension. In still further embodiments the tissue has a length, width, height, or thickness greater than 1 mm. In some embodiments, the cohered multicellular aggregates of the first cell type comprise stromal cells, connective tissue-derived cells, cells that are mesodermal in origin. In further embodiments, the cohered multicellular aggregates additionally comprise second cell types. In additional embodiments, the second cell type(s) are derived from epithelial tissues, endothelial tissues, mesenchymal tissues, or ectodermal tissues. In some embodiments, applying a layer of mammalian cells comprises coating at least one surface of the cohered multicellular aggregates with a suspension, a monolayer, one or more sheets, multiple layers, or fused aggregates of cells. In further embodiments, the suspension comprises about $1\times10^4$ to about $1\times10^6$ cells/W. In still further embodiments, the suspension comprises about $1\times10^5$ to about $1.5\times10^5$ cells/W. In some embodiments, applying a layer of mammalian cells comprises dispensing a suspension of cells directly onto one surface of said cohered multicellular aggregates as spatially-distributed droplets. In some embodiments, applying a layer of mammalian cells comprises dispensing a suspension of cells directly onto one surface of said cohered multicellular aggregates as a spray. In some embodiments, applying a layer of mammalian cells comprises placing one or more surfaces of said cohered multicellular aggregates in direct contact with an established layer of cells. In further embodiments, the established layer of cells comprises a monolayer, multiple layers, one or more sheets, or fused aggregates of cells. In some embodiments, a layer of a first type of cells is applied on one or more surfaces of said cohered multicellular aggregates and a layer of a second type of cells is applied to one or more distinct surfaces of said cohered multicellular aggregates. In some embodiments, the incubation has a duration of about 2 hours to about 10 days. In some embodiments, the step of applying one or more of: a layer of a first type of cells on one or more surfaces; a layer of a second type of cells on one or more surfaces is performed at the time the one or more cohered multicellular aggregates are placed. In other embodiments, the step of applying one or more of: a layer of a first type of cells on one or more external surfaces; a layer of a second type of cells on one or more external surfaces is performed during said incubation. In some embodiments, the methods further comprise the step of subjecting the tissue to shear force, caused by fluid flow, on one or more sides.

In certain embodiments, disclosed herein are living, three-dimensional vascular wall segments comprising: smooth muscle cells, wherein said smooth muscle cells are cohered to one another; and one or more of: a layer of endothelial cells on one or more surfaces; a layer of fibroblasts on one or more surfaces; wherein at least one component of said vascular wall segment was bioprinted; and wherein said vascular wall segment is non-tubular. In some embodiments, the vascular wall segment is substantially free of any pre-formed scaffold at the time of manufacture. In other embodiments, the vascular wall segment is substantially free of any pre-formed scaffold at the time of use. In some embodiments, the vascular wall segment is substantially planar. In some embodiments, the layer of endothelial cells comprises a monolayer, one or more layers, one or more sheets, or fused aggregates of endothelial cells. In some embodiments, the vascular wall segment comprises a layer of endothelial cells on one or more surfaces. In some embodiments, the layer of fibroblasts comprises a monolayer, one or more layers, one or more sheets, or fused aggregates of fibroblasts. In some embodiments, the vascular wall segment comprises a layer of fibroblasts on one or more surfaces of said vascular wall segment. In some embodiments, the vascular wall segment comprises a layer of endothelial cells and said layer of fibroblasts; wherein said layer of endothelial cells is on one or more external surfaces of said vascular wall segment and said layer of fibroblasts is one or more distinct surfaces of said vascular wall segment. In some embodiments, the vascular wall segment is at least about 50 μm in its smallest dimension at the time of bioprinting. In further embodiments, the vascular wall segment is at least about 150 μm in its smallest dimension at the time of bioprinting. In still further embodiments, the vascular wall segment is at least about 250 μm in its smallest dimension at the time of bioprinting. In still further embodiments, the vascular wall segment is at least about 500 μm in its smallest dimension at the time of bioprinting. In some embodiments, the vascular wall segment is affixed to a biocompatible surface on one or more sides. In further embodiments, the biocompatible surface is a porous membrane. In still further embodiments, the vascular wall segment is subjected to shear force, caused by fluid flow, on one or more sides. In some embodiments, the vascular wall segment is for use in in vitro assays. In further embodiments, the vascular wall segment is for use in drug testing. In still further embodiments, the vascular wall segment is for use in cardiovascular drug testing. In some embodiments, the smooth muscle cells, fibroblasts, and endothelial cells are adult, differentiated cells. In other embodiments, the smooth muscle cells, fibroblasts, and endothelial cells are adult, non-differentiated cells. In some embodiments, the smooth muscle cells are human smooth muscle cells. In further embodiments, the smooth muscle cells originated from a tissue selected from the group consisting of: vascular tissue, blood, blood vessel, lymphatic vessel, tissue of the digestive tract, tissue of the genitourinary tract, adipose tissue, tissue of the respiratory tract, tissue of the reproductive system, bone marrow, muscle tissue, connective tissue, and umbilical tissue. In some embodiments, the endothelial cells are human endothelial cells. In further embodiments, the endothelial cells originated from a tissue selected from the group consisting of: vascular tissue, blood, blood vessel, lymphatic vessel, tissue of the digestive tract, tissue of the genitourinary tract, adipose tissue, tissue of the respiratory tract, tissue of the reproductive system, bone marrow, and umbilical tissue. In some embodiments, the fibroblasts are non-vascular fibroblasts. In other embodiments, the fibroblasts are vascular fibroblasts. In further embodiments, the fibroblasts are derived from the vascular adventitia. In some embodiments, one or more of the cellular components are derived from a particular vertebrate subject. In further embodiments, one or more of the cellular components are derived from a vertebrate subject that has a disease or condition that affects the cardiovascular system. In some embodiments, one or more of the cellular components are selected and/or configured to mimic a particular disease state. In some embodiments, one or more of the cellular components are treated and/or modulated in a manner that mimics a particular disease state.

In certain embodiments, disclosed herein are arrays of living, three-dimensional vascular wall segments, wherein each said vascular wall segment comprises smooth muscle cells, wherein said smooth muscle cells are cohered to one another; and one or more of: a layer of endothelial cells on one or more surfaces; a layer of fibroblasts on one or more surfaces; wherein each said vascular wall segment is engineered; wherein each said vascular wall segment is maintained in culture. In some embodiments, at least one component of each vascular wall segment within the array was bioprinted. In further embodiments, each vascular wall segment within the array is substantially free of any pre-formed scaffold at the time of manufacture. In other embodiments, each vascular wall segment within the array is substantially free of any pre-formed scaffold at the time of use. In some embodiments, each vascular wall segment exists within a well of a biocompatible multi-well container. In further embodiments, the wells are coated with one of or more of the following: a biocompatible hydrogel, a protein, a chemical, a peptide, antibodies, or growth factors. In some embodiments, the wells are coated with NovoGel™. In other embodiments, the wells are coated with agarose. In some embodiments, each vascular wall segment was placed onto a porous, biocompatible membrane within said wells of said container. In some embodiments, the container is compatible with automated drug screening. In some embodiments, each vascular wall segment within the array is affixed to a biocompatible surface on one or more sides. In further embodiments, the biocompatible surface is a porous membrane. In still further embodiments, each vascular wall segment is subjected to shear force, caused by fluid flow, on one or more sides. In some embodiments, each vascular wall segment within the array is substantially similar. In other embodiments, one or more of the vascular wall segments within the array are unique. In some embodiments, the vascular wall segments within the array represent one or more distinct vascular tissues in the human body. In some embodiments, the vascular wall segments within the array are generated with one or more cell types derived from two or more distinct human donors. In some embodiments, each vascular wall segment within the array is maintained independently in culture. In other embodiments, two or more individual vascular wall segments within the array exchange soluble factors. In some embodiments, the array is for use in in vitro assays. In further embodiments, the array is for use in drug testing. In still further embodiments, the array is for use in cardiovascular drug testing.

In certain embodiments, disclosed herein are methods of constructing a living, three-dimensional vascular wall segment comprising the steps of: culturing a layer of fibroblasts on a biocompatible support; preparing a one or more cohered multicellular aggregates comprising smooth muscle cells, wherein said aggregates are substantially spherical or substantially cylindrical; placing one or more cohered multicellular aggregates onto said support; applying, to said one or more cohered multicellular aggregates, a layer of endothelial cells on one or more surfaces; and incubating said multicellular aggregates to allow them to cohere to form a tissue.

In certain embodiments, disclosed herein are engineered tissue culture systems comprising a three-dimensional cell-based element and a temporary or removable confinement, wherein the confinement material allows for direct contact between the cells and a nutrient medium. In some embodiments, the engineered, three-dimensional cell-based element was bioprinted. In further embodiments, the engineered, three-dimensional cell-based element is free of any pre-formed scaffold. In some embodiments, the confinement material has at least one of the following features: does not substantially adhere to the cells; is biocompatible; is extrudable; is non-cellular; is of sufficient strength to provide support for the cells; and is not soluble in aqueous conditions. In further embodiments, the confinement material is not plastic, is not glass, and is not ceramic. In some embodiments, the confinement material is a hydrogel. In further embodiments, the confinement material is Novo-Gel™. In further embodiments, the confinement material comprises one or more of: agarose, polyethylene glycol diacrylate (PEG-DA), hyaluronan, gelatin, poloxamer, hydroxyethyl methacrylate, peptide hydrogel, Matrigel™, polydimethylsiloxane, silicon, silk, polyacrylamide, poly lactic acid, a surfactant polyol, and alginate. In some embodiments, at least one of: the cells and/or the confinement material were extruded from a bioprinter. In further embodiments, there are gaps in the confinement material and wherein the nutrient medium is capable of contacting the cells through the gaps. In still further embodiments, the gaps were between about 100 µm and about 30 mm wide. In some embodiments, the gaps were distributed non-uniformly around the structure, whereby the cells of the tissue were exposed to nutrients non-uniformly. In some embodiments, wherein at least about 10% of the surface area of the tissue was exposed to gaps suitable for contact with a nutrient medium. In some embodiments, the confinement material was overlaid on the cells as at least one elongated element. In further embodiments, the elongated element of confinement material had a cross-sectional thickness between about 100 µm and about 1 mm. In some embodiments, there were gaps between the elongated elements of confinement material. In some embodiments, gaps were left between elongated elements when extruding the confinement material from a bioprinter. In other embodiments, at least some of the confinement material was removed from the system to provide gaps. In some embodiments, the elongated elements of confinement material were substantially parallel and the gaps were elongated. In some embodiments, the elongated elements of confinement material were arranged in a lattice. In some embodiments, the elongated elements of confinement material affix the structure to the supporting surface. In some embodiments, the system was suitable for shipping. In some embodiments, the bioprinted cells comprise at least one of: smooth muscle cells, endothelial cells, fibroblasts, and epithelial cells. In some embodiments, the nutrient medium comprised at least one of: oxygen ($O_2$), a carbon source, a nitrogen source, growth factors, salts, minerals, vitamins, serum, antibiotics, chemicals, proteins, nucleic acids, pharmaceutical compounds, and antibodies.

In certain embodiments, disclosed herein are engineered, living tissues comprising a three-dimensional cell-comprising element, held in place by a hydrogel, wherein the hydrogel was dispensed on said cell-comprising element as cylinders or ribbons with gaps between the cylinders or ribbons through which the cells access nutrients, and wherein the hydrogel is removable from the tissue.

In certain embodiments, disclosed herein are methods for increasing the viability of an engineered tissue comprising providing direct contact between the tissue and a nutrient medium through a temporary or semi-permanent lattice, wherein the tissue is free of any pre-formed scaffold. In some embodiments, the step of providing direct contact between the tissue and a nutrient medium through a temporary or semi-permanent lattice comprises constraining said tissue in a porous or gapped material. In further embodiments, the pores or gaps were between about 100 µm and about 30 mm wide. In further embodiments, the porous or gapped material was a hydrogel. In still further embodiments, the porous or gapped material was agarose. In some embodiments, viability of an engineered tissue is increased ex vivo. In some embodiments, viability of at least a portion of the cells comprising an engineered tissue is extended. In further embodiments, viability of the cells is extended by 1 day or more. In some embodiments, the at least one nutrient is selected from the group consisting of: a carbon source, a nitrogen source, growth factors, salts, minerals, vitamins, serum, antibiotics, proteins, nucleic acids, pharmaceutical compounds, ad antibodies. In some embodiments, at least one nutrient is oxygen ($O_2$). In further embodiments, the porous or gapped hydrogel confinement is designed to provide the bioprinted cells with differential exposure to nutrients on one or more surfaces.

In certain embodiments, disclosed herein are methods of making tissue culture systems comprising the steps of: establishing a three-dimensional cell-comprising element on a biocompatible substrate; and dispensing confinement material overlaying the three-dimensional cell-comprising element, wherein the overlaid confinement material allows at least some of the cells to contact a growth medium.

In certain embodiments, disclosed herein are methods of making tissue culture systems comprising the steps of: dispensing a perimeter of confinement material on a surface; dispensing cells within the perimeter; and dispensing confinement material overlaying the cells, wherein the overlaid confinement material allows at least some of the cells to contact a growth medium. In some embodiments, dispensing confinement material is accomplished by bioprinting. In some embodiments, the method comprises or further comprises culturing the system in a suitable medium to mature the bioprinted cellular construct.

EXAMPLES

The following specific examples are to be construed as merely illustrative, and not limitative of the remainder of the disclosure in any way whatsoever.

Example 1—Cell Culture

Smooth Muscle Cells

Primary human aortic smooth muscle cells (HASMC; GIBCO/Invitrogen Corp., Carlsbad, CA) were maintained and expanded in low glucose dulbecco's modified eagle medium (DMEM; Invitrogen Corp., Carlsbad, CA) supplemented with 10% fetal bovine serum (FBS), 100 U/mL Penicillin, 0.1 mg/mL streptomycin, 0.25 µg/mL of amphotericin B, 0.01M of HEPES (all from Invitrogen Corp., Carlsbad, CA), 50 mg/L of proline, 50 mg/L of glycine, 20 mg/L of alanine, 50 mg/L of ascorbic acid, and 3 µg/L of $CuSO_4$ (all from Sigma, St. Louis, MO) at 37° C. and 5% $CO_2$. Confluent cultures of HASMC between passage 4 and 8 were used in all studies.

Endothelial Cells

Primary human aortic endothelial cells (HAEC; GIBCO/Invitrogen Corp., Carlsbad, CA) were maintained and expanded in Medium 199 (Invitrogen Corp., Carlsbad, CA) supplemented with 10% FBS, 1 µg/mL of hydrocortisone, 10 ng/mL of human epidermal growth factor, 3 ng/mL of basic fibroblast growth factor, 10 µg/mL of heparin, 100 U/mL Penicillin, 0.1 mg/mL streptomycin, and 0.25 µg/mL of amphotericin B (all from Invitrogen Corp., Carlsbad, CA). The cells were grown on gelatin (from porcine serum; Sigma, St. Louis, MO) coated tissue culture treated flasks at 37° C. and 5% $CO_2$. Confluent cultures of HAEC between passage 4 and 8 were used in all studies.

Fibroblasts

Primary human dermal fibroblasts (HDF; GIBCO/Invitrogen Corp., Carlsbad, CA) were maintained and expanded in Medium 106 (Invitrogen Corp., Carlsbad, CA) supplemented with 2% FBS, 1 µg/mL of hydrocortisone, 10 ng/mL of human epidermal growth factor, 3 ng/mL of basic fibroblast growth factor, 10 µg/mL of heparin, 100 U/mL Penicillin, and 0.1 mg/mL streptomycin (all from Invitrogen Corp., Carlsbad, CA) at 37° C. and 5% $CO_2$. Confluent cultures of HDF between passage 4 and 8 were used in all studies.

SMC-Like Cells from the SVF of Human Lipoaspirate

SMC-like cells were generated from the adherent fraction of cells isolated after collagenase digestion of lipoaspirates. This digestion produces a population of cells known as the stromal vascular fraction (SVF). The cells of the SVF are plated on standard tissue culture plastic and adherent cells further selected with appropriate culture conditions. SMC-like cells from the SVF of adipose tissue lipoaspirates were maintained and expanded in high glucose dulbecco's modified eagle medium (DMEM; Invitrogen Corp., Carlsbad, CA) supplemented with 10% fetal bovine serum (FBS), 100 U/mL Penicillin, 0.1 mg/mL streptomycin, 0.25 µg/mL of amphotericin B, 0.01M of HEPES (all from Invitrogen Corp., Carlsbad, CA), 50 mg/L of proline, 50 mg/L of glycine, 20 mg/L of alanine, 50 mg/L of ascorbic acid, and 3 µg/L of $CuSO_4$ (all from Sigma, St. Louis, MO) at 37° C. and 5% $CO_2$. Confluent subcultures of SVF-SMC between passage 3 and 8 were used in all studies.

EC from the SVF of Human Lipoaspirate

Endothelial cells from the stromal vascular fraction (SVF) were maintained and expanded in growth media that is commonly used to grow primary isolates of bona fide endothelial cells (EC). Specifically, SVF-EC were maintained in M199 supplemented with 10% FBS, 1 µg/mL of hydrocortisone, 10 ng/mL of human epidermal growth factor, 3 ng/mL basic fibroblast growth factor, 10 µg/mL of heparin, 100 U/mL Penicillin, and 0.1 mg/mL streptomycin. The cells were grown on tissue culture-treated flasks at 37° C. and 5% $CO_2$. Confluent cultures of SVF-EC between passage 3 and 8 were used in all studies.

Lung-Derived Cells

Normal Human Lung Fibroblasts were procured from LifeLine technologies or Lonza and propagated according to manufacturer's instructions using media from respective vendors. Small Airway Epithelial Cells were purchased from Lonza and grown in vendor-provided culture media according to manufacturer's instructions. Pulmonary airway and pulmonary vascular smooth muscle cells were obtained from LifeLine Technologies and cultured according to manufacturer's instructions in vendor-provided media.

Example 2—NovoGel™ Solutions and Mold

Preparation of 2% and 4% (w/v) NovoGel™ Solution 1 g or 2 g (for 2% or 4% respectively) of NovoGel™ (Organovo, San Diego, CA) was dissolved in 50 mL of Dulbecco's phosphate buffered saline (DPBS; Invitrogen Corp., Carlsbad, CA). Briefly, the DPBS and NovoGel™ are heated to 85° C. on a hot plate with constant stirring until the NovoGel™ dissolves completely. NovoGel™ solution is sterilized by steam sterilization at 125° C. for 25 minutes. The NovoGel™ solution remains in liquid phase as long as the temperature is maintained above 65.5° C. Below this temperature a phase transition occurs, the viscosity of the NovoGel™ solution increases and the NovoGel™ forms a solid gel.

Preparation of NovoGel™ Mold

An NovoGel™ mold was fabricated for the incubation of cylindrical bio-ink using a Teflon® mold that fit a 10 cm Petri dish. Briefly, the Teflon® mold was pre-sterilized using 70% ethanol solution and subjecting the mold to UV light for 45 minutes. The sterilized mold was placed on top of the 10 cm Petri dish (VWR International LLC, West Chester, PA) and securely attached. This assembly (Teflon® mold+ Petri dish) was maintained vertically and 45 mL of pre-warmed, sterile 2% NovoGel™ solution was poured in the space between the Teflon® mold and the Petri dish. The assembly was then placed horizontally at room temperature for 1 hour to allow complete gelation of the NovoGel™. After gelation, the Teflon® print was removed and the NovoGel™ mold was washed twice using DPBS. Then 17.5 mL of HASMC culture medium was added to the NovoGel™ mold for incubating the polytypic cylindrical bio-ink.

Example 3—Fabrication of HASMC-HAEC Polytypic Cylindrical Bio-Ink

To prepare polytypic cylindrical bio-ink, HASMC and HAEC were individually collected and then mixed at predetermined ratios. Briefly, the culture medium was removed from confluent culture flasks and the cells were washed with DPBS (1 ml/5 $cm^2$ of growth area). Cells were detached from the surface of the culture flasks by incubation in the presence of trypsin (1 ml/15 $cm^2$ of growth area; Invitrogen Corp., Carlsbad, CA) for 10 minutes. HASMC were detached using 0.15% trypsin while HAEC were detached using 0.1% trypsin. Following the incubation appropriate culture medium was added to the flasks (2× volume with respect to trypsin volume). The cell suspension was centrifuged at 200 g for 6 minutes followed by complete removal of supernatant solution. Cell pellets were resuspended in respective culture medium and counted using a hemocytometer. Appropriate volumes of HASMC and HAEC were combined to yield a polytypic cell suspension containing 15% HAEC and remainder 85% HASMC (as a % of total cell population). The polytypic cell suspension was centrifuged at 200 g for 5 minutes followed by complete removal of supernatant solution. Polytypic cell pellets were resuspended in 6 mL of HASMC culture medium and transferred to 20 mL glass vials (VWR International LLC, West Chester, PA), followed by incubation on an orbital shaker at 150 rpm for 60 minutes, and at 37° C. and 5% $CO_2$. This allows the cells to aggregate with one another and initiate cell-cell adhesions. Post-incubation, the cell suspension was transferred to a 15 mL centrifuge tube and centrifuged at 200 g for 5 minutes. After removal of the supernatant medium, the cell pellet was resuspended in 400 µl of HASMC culture medium and pipetted up and down several times to ensure all cell clusters were broken. The cell suspension was transferred into a 0.5 mL microfuge tube (VWR International LLC, West Chester, PA) placed inside a 15 mL centrifuge tube followed by centrifugation at 2000 g for 4 minutes to form a highly dense and compact cell pellet. The supernatant medium was aspirated and the cells were transferred into capillary tubes (OD 1.5 mm, ID 0.5 mm, L 75 mm; Drummond Scientific Co., Broomall, PA) by aspiration so as to yield cylindrical bio-ink 50 mm in length. The cell paste inside the capillaries was incubated in HASMC medium for 20 minutes at 37° C. and 5% $CO_2$. The cylindrical bio-ink was then extruded from the capillary tubes into the grooves of a NovoGel™ mold (See, e.g., Example 2) (covered with HASMC medium) using the plunger supplied with the capillaries. The cylindrical bio-ink was incubated for 24 hours at 37° C. and 5% $CO_2$.

Example 4—Bioprinting Blood Vessel Wall Segments Comprising HASMC and HAEC Polytypic Cylindrical Bio-Ink Blood vessel wall-mimicking segments were bioprinted utilizing a NovoGen MMX Bioprinter™ (Organovo, Inc., San Diego, CA) either on NovoGel™ base plates (100 mm Petri dish size), inside NovoGel™ coated wells, or directly onto Corning® Transwell® inserts in a multi-well plate (e.g., 6-well plates). This process involves the following three phases:

Preparation of HASMC-HAEC Polytypic Bio-Ink

Cultures of human aortic smooth muscle cells (HASMC) and human aortic endothelial cells (HAEC) were trypsinized, counted, and mixed in appropriate quantities to yield bio-ink that comprised HASMC:HAEC at either a 85:15 or 70:30 ratio. The polytypic cell suspension was shaken for 60 minutes on a rotary shaker, collected, and centrifuged. Cells were drawn into 266 or 500 µm (ID) glass microcapillaries, then extruded into media covered NovoGel™ plates and incubated for a minimum of 6 hours.

Bioprinting of Patches/Three-Dimensional Cell Sheets

In the case of printing onto NovoGel™ beds inside the wells of a multi-well plate or on NovoGel™ base plates (100 mm Petri dish size), a first layer of NovoGel™ cylinders was bioprinted. Then, on top of it a box was bioprinted using NovoGel™ rods such that the space inside was 8 mm long×1.25 mm wide. Matured cylindrical bio-ink was loaded onto the bioprinter for printing inside the box. Finally, a third layer of NovoGel™ cylinders was printed on top of the second that either covers the entire length of cells or creates a lattice/mesh type structure on top. In the case of printing onto Transwell® inserts inside the wells of the plate, the first layer of NovoGel™ rods described earlier was eliminated. The bioprinted constructs were then covered with appropriate cell culture medium and incubated during which the adjoining segments of the bio-ink fused to form a three-dimensional patch of cells.

Maturation of Bioprinted Constructs

The bioprinted constructs comprising the HASMC-HAEC bio-ink were incubated for a period of 1-7 days to allow the construct to mature and provide the HAEC sufficient time to sort to the periphery of the construct thereby mimicking a section of a blood vessel wall. In some experiments, the three-dimensional cellular patch was subjected to shear forces (i.e., pulsatile flow) to aid the process of HAEC sorting.

Example 5—Fabrication of HASMC-HDF-HAEC Polytypic Cylindrical Bio-Ink

To prepare polytypic cylindrical bio-ink, HASMC, HDF, and HAEC were individually collected and then mixed at pre-determined ratios (e.g., HASMC:HDF:HAEC ratios of 70:25:5). Briefly, the culture medium was removed from confluent culture flasks and the cells were washed with DPBS (1 ml/10 cm2 of growth area). Cells were detached from the surface of the culture flasks by incubation in the presence of trypsin (1 ml/15 cm2 of growth area; Invitrogen Corp., Carlsbad, CA) for 10 minutes. HASMC and HDF were detached using 0.15% trypsin while HAEC were detached using 0.1% trypsin. Following the incubation appropriate culture medium was added to the flasks (2× volume with respect to trypsin volume). The cell suspension was centrifuged at 200 g for 6 minutes followed by complete removal of supernatant solution. Cell pellets were resuspended in respective culture medium and counted using a hemocytometer. Appropriate volumes of HASMC, HDF, and HAEC were combined to yield polytypic cell suspensions. The polytypic cell suspensions were centrifuged at 200 g for 5 minutes followed by aspiration of the supernatant solution. Polytypic cell pellets were resuspended in 6 mL of HASMC culture medium and transferred to 20 mL glass vials (VWR International LLC, West Chester, PA), followed by incubation on an orbital shaker at 150 rpm for 60 minutes, and at 37° C. and 5% $CO_2$. This allows the cells to aggregate with one another and initiate cell-cell adhesions. Post-incubation, the cell suspension was transferred to a 15 mL centrifuge tube and centrifuged at 200 g for 5 minutes. After removal of the supernatant medium, the cell pellet was resuspended in 400 µL of HASMC culture medium and pipetted up and down several times to ensure all cell clusters were broken. The cell suspension was transferred into a 0.5 mL microfuge tube (VWR International LLC, West Chester, PA) placed inside a 15 mL centrifuge tube followed by centrifugation at 2000 g for 4 minutes to form a highly dense and compact cell pellet. The supernatant medium was aspirated and the cells were transferred into capillary tubes (OD 1.25 mm, ID 0.266 mm, L 75 mm; Drummond Scientific Co., Broomall, PA) by aspiration so as to yield cylindrical bio-ink aggregates 50 mm in length. The cell paste inside the capillaries was incubated in HASMC medium for 20 minutes at 37° C. and 5% $CO_2$. The cylindrical bio-ink was then extruded from the capillary tubes into the grooves of a NovoGel™ mold (see, e.g., Example 2) (covered with HASMC medium) using the plunger supplied with the capillaries. The cylindrical bio-ink was incubated for 6 to 24 hours at 37° C. and 5% $CO_2$.

Example 6—Bioprinting Blood Vessel Wall Segments Comprising Polytypic HASMC, HAEC, and HDFa Bio-Ink Blood vessel wall-mimicking segments were bioprinted utilizing a NovoGen MMX Bioprinter™ (Organovo, Inc., San Diego, CA) either on NovoGel™ base plates (100 mm Petri dish size), inside NovoGel™ coated wells, or directly onto Corning® Transwell® inserts in a multi-well plate (e.g., 6-well plates). This process involves the following three phases:

Preparation of Polytypic HASMC-HDFa-HAEC Bio-Ink

Cultures of HASMC, HAEC, and HDFa were trypsinized, counted, and mixed in appropriate quantities to yield bio-ink that comprised HASMC:HDFa:HAEC at a 70:15:15 ratio. The polytypic cell suspension was shaken for 60 minutes on a rotary shaker, collected, and centrifuged. Cells were drawn into 266 or 500 µm (ID) glass microcapillaries, then extruded into media covered NovoGel™ plates and incubated for a minimum of 6 hours.

Bioprinting of Patches/Three-Dimensional Cell Sheets

In the case of printing onto NovoGel™ beds inside the wells of a multi-well plate or on NovoGel™ base plates (100 mm Petri dish size), a first layer of NovoGel™ cylinders was bioprinted. Then, on top of it a box was bioprinted using NovoGel™ rods such that the space inside was 8 mm long×1.25 mm wide. Matured cylindrical bio-ink aggregates were loaded onto the bioprinter for printing inside the box. Finally, a third layer of NovoGel™ cylinders was printed on top of the second that either covers the entire length of cells or creates a lattice/mesh type structure on top. In the case of printing onto Transwell® inserts inside the wells of the plate, the first layer of NovoGel™ rods described earlier was eliminated. The bioprinted constructs were then covered with appropriate cell culture medium and incubated during which the adjoining segments of the bio-ink fused to form a three-dimensional patch of cells.

Maturation of Bioprinted Constructs

The bioprinted constructs comprising polytypic HASMC-HDFa-HAEC bio-ink were incubated for a period of 1-7 days to allow the construct to mature and provide the HAEC sufficient time to sort to the periphery of the construct thereby mimicking a section of a blood vessel wall. In some experiments, the three-dimensional cellular patch was subjected to shear forces (i.e., pulsatile flow) to aid the process of HAEC sorting.

Example 7—Fabrication of SVF-SMC-SVF-EC Polytypic Cylindrical Bio-Ink

To prepare polytypic cylindrical bio-ink, SVF-SMC and SVF-EC were individually collected and then mixed at pre-determined ratios. Briefly, the culture medium was removed from confluent culture flasks and the cells were washed with DPBS (1 ml/5 cm$^2$ of growth area). Cells were detached from the surface of the culture flasks by incubation in the presence of TrypLE (Invitrogen Corp., Carlsbad, CA) for 5 to 10 minutes. Following the incubation appropriate culture medium was added to the flasks to quench enzyme activity. The cell suspension was centrifuged at 200 g for 6 minutes followed by complete removal of supernatant solution. Cell pellets were resuspended in respective culture medium and counted using a hemocytometer. Appropriate volumes of SVF-SMC and SVF-EC were combined to yield a polytypic cell suspension containing 15% SVF-EC and remainder 85% SVF-SMC (as a % of total cell population). The polytypic cell suspension was centrifuged at 200 g for 5 minutes followed by complete removal of supernatant solution. Polytypic cell pellets were resuspended in 6 mL of SVF-SMC culture medium and transferred to 20 mL glass vials (VWR International LLC, West Chester, PA), followed by incubation on an orbital shaker at 150 rpm for 60 minutes, and at 37° C. and 5% $CO_2$. This allows the cells to aggregate with one another and initiate cell-cell adhesions. Post-incubation, the cell suspension was transferred to a 15 mL centrifuge tube and centrifuged at 200 g for 5 minutes. After removal of the supernatant medium, the cell pellet was resuspended in 400 µl of SVF-SMC culture medium and pipetted up and down several times to ensure all cell clusters were broken. The cell suspension was transferred into a 0.5 mL microfuge tube (VWR International LLC, West Chester, PA) placed inside a 15 mL centrifuge tube followed by centrifugation at 2000 g for 4 minutes to form a highly dense and compact cell pellet. The supernatant medium was aspirated and the cells were transferred into capillary tubes (OD 1.25 mm, ID 0.266 mm, L 75 mm; Drummond Scientific Co., Broomall, PA) by aspiration so as to yield cylindrical bio-ink aggregates 50 mm in length. The cell paste inside the capillaries was incubated in SVF-SMC medium for 20 minutes at 37° C. and 5% $CO_2$. The cylindrical bio-ink was then extruded from the capillary tubes into the grooves of a NovoGel™ mold (see, e.g., Example 2) (covered with SVF-SMC medium) using the plunger supplied with the capillaries. The cylindrical bio-ink was incubated for 6 to 12 hours at 37° C. and 5% $CO_2$.

Example 8—Bioprinting Blood Vessel Wall Segments Comprising a Mixture of Vascular SMC and EC Blood vessel wall constructs were bioprinted utilizing a NovoGen MMX Bioprinter™ (Organovo, Inc., San Diego, CA) into the wells of 6-well culture plates that had been previously covered with 1.5 mL of 2% (w/v) NovoGel™. Cylindrical bio-ink was prepared with a mixture of human vascular smooth muscle cells (SMC) and human endothelial cells (EC) at an SMC:EC ratio of 85:15 or 70:30. Bio-ink was generated by aspiration of a cell pellet (SMC:EC) into a glass microcapillary tube with either a 500 µm or 266 µm inner diameter (ID). The bio-ink cylinders were then extruded into a NovoGel™ mold covered with appropriate culture medium. Prior to bioprinting, the bio-ink was held for 6 to 18 hours. Polytypic bio-ink containing a mixture of SMC and EC was used. In these experiments the EC within the bio-ink sorted to the periphery of the bio-ink aggregates, resulting in a construct that is covered with EC and contains a SMC-rich construct wall. This process resulted in the development of a vascular wall construct that contains a wall comprised of SMC and a covering of EC (e.g., a putative tunica media and tunica intima). The constructs were bioprinted in the center of the culture well using bioprinting protocols and the culture well was filled with appropriate culture media and the constructs returned to the incubator for maturation and evaluation. Following bioprinting, the construct was covered with an appropriate amount of culture media (e.g., 4 mL for 1 well of a 6-well plate). In summary, this example describes the use of vascular SMC and EC for bioprinting a vascular wall segment or mimic within a standard size multi-well tissue culture plate. The resulting vessel wall segment or mimic is characterized by an external layer or layers of EC and internal wall comprised largely or solely of SMC.

Example 9—Bioprinting Blood Vessel Wall Segments Comprising Human Vascular SMC with a Covering of EC Blood vessel wall constructs were bioprinted utilizing a NovoGen MMX Bioprinter™ (Organovo, Inc., San Diego, CA) into the wells of 6-well culture plates that had been previously covered with 1.5 mL of 2% (w/v) NovoGel™. Cellular bio-ink was prepared with human vascular smooth muscle cells (SMC). Bio-ink cylinders were generated by aspiration of a cell pellet (SMC) into a glass microcapillary tube with either a 500 µm or 266 µm inner diameter (ID). The cylindrical bio-ink aggregates were then extruded into a NovoGel™ mold covered with appropriate culture medium. Prior to bioprinting, the bio-ink was held for 6 to 18 hours. An EC-concentrate ($1\text{-}1.5 \times 10^5$ cells/µl) was bioprinted directly on top of the previously bioprinted SMC structure to form a second layer of the construct. This process resulted in the development of a vascular wall construct that contains a wall comprised of SMC and a covering of EC (e.g., a putative tunica media and tunica intima). The constructs were bioprinted in the center of the culture well using bioprinting protocols. Following bioprinting, the construct was covered with an appropriate amount of culture media (e.g., 4 mL for 1 well of a 6-well plate) and returned to the incubator for maturation and evaluation. In summary, this example describes the use of vascular SMC and EC for bioprinting a vascular wall segment or mimic within a standard size multi-well tissue culture plate. The resulting vessel wall segment or mimic is characterized by an external layer of EC and internal wall comprised largely or solely of SMC.

Example 10—Bioprinting Blood Vessel Wall Segments Comprising HASMC Layered with HAEC Utilizing NovoGel™ Containment Blood vessel wall-mimicking segments were bioprinted utilizing a NovoGen MMX Bioprinter™ (Organovo, Inc., San Diego, CA) either inside NovoGel™ coated wells or directly onto Corning® Transwell® inserts in a multi-well plate (e.g., 6-well plates). This process involved the following three phases:

Preparation of HASMC Bio-Ink

Cultures of human aortic smooth muscle cells (HASMC) were trypsinized, and then shaken for 60 minutes on a rotary shaker. Post-shaking, cells were collected, centrifuged, and aspirated into 266 or 500 µm (ID) glass microcapillaries. Finally, the cells were extruded into media covered NovoGel™ plates and incubated for a minimum of 6 hours.

Bioprinting of HASMC Patches Layered with HAEC

Just prior to bioprinting of patches (e.g., segments), human aortic endothelial cell (HAEC) cultures were trypsinized, counted, and then resuspended in HAEC medium at a working concentration of $1 \times 10^6$ cells/10 µL of medium. The HAEC suspension was placed in the bioprinter to be utilized for layering bioprinted patches. In the case of printing onto NovoGel™ beds inside the wells of a multi-well plate, a first layer of NovoGel™ cylinders was bioprinted. Then, on top of it a box was bioprinted using NovoGel™ rods such that the space inside was 8 mm long×1.25 mm wide. Matured cylindrical HASMC bio-ink was loaded onto the bioprinter for printing inside the box. HAEC in suspension were then drawn into a clean microcapillary by the bioprinter and dispensed on top of the printed HASMC layer 4 times near the 4 corners of the printed patch. Each drop was 2.5 µL in volume. The construct was incubated for a period of 15-30 minutes before proceeding to print the third layer. Finally, a third layer of NovoGel™ cylinders was printed on top of the second to create a lattice/mesh type structure on top. In the case of printing onto Transwell® inserts inside the wells of the plate, the first layer of NovoGel™ rods described earlier was eliminated. The bioprinted constructs were then covered with appropriate cell culture medium and incubated.

Maturation of Bioprinted Constructs

The bioprinted constructs were incubated for a period of 1-7 days to allow the construct to mature and provide the HAEC sufficient time to form a uniformly thin monolayer on top of the HASMC patch. In some experiments, the three-dimensional cellular patch was subjected to shear forces (i.e., pulsatile flow).

Example 11—Bioprinting Blood Vessel Wall Segments Comprising HASMC Layered with HAEC onto a HDFa Monolayer Utilizing NovoGel™ Containment Blood vessel wall-mimicking segments were bioprinted utilizing a NovoGen MMX Bioprinter™ (Organovo, Inc., San Diego, CA) directly onto Corning® Transwell® inserts in a multi-well plate (e.g., 6-well plates). This process involved the following four phases:

Culture of HDFa's onto Transwell Membranes

Human adult dermal fibroblasts (HDFa) were seeded onto Transwell membranes at a density of 20,000 cells/cm' and cultured for a minimum of 6 days. This allowed the cells to adhere, grow and become a confluent layer on the Transwell® membrane.

Preparation of HASMC Bio-Ink

Cultures of human aortic smooth muscle cells (HASMC) were trypsinized, and shaken for 60 minutes on a rotary shaker. Post-shaking, cells were collected, centrifuged, and aspirated into 266 or 500 µm (ID) glass microcapillaries. The cells were then extruded into media covered NovoGel™ plates and incubated for a minimum of 6 hours.

Bioprinting of HASMC Patches Layered with HAEC

Just prior to bioprinting of patches (e.g., segments), human aortic endothelial cell (HAEC) cultures were trypsinized, counted, and then resuspended in HAEC medium at a working concentration of $1 \times 10^6$ cells/10 µL of medium. The HAEC suspension was placed in the bioprinter to be utilized for layering bioprinted patches. The culture media in the multi-well plates having the HDFa's grown on Transwell® membranes was completely aspirated and the plate transferred to the bioprinter. A box was bioprinted using NovoGel™ rods such that the space defined was 8 mm long×1.25 mm wide directly on top of the HDFa's on the membrane. Matured HASMC bio-ink cylinders were loaded onto the bioprinter for printing inside the box. HAEC in suspension were then drawn into a clean microcapillary tube by the bioprinter and dispensed on top of the printed HASMC layer 4 times near the 4 corners of the printed patch. Each drop was 2.5 µL in volume. The construct was incubated for a period of 15-30 minutes before proceeding to print the top NovoGel™ rod layer. Finally, a top layer of NovoGel™ cylinders was printed to create a lattice/mesh type structure. The bioprinted constructs were then covered with appropriate cell culture medium and incubated.

Maturation of Bioprinted Constructs

The bioprinted constructs were incubated for a period of 1-7 days to allow the construct to mature and provide the HAEC sufficient time to form a uniformly thin monolayer on top of the HASMC patch.

Example 12—Hydrogel Lattice Used to Spatially Confine a Construct while Allowing for Direct Contact with Media Cylindrical hydrogel elements were bioprinted utilizing a NovoGen MMX Bioprinter™ (Organovo, Inc., San Diego, CA) across a portion of the top surface of a three-dimensional cell sheet. The lattice provided spatial confinement to the sheet and allowed for direct contact between the sheet and the surrounding media. First, a hydrogel base layer was bioprinted. Second, a hydrogel window was bioprinted defining a space 8 mm long×1.25 mm wide. Third, cellular bio-ink was bioprinted inside the hydrogel window to form the three-dimensional cell sheet. And, fourth, the hydrogel lattice structure was bioprinted. In various experiments, the size of the hydrogel elements was approximately 100 µm to 1 mm in diameter, and the spacing between the elements was approximately 100 µm to 10 mm.

In some experiments, the hydrogel elements were printed along one direction to create long open channels on top of the cell sheet. In other experiments, the hydrogel elements were printed in multiple directions to create a grid-like pattern of open areas on top of the sheet. The hydrogel was comprised of NovoGel™. The lattice structure was optionally extended past the structure and onto the print surface to allow for the application of additional material to affix the structure to the print surface. The resulting lattice was used to spatially confine the construct, but allow for some of the cellular construct to have direct contact with the surrounding nutritive media.

Example 13—Liver Tissue Bioprinted Using Continuous Deposition and Tessellated Functional Unit Structure Engineered liver tissue was bioprinted utilizing a NovoGen MMX Bioprinter™ (Organovo, Inc., San Diego, CA) using a continuous deposition mechanism. The three-dimensional structure of the liver tissue was based on a repeating functional unit, in this case, a hexagon. The bio-ink was composed of hepatic stellate cells and endothelial cells encapsulated in an extrusion compound (surfactant polyol—PF-127).

Preparation of 30% PF-127

A 30% PF-127 solution (w/w) was made using PBS. PF-127 powder was mixed with chilled PBS using a magnetic stir plate maintained at 4° C. Complete dissolution occurred in approximately 48 hours.

Cell Preparation and Bioprinting

A cell suspension comprised of 82% stellate cells (SC) and 18% human aortic endothelial cells (HAEC) and human adult dermal fibroblasts (HDFa) was separated into 15 mL tubes in order to achieve three cell concentrations: $50 \times 10^6$ cells/ml, $100 \times 10^6$ cells/ml, and $200 \times 10^6$ cells/mL following centrifugation. Each cell pellet was resuspended in 30% PF-127 and aspirated into a 3 cc reservoir using the bioprinter. With a 510 µm dispense tip, the encapsulated cells were bioprinted onto a PDMS base plate into a single hexagon (see FIG. 6A) or hexagon tessellation configuration (see FIG. 6B). Each construct received approximately 200 µL of media and was incubated for 20 minutes at room temperature to evaluate construct integrity.

Multi-Layer Bioprinting

For hexagon tessellation experiments, up to (4) sequential layers were bioprinted resulting in a taller structure with more cellular material present. Following fabrication, each construct initially received approximately 200 µL of complete media to assess construct integrity. Constructs were incubated for 20 minutes at room temperature and were then submerged in 20 mLs of complete media.

Results

Figure 7:
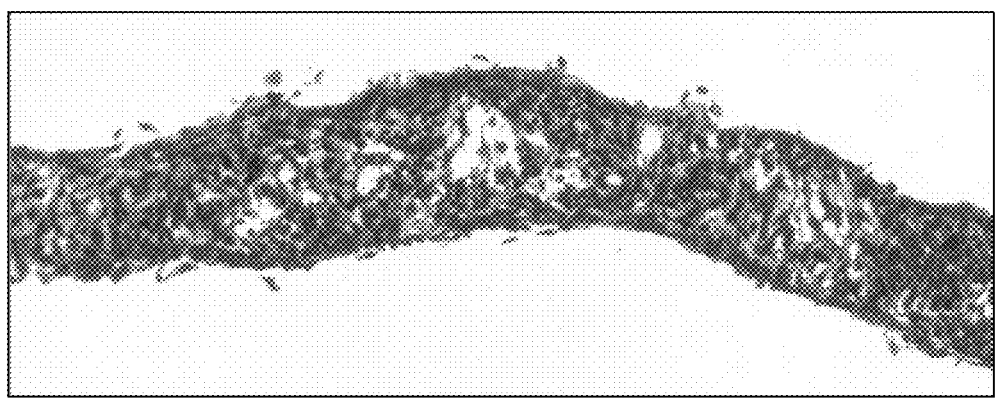
FIG. 7 is a photomicrograph of the H&E stained tessellated construct of FIG. 6, depicting an exemplary "spoke" in the tessellated construct. Shown is H&E staining of formalin-fixed paraffin-embedded tissue sections of stellate cells, endothelial cells, and dermal fibroblasts bioprinted by continuous deposition in a multi-layer tessellated hexagonal structure and then cultured for 18 hours.
Figure 8:
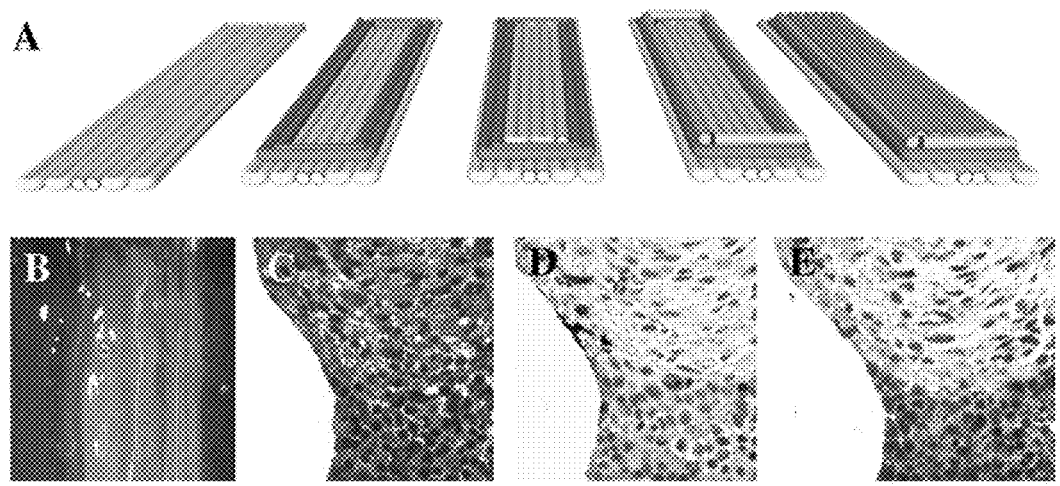
FIG. 8 is a non-limiting schematic diagram (A), macroscopic photograph (B), and series of photomicrographs (C-E) of a bioprinted neotissue with laminar geometry. A NovoGel™ hydrogel base and co-printed confining box were bioprinted, followed by deposition of a first layer comprising liver epithelial cell bio-ink (HepG2 cells), onto which a second layer was bioprinted comprised of hepatic stellate cells and endothelial cells. In this example, the stellate: EC layer was bioprinted via continuous deposition of bio-ink containing a hydrogel extrusion compound (A). Gross images of construct immediately after fabrication demonstrating the two distinct layers of bio-ink (B). H&E staining of sections of formalin-fixed paraffin-embedded constructs (C) following 48 hours of culture reveals distinct morphology of the two layers and establishment of a laminar geometry. CD31-positive cells are restricted to the upper layer of the construct where a suspension of endothelial cells and hepatic stellate cells were bioprinted (D), while IGF-2-positive HepG2 are found only in the bottom layer (E).
Figure 9:
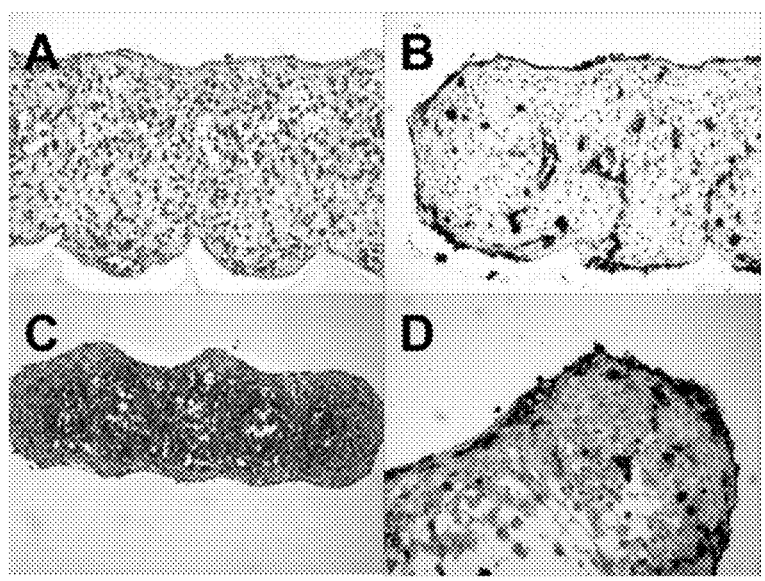
FIG. 9 is a series of photomicrographs depicting cell patterning and layering in bioprinted tissues. H&E staining of paraffin-embedded tissue sections reveals a contiguous neotissue (A) formed by bioprinting polytypic cell populations containing vascular endothelial cells. Staining of the tissue sections with antibody directed at CD31 reveals the presence of centrally-located EC-lined microvessels and an external layer of CD31-positive EC (B). Forced layering was also done by bioprinting a continuous sheet of vascular SMC bio-ink (C) and bioprinting an external layer of CD31-positive EC (D).

Following 18 hours of culture in growth media containing 10% fetal bovine serum (which dissolves PF127), cells contained within the bioprinted geometry were cohered to each other sufficiently to generate an intact, contiguous sheet of tissue that retained the geometrical patterning of the original design (see FIG. 6D). Shown in FIG. 7 is H&E staining of a single segment of the tessellated construct, after fixation in 10% neutral buffered formalin. Cells were found to be viable, intact, and confined to their original printed geometry.

Example 14—Forced Layering

Cell populations (homogeneous or heterogeneous) were prepared for bioprinting as either cylindrical bio-ink or as a cell suspension in Pluronic F-127 (Lutrol, BASF). Briefly, for preparation of bio-ink, cells were liberated from standard tissue culture plastic using either recombinant human trypsin (75 µg/mL, Roche) or 0.05% trypsin (Invitrogen). Following enzyme liberation, cells were washed, collected, counted and combined at desired ratios (i.e., 50:50 hepatic stellate cell (hSC):endothelial cell (EC)) and pelleted by centrifugation. Supernatant was then removed from the cell pellet and the cell mixture was aspirated into a glass microcapillary of desired diameter, typically 500 µm or 250 internal diameter. This cylindrical cell preparation was then extruded into a mold, generated from non cell-adherent hydrogel material with channels for bio-ink maturation. The resulting bio-ink cylinders were then cultured in complete cell culture media for an empirically determined amount of time, typically 2 to 24 hours.

Briefly, for hydrogel cell suspension preparation, cells were liberated from standard cell culture vessel using either of the enzyme-mediated protocols described herein. Liberated cells were then washed with serum containing media, collected, counted and centrifuged to form a dense cell pellet. Supernatant was removed from the resulting cell pellet and cells were then resuspended in cold PF-127 (4° C.) at a concentration of 50 to $200 \times 10^6$ cells/mL (ranging from 10 to $300 \times 10^6$ cells/mL). This cell suspension was then aspirated into a syringe, utilizing a NovoGen MMX Bioprinter™ (Organovo, Inc., San Diego, CA).

Fabrication of tissue constructs with forced cell patterning, layering, or orientation was then accomplished using the bioprinter. Bioprinting of three-dimensional tissue constructs was performed with cylindrical bio-ink, cellular suspensions in water soluble gels, or combinations thereof. To achieve defined cell patterning or layering, combinations of relevant cell populations were included in the bio-ink or cell suspension preparation and then bioprinted in such a fashion that dissolution of the gel material supporting the cell solution, results in defined cell layering around the deposited bio-ink (see FIG. 8). Cell patterning, organization, or layering was also achieved through the utilization and incorporation of defined, discrete cell populations (e.g., hSC and EC), which resulted in predictable and repeatable organization of cells and cellular structures within the bioprinted tissues (see FIG. 9).

In some experiments, final cellular organization within the bioprinted neotissue was observed after a maturation or culture period. Constructs were maintained in a standard laboratory incubator (37° C., humidified chamber supplemented with 5% $CO_2$) and evaluated over time.

Results

Cell patterning, layering, or arrangement was achieved using bioprinting. By bioprinting with bio-ink containing heterogeneous (i.e., polytypic) cell populations, or by combining bio-ink (homogeneous or heterogeneous cell populations) with high density cell-gel or cell suspensions, distinct cell organization was observed. Maturation of these neotissue constructs in a humidified chamber (incubator) resulted in further establishment of distinct cell arrangement, organization and/or segregation in these bioprinted neotissues.

For example, bioprinting of EC:hSC-laden PF-127 on top of bioprinted bio-ink comprising HepG2 cells results in the establishment of distinct layers of the construct with distinct cell populations and discreet tissue morphology. In the case of bio-ink constructs containing hSC and EC, bioprinted constructs that were matured for more than 3 days in complete media were found to contain a distinct layer of EC at the periphery and organized microvessel networks within the core of the construct. Bioprinted constructs fabricated with bio-ink comprising a homogeneous (i.e., monotypic) population of vascular smooth muscle cell onto which a highly concentrated solution of EC was bioprinted were found to contain a distinct layer of EC at the periphery of the construct.

Example 15—Layered Non-Blood Vessel Constructs (Airway Analogues)

Cylindrical bio-ink was prepared with normal human lung fibroblasts (NHLF), small airway epithelial cells (SAEC) and human aortic endothelial cells (EC). Cells were propagated under standard laboratory conditions and cells were cultured in media either purchased from the same vendor as the cells, or media comprising components typically found in the primary literature to be conducive to standard cell culture practices for those particular cell types. Briefly, cells were liberated from standard tissue culture plastic by washing with cation-free phosphate buffered saline (PBS) and then exposed to 0.1-0.05% trypsin (Invitrogen). Liberated cells were then washed in serum-containing media, collected, counted and combined in an appropriate ratio and pelleted by centrifugation. Typically, NHLF and EC were mixed in a ratio of 90:10 to 50:50, NHLF:EC. Supernatant was then removed and the cell pellet was aspirated into a glass microcapillary, which was then submerged in complete media for approximately 15 to 20 minutes. This cylindrical bio-ink structure was then extruded into a non cell-adherent hydrogel mold, containing linear channels and held for 2 to 18 hours.

SAEC were then prepared in a highly concentrated cell suspension. Briefly, SAEC were liberated as described herein, collected, enumerated, and pelleted by centrifugation. Supernatant was removed and the cell pellet was resuspended in a small volume of complete media, yielding a highly concentrated cell pellet of $1 \times 10^5$ cells/µL. This cell suspension was then stored at 4° C. until time of use.

Human lung constructs were then bioprinted into the wells of a multi-well plate or onto the membrane of a cell culture well insert (Transwell, BD). Multicellular NHLF or NHLF:EC bio-ink was used to bioprint a layer of tissue representing the small airway wall. Human airway tissue segments were fabricated with initial dimensions of 1.25 mm×8 mm×0.25 mm (W×L×H). Following bioprinting of the wall layer with NHLF or NHLF:EC bio-ink, a concentrated cell suspension of SAEC was bioprinted on the top surface of the wall, generating a second layer comprising airway epithelium on top of putative airway interstitium (see FIG. 10).

The human airway tissue segments were then submerged in serum-containing complete cell culture media and placed in a standard humidified chamber, supplemented with 5% $CO_2$ for maturation. The bioprinted human airway segments were then cultured in static conditions or stimulated through the addition of cytokine(s) or biomechanical signals (e.g., flow, shear stress, etc.). Bioprinted human lung tissue constructs were then cultured for up to 7 days and evaluated for cell organization, extracellular matrix production, cell viability, and construct integrity (see FIG. 11).

Results

Bioprinted human lung tissue constructs with a layered cellular structure comprising an NHLF wall containing an organized network of EC-lined microvessel profiles and an apical surface comprising small airway epithelial cells were successfully fabricated and maintained in culture. The bioprinted constructs were generated using a multi-layered approach with NHLF or NHLF:EC bio-ink cylinders and a bioprinted layer of SAEC. Upon stimulation with a cytokine believed to be important in disease processes of the lung, morphological changes including tissue thickening and NHLF activation were observed.

Example 16—Layered Blood Vessel Wall Constructs

Cylindrical bio-ink was prepared with vascular smooth muscle cells (SMC) and, in some experiments, dermal fibroblasts (Fb). Briefly, cells were liberated from standard tissue culture plastic by washing with cation-free phosphate buffered saline (PBS) and then exposed to 0.05% trypsin (Invitrogen). Liberated cells were then washed in serum-containing media, collected, counted and, for experiments in which Fb were included, combined in an appropriate ratio and pelleted by centrifugation. Supernatant was then removed and the cell pellet was aspirated into a glass microcapillary, which was then submerged in complete media for approximately 15 to 20 minutes. This cylindrical bio-ink structure was then extruded into a non cell-adherent hydrogel mold, containing linear channels and held for 2 to 18 hours.

Endothelial cells (EC) were then prepared in a highly concentrated cell suspension. Briefly, EC were liberated as described above, collected, enumerated, and pelleted by centrifugation. Supernatant was removed and the cell pellet was resuspended in a small volume of complete media, yielding a highly concentrated cell pellet of $1 \times 10^5$ cells/µL. This cell suspension was then stored at 4° C. until time of use.

Blood vessel wall constructs were then bioprinted into the wells of a multi-well plate or onto the membrane of a cell culture well insert (Transwell, BD). Cylindrical SMC or SMC:Fb bio-ink was used to bioprint the tunica media of a blood vessel wall segment. Blood vessel wall segments were fabricated with initial dimensions of 1.25 mm×8 mm×0.25 mm (W×L×H). Following bioprinting of the putative tunica media with SMC or SMC:Fb bio-ink to form a first layer of tissue, a concentrated cell suspension of EC was bioprinted on the top surface of the first layer to generate a second layer of vascular endothelium, serving as a putative tunica intima (see FIG. 12).

The bioprinted blood vessel wall segments were then submerged in serum-containing complete cell culture media and placed in a standard humidified chamber, supplemented with 5% $CO_2$ for maturation. The bioprinted blood vessel wall segments were then cultured in static conditions or stimulated through the addition of cytokine(s) or biomechanical signals (e.g., flow, shear stress, etc.). Blood vessel wall segments were cultured for up to 7 days and evaluated for cell organization, extracellular matrix production, cell viability and construct integrity (see FIG. 13).

Results

Bioprinted vascular wall segments with a layered cellular structure comprising an SMC-rich media and an EC-lined intima were successfully fabricated and maintained in culture. The bioprinted constructs were generated using a multi-layered approach with SMC or SMC:Fb bio-ink cylinders and a bioprinted layer of EC.

Example 17—Multi-Well Plates

Cell populations (homogeneous or heterogeneous) were prepared for bioprinting using a variety of bio-ink formats, including cylindrical bio-ink aggregates, suspensions of cellular aggregates, or cell suspensions/pastes, optionally containing extrusion compounds. Briefly, for preparation of cylindrical bio-ink, cells were liberated from standard tissue culture plastic using either recombinant human trypsin (75 µg/mL, Roche) or 0.05% trypsin (Invitrogen). Following enzyme liberation, cells were washed, collected, counted, and combined at desired ratios (i.e., 50:50 hepatic stellate cell (hSC):endothelial cell (EC)) and pelleted by centrifugation. Supernatant was then removed from the cell pellet and the cell mixture was aspirated into a glass microcapillary of desired diameter, typically 500 μm or 250 internal diameter. This cylindrical cell preparation was then extruded into a mold, generated from non cell-adherent hydrogel material with channels for bio-ink maturation. The resulting bio-ink cylinders were then cultured in complete cell culture media for an empirically determined amount of time, typically 2 to 24 hours.

For preparation of a cell suspension or cell paste of cellular aggregates, the cell propagation and liberation protocols described herein were followed. At the time of cell pellet generation, supernatant was removed from the pellet and the pellet was transferred to a custom deposition syringe. This syringe was then mounted to the bioprinter deposition head for direct bioprinting of the cell aggregate solution or paste into multi-well plates.

Replicate tissue constructs were then bioprinted within the wells of either a multi-well tissue culture plate (e.g., 6-well or 24-well) or within a multi-well cell culture insert (i.e., Transwell, BD) and then placed into an appropriate multi-well plate. Following bioprinting, the three-dimensional constructs were matured/conditioned with relevant media for some period of time, typically 3 to 14 days. Following maturation, constructs were harvested, fixed and processed for routine histology and immunohistochemistry.

Results

Bioprinted tissues were successfully fabricated within multi-well culture plates or multi-well culture inserts that were then inserted into multi-well plates. This approach allows for generation of replicate bioprinted tissues that are optionally cultured and treated to generate identical or unique culture conditions. This approach results in a significant increase in bioprinting process throughput and sample generation (see FIG. 14).

Example 18—Stimulation of Bioprinted Neotissues

Cylindrical bio-ink comprising relevant heterogeneous (i.e., polytypic) cell populations were prepared. Physiologically-relevant populations (e.g., normal human lung fibroblasts (NHLF) and small airway epithelial cells (SAEC) or vascular smooth muscle cells (SMC) and vascular endothelial cells (EC)) of cells were combined at specific ratios to generate proper bio-ink. In additional experiments, hepatic stellate cells (hSCs) were combined with ECs to generate liver tissue. In additional experiments, hepatic stellate cells (hSCs) were combined with ECs to generate liver tissue. Cells were maintained and propagated under standard laboratory conditions and cells were cultured in media either purchased from the same vendor as the cells, or media comprising components typically found in the primary literature to be conducive to standard cell culture practices for those particular cell types. Cell processing for bio-ink preparation was as follows: briefly, cells were liberated from standard tissue culture plastic by washing with cation-free phosphate buffered saline (PBS) and then exposed to 0.1-0.05% trypsin (Invitrogen). Liberated cells were then washed in serum-containing media, collected, counted, and combined in an appropriate ratio for the stimulation assay or experiment being conducted, and pelleted by centrifugation. Supernatant was then removed and the cell pellet was aspirated into a glass microcapillary, which was then submerged in complete media for approximately 15 to 20 minutes. This cylindrical bio-ink structure was then extruded into a non cell-adherent hydrogel mold, containing linear channels and held for 2 to 18 hours.

For tissue constructs requiring a homogeneous (i.e., monotypic) cell layer, restricted to the upper surface, a secondary cell preparation was utilized containing the relevant cell type. Typically vascular endothelial cells or small airway epithelial cells (for blood vessel wall and human lung tissue models, respectively) were prepared in a highly concentrated cell suspension. Briefly, cells were liberated as described above, collected, enumerated and pelleted by centrifugation. Supernatant was removed and the cell pellet was resuspended in a small volume of complete media, yielding a highly concentrated cell pellet of $1\times10^5$ cells/μL. This cell suspension was then stored at 4° C. until time of use.

Bioprinted tissue constructs were then fabricated into the wells of a multi-well plate or onto the membrane of a cell culture well insert (Transwell, BD). Multiple tissue types were created. Multicellular NHLF or NHLF:EC bio-ink was used to bioprint a thick interstitial tissue to recapitulate the wall of a small airway, and subsequently layered with SAEC to provide the cognate epithelial barrier layer. Vascular SMC or SMC:fibroblast bio-ink was used to bioprint a thick interstitial tissue to recapitulate the blood vessel wall, and subsequently layered with ECs to provide the cognate endothelial barrier. hSC bio-ink was bioprinted in conjunction with ECs into patches that either contained interspersed endothelial networks or endothelial layers. Tissue segments were fabricated with initial dimensions of 1.25 mm×8 mm×0.25 mm (W×L×H). Following bioprinting of the lung construct or blood vessel wall segment, a concentrated cell suspension was bioprinted on top of the previously-dispensed bio-ink layer generating an additional defined layer of cells on the surface of the first layer.

The bioprinted neotissues were then submerged in serum-containing complete cell culture media and placed in a standard humidified chamber, supplemented with 5% $CO_2$ for maturation. The bioprinted neotissues were then cultured and stimulated with a relevant cytokine(s) for a predetermined period of time, formalin-fixed, harvested, and processed for standard histology and immunohistochemistry. The bioprinted tissues were evaluated for characteristics such as, but not limited to for tissue morphology, cell organization, extracellular matrix production, cell proliferation, cell viability, and construct integrity.

Cytokine stimulation was conducted by adding cytokine directly to the culture media and incubating the bioprinted tissues with the added protein to provide direct and prolonged cell access to the proper stimulus. Dose-response experiments were conducted at doses typically ranging from 0.1 to 100 ng/mL, dependent on the ED50 of the experimental cytokine. For experiments in which cytokine stimulation was conducted over more than 48 hours, media was changed and fresh cytokine was added every 48 hours.

Results

Bioprinted neotissues containing physiologically-relevant populations of cells were successfully stimulated with cytokines that had been previously demonstrated to elicit cellular responses in two-dimensional in vitro systems. The responses observed in the bioprinted three-dimensional tissue constructs were observed to be dose-dependent and unique to the cells within the bioprinted construct (see, e.g., FIGS. 11, 15 and 16).

Example 19—Bioprinting of Co-Molded Functional Liver Tissue Microstructure with Continuous Deposition Preparation of 30% PF-127

A 30% PF-127 solution (w/w) was made using PBS. PF-127 powder was mixed with chilled PBS using a magnetic stir plate maintained at 4° C. Complete dissolution occurred in approximately 48 hours.

Cell Preparation and Co-Printing of Mold and Fill

Three mL of PF-127 solution was aspirated into a 3 cc reservoir using the bioprinter and with a 510 µm dispense tip, 30% PF-127 solution was bioprinted onto a 6 well Transwell into a single hexagon shape and layered sequentially 6 times.

A cell suspension, comprised of $7.8 \times 10^7$ hepatic cells (HepG2), was centrifuged at 1000 g for 6 minutes to create the cell paste. Five µL of cell paste was extruded through a 510 µm needle to fill each of the triangular molds (see FIG. 17A). The hexagon mold was incubated at room temperature for 15 minutes. Three mL of media (DMEM supplemented with 10% FBS and 1× penicillin, streptomycin and amphotericin B) was added to the well with the Transwell supported above followed by incubation at 37° C. and 5% $CO_2$. Within 45 minutes the PF-127 mold dissolved into the media leaving the molded hepatic bio-ink intact to form a planar geometry of cells and void spaces (see FIG. 17B). To remove residual PF-127 from the media, the Transwell was transferred into a new well containing 3 mL of media and incubated for two hours. This was repeated an additional 2 times for a total media exchange of 9 mL over 6 hours.

Post 6 hours the Transwell was transferred to a new well with no media and a cell suspension of $2 \times 10^6$ cells, at a ratio of human aortic endothelial cells at 90% and 10% hepatic stellate cells, was dispensed to fill the voids created by the dissolution of PF-127 mold. The hepatic constructs were incubated for 15 minutes at room temperature. Following the 15 minute incubation, 4 mL of media containing a ratio of 85% media (DMEM supplemented with 10% FBS and 1× penicillin, streptomycin and amphotericin B, to support the hepatic and stellate cells and 15% M199 supplemented with 2% LSGS, 10% FBS, HEPES and 1× penicillin, streptomycin and amphotericin B, to support the human aortic endothelial cells). The construct was incubated at 37° C. and 5% $CO_2$ for 48 hours to form a contiguous construct, with planar geometry comprising a lobular (triangular) arrangement of hepatic parenchyma with intervening endothelial cell-comprising tissue.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein are suitably employed in practicing the invention.

What is claimed is:

1. An in vitro method of producing a living, three-dimensional tissue construct comprising:
    a. bioprinting at least one semi-solid or solid bio-ink comprising endothelial cells and a different cell type in the same or separate bio-inks; and
    b. incubating the at least one semi-solid or solid bio-ink in vitro to cohere and form the living, three-dimensional tissue construct comprising a microvascular network consisting of endothelial cells that is located within the construct and is surrounded by cells that are not part of the microvascular network;
    wherein the tissue construct does not comprise an artery or vein.

2. The method of claim 1, wherein the bio-ink comprises multicellular aggregates comprising mammalian cells.

3. The method of claim 1, wherein the bioprinting further comprises arranging a plurality of cell types relative to each other to create a planar geometry in at least one layer.

4. The method of claim 1, comprising bioprinting at least one layer that is compositionally or architecturally distinct from at least one other layer to create a laminar geometry.

5. The method of claim 1, wherein the tissue construct is at least about 25 µm in its smallest dimension at the time of bioprinting, wherein the tissue construct is no greater than about 3 cm in its largest dimension at the time of bioprinting, or both.

6. The method of claim 1, wherein the endothelial cells, the different cell type, or both are differentiated cells.

7. The method of claim 1, wherein the endothelial cells, the different cell type, or both are non-differentiated cells.

8. The method of claim 1, comprising isolating the different cell type from a tissue selected from the group consisting of: liver, gastrointestinal, pancreatic, kidney, lung, tracheal, vascular, skeletal muscle, cardiac, skin, smooth muscle, connective tissue, corneal, genitourinary, breast, reproductive, endothelial, epithelial, fibroblast, neural, adipose, bone, bone marrow, cartilage, mesothelial, endocrine, stromal, lymph, blood, endoderm, ectoderm, mesoderm, or a combination thereof.

9. The method of claim 1, comprising isolating the endothelial cells from a tissue selected from the group consisting of: blood, blood vessel, lymphatic vessel, tissue of the digestive tract, tissue of the genitourinary tract, adipose tissue, tissue of the respiratory tract, tissue of the reproductive system, mesoderm-derived tissue, bone marrow, and umbilical tissue.

10. The method of claim 1, wherein the tissue construct is a vascular wall segment.

11. The method of claim 1, comprising producing multiple tissue constructs and constructing an array from the multiple tissue constructs.

12. The method of claim 1, wherein the at least one semi-solid or solid bio-ink is cylindrical.

13. The method of claim 12, wherein the bioprinting comprises continuous deposition of the at least one semi-solid or solid bio-ink.

14. The method of claim 13, wherein the bioprinting comprises extruding the at least one semi-solid or solid bio-ink through a dispense tip of a bioprinter.

15. The method of claim 14, wherein the dispense tip is connected to a reservoir comprising the at least one semi-solid or solid bio-ink.

16. The method of claim 1, wherein the at least one semi-solid or solid bio-ink is not bioprinted into a pre-formed scaffold.

17. The method of claim 1, comprising bioprinting multiple layers of the at least one semi-solid or solid bio-ink.

18. The method of claim 17, wherein each layer is in direct contact with at least one other layer.

* * * * *